(12) United States Patent
Stayton et al.

(10) Patent No.: US 11,707,483 B2
(45) Date of Patent: *Jul. 25, 2023

(54) MICELLIC ASSEMBLIES

(71) Applicants: University of Washington, Seattle, WA (US); GENEVANT SCIENCES GMBH, Basel (CH)

(72) Inventors: Patrick S. Stayton, Seattle, WA (US); Allan S. Hoffman, Seattle, WA (US); Anthony Convertine, Seattle, WA (US); Craig L. Duvall, Nashville, TN (US); Danielle Benoit, Rochester, NY (US); Robert Overell, Shoreline, WA (US); Paul H. Johnson, Snohomish, WA (US); Anna S. Gall, Woodinville, WA (US); Mary G. Prieve, Lake Forest Park, WA (US); Amber E. E. Paschal, Redmond, WA (US); Charbel Diab, Seattle, WA (US); Priyadarsi De, Mohanpur (IN)

(73) Assignees: UNIVERSITY OF WASHINGTON, Seattle, WA (US); GENEVANT SCIENCES GMBH, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/579,662

(22) Filed: Sep. 23, 2019

(65) Prior Publication Data

US 2020/0147121 A1 May 14, 2020

Related U.S. Application Data

(63) Continuation of application No. 15/499,683, filed on Apr. 27, 2017, now Pat. No. 10,420,790, which is a continuation of application No. 15/059,026, filed on Mar. 2, 2016, now Pat. No. 9,662,403, which is a continuation of application No. 12/992,525, filed as application No. PCT/US2009/043849 on May 13, 2009, now Pat. No. 9,339,558.

(60) Provisional application No. 61/171,369, filed on Apr. 21, 2009, provisional application No. 61/140,774, filed on Dec. 24, 2008, provisional application No. 61/112,048, filed on Nov. 6, 2008, provisional application No. 61/091,294, filed on Aug. 22, 2008, provisional application No. 61/052,908, filed on May 13, 2008, provisional application No. 61/052,914, filed on May 13, 2008.

(51) Int. Cl.
| | |
|---|---|
| A61K 31/713 | (2006.01) |
| A61K 9/107 | (2006.01) |
| C08F 290/06 | (2006.01) |
| C08F 293/00 | (2006.01) |
| C12N 15/11 | (2006.01) |
| C12N 15/87 | (2006.01) |
| A61K 47/69 | (2017.01) |
| A61K 47/58 | (2017.01) |
| A61K 47/54 | (2017.01) |
| A61K 47/60 | (2017.01) |
| A61K 48/00 | (2006.01) |

(52) U.S. Cl.
CPC .......... *A61K 31/713* (2013.01); *A61K 9/1075* (2013.01); *A61K 47/549* (2017.08); *A61K 47/58* (2017.08); *A61K 47/60* (2017.08); *A61K 47/6907* (2017.08); *A61K 48/0041* (2013.01); *C08F 290/062* (2013.01); *C08F 293/005* (2013.01); *C12N 15/111* (2013.01); *C12N 15/87* (2013.01); *C12N 2320/32* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,699,784 | A | 10/1987 | Shih et al. |
| 5,057,313 | A | 10/1991 | Shih et al. |
| 6,306,994 | B1 | 10/2001 | Donald et al. |
| 6,359,054 | B1 | 3/2002 | Lemieux et al. |
| 6,383,811 | B2 | 5/2002 | Wolff et al. |
| 6,410,057 | B1 | 6/2002 | Kweon-Choi et al. |
| 6,780,428 | B2 | 8/2004 | Ranger et al. |
| 6,835,393 | B2 | 12/2004 | Hoffman et al. |
| 6,916,488 | B1 | 7/2005 | Meier et al. |
| 6,919,091 | B2 | 7/2005 | Trubetskoy et al. |
| 6,939,564 | B2 * | 9/2005 | Ranger .................. C08L 53/00 424/497 |
| 7,033,607 | B2 | 4/2006 | Trubetskoy et al. |
| 7,094,810 | B2 | 8/2006 | Sant et al. |
| 7,098,032 | B2 | 8/2006 | Trubetskoy et al. |

(Continued)

FOREIGN PATENT DOCUMENTS

| | | |
|---|---|---|
| CA | 2724105 A1 | 11/2009 |
| CA | 2972694 A1 | 11/2009 |

(Continued)

OTHER PUBLICATIONS

Li et al. Polymer 2006 47:4581-4587 (Year: 2006).*

(Continued)

*Primary Examiner* — Melissa S Mercier
*Assistant Examiner* — Caralynne E Helm
(74) *Attorney, Agent, or Firm* — Christensen O'Connor Johnson Kindness PLLC

(57) ABSTRACT

Provided herein are micellic assemblies comprising a plurality of copolymers. In certain instances, micellic assemblies provided herein are pH sensitive particles.

16 Claims, 18 Drawing Sheets
Specification includes a Sequence Listing.

(56) References Cited

U.S. PATENT DOCUMENTS

| | | |
|---|---|---|
| 7,217,776 B1 | 5/2007 | Mallapragada et al. |
| 7,374,778 B2 | 5/2008 | Hoffman et al. |
| 7,510,731 B2 | 3/2009 | Ranger et al. |
| 7,524,680 B2 | 4/2009 | Wolff et al. |
| 7,718,193 B2 | 5/2010 | Stayton et al. |
| 7,737,108 B1 | 6/2010 | Hoffman et al. |
| 8,367,113 B2 | 2/2013 | Gu et al. |
| 8,822,213 B2 | 9/2014 | Stayton et al. |
| 9,476,063 B2 | 10/2016 | Stayton et al. |
| 9,862,792 B2 | 1/2018 | Stayton et al. |
| 2001/0007666 A1 | 7/2001 | Hoffman et al. |
| 2003/0017206 A1* | 1/2003 | Seo .................... C08G 63/664 424/486 |
| 2003/0134420 A1 | 7/2003 | Lollo et al. |
| 2003/0191081 A1 | 10/2003 | Lemieux et al. |
| 2003/0211167 A1 | 11/2003 | Gustavsson et al. |
| 2004/0054127 A1 | 3/2004 | Jin et al. |
| 2004/0072784 A1 | 4/2004 | Sant et al. |
| 2004/0151775 A1 | 8/2004 | Rozema et al. |
| 2004/0162235 A1 | 8/2004 | Trubetskoy et al. |
| 2005/0070721 A1 | 3/2005 | Bae et al. |
| 2005/0154165 A1 | 7/2005 | Petereit et al. |
| 2005/0220880 A1 | 10/2005 | Lewis et al. |
| 2005/0260276 A1 | 11/2005 | Yang et al. |
| 2006/0030685 A1 | 2/2006 | Boupat et al. |
| 2006/0134221 A1 | 6/2006 | Geall |
| 2006/0165810 A1 | 7/2006 | Discher et al. |
| 2006/0171980 A1 | 8/2006 | Helmus et al. |
| 2006/0217285 A1 | 9/2006 | Destarac |
| 2006/0235161 A1 | 10/2006 | Heller et al. |
| 2007/0003609 A1 | 1/2007 | Collin-Djangone et al. |
| 2007/0010632 A1 | 1/2007 | Kaplan et al. |
| 2007/0037891 A1 | 2/2007 | Esfand et al. |
| 2007/0059271 A1 | 3/2007 | Kataoka et al. |
| 2007/0110709 A1 | 5/2007 | Ranger et al. |
| 2007/0134188 A1 | 6/2007 | Collin-Djangone et al. |
| 2007/0224241 A1 | 9/2007 | Stayton et al. |
| 2008/0069902 A1 | 3/2008 | Zhao et al. |
| 2008/0081075 A1 | 4/2008 | Hsiue et al. |
| 2008/0171067 A1 | 7/2008 | Govindan et al. |
| 2008/0243049 A1 | 10/2008 | Hardy |
| 2009/0036625 A1 | 2/2009 | Chang et al. |
| 2010/0150952 A1 | 6/2010 | Stayton et al. |
| 2010/0159019 A1 | 6/2010 | Yang et al. |
| 2011/0143434 A1 | 6/2011 | Stayton et al. |
| 2011/0143435 A1 | 6/2011 | Stayton et al. |
| 2011/0281934 A1 | 11/2011 | Johnson et al. |
| 2011/0286957 A1 | 11/2011 | Prieve et al. |
| 2012/0021514 A1 | 1/2012 | Johnson et al. |
| 2014/0228516 A1 | 8/2014 | Stayton et al. |
| 2015/0238619 A1 | 8/2015 | Stayton et al. |

FOREIGN PATENT DOCUMENTS

| | | |
|---|---|---|
| EP | 0 321 233 A1 | 6/1989 |
| EP | 2 180 004 A1 | 4/2010 |
| EP | 2281011 A2 | 2/2011 |
| EP | 2620161 A1 | 7/2013 |
| FR | 2 767 829 A1 | 3/1999 |
| WO | 99/29303 A1 | 6/1999 |
| WO | 01/87227 A2 | 11/2001 |
| WO | 03/087188 A1 | 10/2003 |
| WO | 2005/108614 A2 | 11/2005 |
| WO | 2006/016166 A1 | 2/2006 |
| WO | 2007/008300 A2 | 1/2007 |
| WO | 2007/109584 A1 | 9/2007 |
| WO | 2008/004978 A1 | 1/2008 |
| WO | 2008/022309 A2 | 2/2008 |
| WO | 2008/071009 A1 | 6/2008 |
| WO | 2008/085556 A2 | 7/2008 |
| WO | 2008/148174 A1 | 12/2008 |
| WO | 2008/153940 A1 | 12/2008 |
| WO | 2009/009025 A1 | 1/2009 |
| WO | 2009/021728 A2 | 2/2009 |
| WO | 2009/140421 A2 | 11/2009 |
| WO | 2009/140423 A2 | 11/2009 |
| WO | 2009/140427 A2 | 11/2009 |
| WO | 2009/140429 A2 | 11/2009 |
| WO | 2009/140432 A2 | 11/2009 |
| WO | 2010/021770 A1 | 2/2010 |
| WO | 2010/053596 A1 | 5/2010 |
| WO | 2010/053597 A2 | 5/2010 |
| WO | 2010/054266 A2 | 5/2010 |
| WO | 2010/077678 A2 | 7/2010 |

OTHER PUBLICATIONS

Agarwal, A., et al., "Dual-Role Self-Assembling Nanoplexes for Efficient Gene Transfection and Sustained Gene Delivery," Biomaterials 29(5):607-617, Feb. 2008.

Alvarez-Lorenzo, C., et al., "Biophysical Characterization of Complexation of DNA With Block Copolymers of Poly(2-dimethylaminoethyl) Methacrylate, Poly(ethylene oxide), and Poly-(propylene oxide)," Langmuir 21(11):5142-5148, May 2005.

Benoit, D.S.W., et al., "Resensitizing Multidrug Resistant Cells to Doxorubicin Through Plk1 Knockdown Using a Novel pH-Responsive Micelle siRNA Delivery System," Abstracts of Society for Biomaterials Meeting, Apr. 22, 2009, 1 page.

Boeckle, S., et al., "Purification of Polyethylenimine Polyplexes Highlights the Role of Free Polycations in Gene Transfer," Journal of Gene Medicine 6(10):1102-1111, Oct. 2004.

Bulmus, V., et al., "A New pH-Responsive and Glutathione-Reactive, Endosomal Membrane-Disruptive Polymeric Carrier for Intracellular Delivery of Biomolecular Drugs," Journal of Controlled Release 93(2):105-120, Dec. 2003.

Cai, Y., and S.P. Armes, "A Zwitterionic ABC Triblock Copolymer That Forms a 'Trinity' of Micellar Aggregates in Aqueous Solution," Macromolecules 37(19):7116-7122, Sep. 2004.

Cheng, Z., et al., "Brush-Type Amphiphilic Diblock Copolymers From 'Living'/Controlled Radical Polymerizations and Their Aggregation Behavior," Langmuir 21(16):7180-7185, Jul. 2005.

Cheung, C.Y., et al., "A pH-Sensitive Polymer That Enhances Cationic Lipid-Mediated Gene Transfer," Bioconjugate Chemistry 12(6):906-910, Oct. 2001.

Chiu, H.-C., et al., "Synthesis and Characterization of Amphiphilic Poly(ethylene glycol) Graft Copolymers and Their Potential Application as Drug Carriers," Polymer 39(8-9):1609-1616, 1998.

Cho, Y.W., et al., "Polycation Gene Delivery Systems: Escape From Endosomes to Cytosol," Journal of Pharmacy and Pharmacology 55(6):721-734, Jun. 2003.

Convertine, A.J., et al., "Development of a Novel Endosomolytic Diblock Copolymer for siRNA Delivery," Journal of Controlled Release 133(3):221-229, Feb. 2009.

Dufresne, M.-H., et al., "Characterization of Polyion Complex Micelles Designed to Address the Challenges of Oligonucleotide Delivery," Pharmaceutical Research 25(9):2083-2093, Sep. 2008.

Duvall, C.L., et al., "Polymer Enhanced Intracellular Delivery of a Pro-Apoptotic Peptide for Cancer Therapy," Abstracts of Society for Biomaterials Meeting, Apr. 22, 2009, 1 page.

Eliyahu, H., et al., "Novel Dextran-Spermine Conjugates as Transfecting Agents: Comparing Water-Soluble and Micellar Polymers," Gene Therapy 12(6):494-503, Mar. 2005.

El-Sayed, M.E.H., et al., "Rational Design of Composition and Activity Correlations for pH-Sensitive and Glutathione-Reactive Polymer Therapeutics," Journal of Controlled Release 101(1-3):47-58, Jan. 2005.

El-Sayed, M.E.H., et al., "Smart Polymeric Carriers for Enhanced Intracellular Delivery of Therapeutic Macromolecules," Expert Opinion on Biological Therapy 5(1):23-32, Jan. 2005.

Extended European Search Report dated Feb. 5, 2014, issued in corresponding European Application No. 09 825 146.5, filed May 13, 2009, 9 pages.

Extended European Search Report dated Sep. 27, 2011, issued in corresponding International Application No. PCT/US2009/043849, filed May 13, 2009, 5 pages.

Final Office Action dated Apr. 4, 2014, from U.S. Appl. No. 12/992,517, filed Feb. 9, 2011, 21 pages.

(56) References Cited

OTHER PUBLICATIONS

Final Office Action dated Mar. 21, 2014, from U.S. Appl. No. 13/127,962, filed Jul. 26, 2011, 11 pages.
Final Office Action dated Nov. 4, 2014, from U.S. Appl. No. 13/127,959, filed Jul. 27, 2011, 24 pages.
Finne-Wistrand, A., and A.-C. Albertson, "The Use of Polymer Design in Resorbable Colloids," Annual Review of Materials Research 36:369-395, Aug. 2006.
Fishbein, I., et al., "Local Delivery of Gene Vectors From Bare-Metal Stents by Use of a Biodegradable Synthetic Complex Inhibits In-Stent Restenosis in Rat Carotid Arteries," Circulation 117(16):2096-2103, Apr. 2008.
Funhoff, A.M., et al., "Endosomal Escape of Polymeric Gene Delivery Complexes Is Not Always Enhanced by Polymers Buffering at Low pH," Biomacromolecules 5(1):32-39, Jan.-Feb. 2004.
Gary, D.J., et al., "Polymer-Based siRNA Delivery: Perspectives on the Fundamental and Phenomenological Distinctions From Polymer-Based DNA Delivery," Journal of Controlled Release 121(1-2):64-73, Aug. 2007.
Gaucher, G., et al., "Block Copolymer Micelles: Preparation, Characterization and Application in Drug Delivery," Journal of Controlled Release 109(1-3):169-188, Dec. 2005.
Georgiou, T.K., and C.S. Patrickios, "Synthesis, Characterization, and DNA Adsorption Studies of Ampholytic Model Conetworks Based on Cross-Linked Star Copolymers," Biomacromolecules 9(2):574-582, Feb. 2008.
Germershaus, O., et al., "Gene Delivery Using Chitosan, Trimethyl Chitosan or Polyethylenglycol-graft-trimethyl Chitosan Block Copolymers: Establishment of Structure-Activity Relationships In Vitro," Journal of Controlled Release 125(2):145-154, Jan. 2008.
Guo, Y., et al., "Capillary Electrophoresis Analysis of Poly(ethylene glycol) and Ligand-Modified Polylysine Gene Delivery Vectors," Analytical Biochemistry 363(2):204 209, Apr. 2007.
Henry, S.M., et al., "pH-Responsive Poly(styrene-alt-maleic anhydride) Alkylamide Copolymers for Intracellular Drug Delivery," Biomacromolecules 7(8):2407-2414, Aug. 2006.
Heredia, K.L., et al., "Reversible siRNA-Polymer Conjugates by RAFT Polymerization," Chemical Communications 28(28):3245-3247, Jul. 2008.
Hood, J.D., et al., "Tumor Regression by Targeted Gene Delivery to the Neovasculature," Science 296(5577):2404-2407, Jun. 2002.
Inoue, T., et al., "An AB Block Copolymer of Oligo(methyl methacrylate) and Poly(acrylic acid) for Micellar Delivery of Hydrophobic Drugs," Journal of Controlled Release 51(2-3):221-229, Feb. 1998.
International Search Report and Written Opinion dated Jan. 12, 2010, issued in corresponding International Application No. PCT/US2009/043849, filed May 13, 2009, 15 pages.
International Search Report and Written Opinion dated Mar. 7, 2011, issued in International Application No. PCT/US2010/056565, filed Nov. 12, 2010, 12 pages.
Invitation to Pay Additional Fees and Partial International Search Report dated Apr. 26, 2011, issued in International Application No. PCT/US2010/056993, filed Nov. 17, 2010, 6 pages.
Japanese First Office Action, dated Mar. 12, 2013, issued in corresponding Japanese Application No. 2011-509671, filed May 13, 2009, 4 pages.
Jensen, K.D., et al., "Antisense Oligonucleotides Delivered to the Lysosome Escape and Actively Inhibit the Hepatitis B Virus," Bioconjugate Chemistry 13(5):975-984, Sep.-Oct. 2002.
Jeong, J.H., et al., "siRNA Conjugate Delivery Systems," Bioconjugate Chemistry 20(1):5-14, Jan. 2009.
Jeong, Y.-I., et al., "Cellular Recognition of Paclitaxel-Loaded Polymeric Nanoparticles Composed of Poly(γ-benzyl L-glutamate) and Poly(ethylene glycol) Diblock Copolymer Endcapped With Galactose Moiety," International Journal of Pharmaceutics 296(1-2):151-161, May 2005.
Jiang, T., et al., "Adsorption of Plasmid DNA Onto N,N'-(Dimethylamino)ethyl-methacrylate Graft-Polymerized Poly-L-Lactic Acid Film Surface for Promotion of In-Situ Gene Delivery," Biomacromolecules 8(6):1951-1957, Jun. 2007.
Joralemon, M.J., et al., "Synthesis, Characterization, and Bioavailability of Mannosylated Shell Cross-Linked Nanoparticles," Biomacromolecules 5(3):903-913, May-Jun. 2004.
Kabanov, A.V., et al., "Pluronic Micelles as a Tool for Low-Molecular Compound Vector Delivery Into a Cell: Effect of *Staphylococcus aureus* Enterotoxin B on Cell Loading With Micelle Incorporated Fluorenscent Dye," Biochemistry International 26(6):1035-1042, May 1992.
Kataoka, K., et al., "Smart Polymeric Micelles as Nanocarriers for Oligonucleotides and siRNA Delivery," Nucleic Acids Symposium Series 49(1):17-18, Sep. 2005.
Kim, E.-M., et al., "Monitoring the Effect of PEGylation on Polyethylenimine In Vivo Using Nuclear Imaging Technique," Nuclear Medicine and Biology 31(6):781-784, Aug. 2004.
Kono, K., et al., "Transfection Activity of Polyamidoamine Dendrimers Having Hydrophobic Amino Acid Residues in the Periphery," Bioconjugate Chemistry 16(1):208-214, Jan. 2005.
Kulkarni, S., et al., "Controlling the Aggregation of Conjugates of Streptavidin With Smart Block Copolymers Prepared via the RAFT Copolymerization Technique," Biomacromolecules 7(10):2736-2741, Oct. 2006.
Kurisawa, M., et al., "Transfection Efficiency Increases by Incorporating Hydrophobic Monomer Units Into Polymeric Gene Carriers," Journal of Controlled Release 68(1):1-8, Jul. 2000.
Kyriakides, T.R., et al., "pH-Sensitive Polymers That Enhance Intracellular Drug Delivery In Vivo," Journal of Controlled Release 78(1-3):295-303, Jan. 2002.
Lam, J.K.W., et al., "Phosphocoline-Polycation Diblock Copolymers as Synthetic Vectors for Gene Delivery," Journal of Controlled Release 100(2):293-312, Nov. 2004.
First Office Action (JP) dated May 31, 2016, issued in corresponding Japanese Application No. 2015-107802, filed May 13, 2009, 4 pages.
Prieve, M.G., et al., "Multiblock Copolymers," U.S. Appl. No. 15/254,874, filed Sep. 1, 2016.
Yu, H., et al., "A Novel Amphiphilic Double-[60]Fullerene-Capped Triblock Copolymer," Macromolecules 38(23):9889-9893, Nov. 2005.
Zhao, X., et al.,"Nanostructure of Polyplexes Formed Between Cationic Diblock Copolymer and Antisense Dligodeoxynucleotide and Its Influence on Cell Transfection Efficiency," Biomacromolecules 8(11):3493-3502, Nov. 2007.
Non-Final Office Action dated Mar. 24, 2016, issued in corresponding U.S. Appl. No. 14/630,477, filed Feb. 24, 2015, 10 pages.
Chiefari, Y. K., et al. "Living Free-Radical Polymerization by Reversible Addition-Fragmentation Chain Transfer: The RAFT Process," Macromolecules, vol. 31, pp. 5559-5562, 1998.
Office Action dated May 16, 2018, in corresponding Canadian Application No. 2972694, filed May 13, 2009, 6 pages.
Office Action dated Jun. 7, 2017, issued in corresponding Indian Patent Application No. 8578/DELNP/2010, filed Dec. 2, 2010, 6 pages.
Official Action from the Brazilian Patent Office dated Jun. 28, 2019, issued in corresponding Brazilian Application No. PI0912159-5, filed May 13, 2009, 4 pages.
Le Garrec, D., et al., "Micelles in Anticancer Drug Delivery," American Journal of Drug Delivery 2(1):15-42, Mar. 2004.
Lee, E.S., et al., "Poly(L-histidine)-PEG Block Copolymer Micelles and pH-Induced Destabilization," Journal of Controlled Release 90(3):363-374, Jul. 2003.
Lee, E.S., et al., "Super pH-Sensitive Multifunctional Polymeric Micelle," Nano Letters 5(2):325-329, Feb. 2005.
Lomas, H., et al., "Biomimetic pH Sensitive Polymersomes for Efficient DNA Encapsulation and Delivery," Advanced Materials 19(23):4238-4243, Dec. 2007.
Lowe, A.B., and C.L. McCormick, "Stimuli Responsive Water-Soluble and Amphiphilic (Co)polymers," Chap. 1, in C.L. McCormick (ed.), "Stimuli-Responsive Water Soluble and Amphiphilic Polymers," ACS Symposium Series, American Chemical Society, Washington, D.C., 2000, vol. 780, pp. 1-13.

(56) References Cited

OTHER PUBLICATIONS

Meyer, M., et al., "Synthesis and Biological Evaluation of a Bioresponsive and Endosomolytic siRNA-Polymer Conjugate," Molecular Pharmaceutics 6(3):752-762, May-Jun. 2009.

Meyer, O., et al., "Copolymers of N-Isopropylacrylamide Can Trigger pH Sensitivity to Stable Liposomes," FEBS Letters 421(1):61-64, Jan. 1998.

Mountrichas, G., and S. Pispas, "Synthesis and pH Responsive Self-Assembly of New Double Hydrophilic Block Copolymers," Macromolecules 39(14):4767-4774, Jul. 2006.

Murthy, N., et al., "Bioinspired pH-Responsive Polymers for the Intracellular Delivery of Biomolecular Drugs," Bioconjugate Chemistry 14(2):412-419, Mar.-Apr. 2003.

Murthy, N., et al., "The Design and Synthesis of Polymers for Eukaryotic Membrane Disruption," Journal of Controlled Release 61(1-2):137-143, Aug. 1999.

Nagasaki, Y., et al., "Sugar-Installed Block Copolymer Micelles: Their Preparation and Specific Interaction With Lectin Molecules," Biomacromolecules 2(4):1067-1070, Winter 2001.

Neu, M., et al., "Recent Advances in Rational Gene Transfer Vector Design Based on Poly(ethylene imine) and Its Derivatives," Journal of Gene Medicine 7(8):992-1009, Aug. 2005.

Office Action dated Apr. 17, 2014, from U.S. Appl. No. 13/059,946, filed May 2, 2011, 6 pages.

Office Action dated Apr. 25, 2014, from U.S. Appl. No. 12/992,536, filed Feb. 25, 2011, 13 pages.

Office Action dated Apr. 7, 2014, from U.S. Appl. No. 13/127,959, filed Jul. 27, 2011, 15 pages.

Office Action dated May 20, 2015, from U.S. Appl. No. 13/127,962, filed Jul. 26, 2011, 10 pages.

Office Action dated Sep. 26, 2014, from U.S. Appl. No. 12/992,517, filed Feb. 9, 2011, 15 pages.

Ogris, M., et al., "PEGylated DNA/Transferrin—PEI Complexes: Reduced Interaction With Blood Components, Extended Circulation in Blood and Potential for Systemic Gene Delivery," Gene Therapy 6(4):595-605, Apr. 1999.

Oishi, M., et al., "Lactosylated Poly(ethylene glycol)-siRNA Conjugate Through Acid-Labile β-Thiopropionate Linkage to Construct pH-Sensitive Polyion Complex Micelles Achieving Enhanced Gene Silencing in Hepatoma Cells," Journal of the American Chemical Society 127(6):1624-1625, Feb. 2005.

Oishi, M., et al., "pH-Responsive Oligodeoxynucleotide (ODN)-Poly(Ethylene Glycol) Conjugate Through Acid-Labile β-Thiopropionate Linkage: Preparation and Polyion Complex Micelle Formation," Biomacromolecules 4(5):1426-1432, Aug. 2003.

Oupicky, D., et al., "DNA Delivery Systems Based on Complexes of DNA With Synthetic Polycations and Their Copolymers," Journal of Controlled Release 65(1-2):149-171, Mar. 2000.

Patrickios, C.S., et al., "Diblock, ABC Triblock, and Random Methacrylic Polyampholytes: Synthesis by Group Transfer Polymerization and Solution Behavior," Macromolecules 27(4):930-937, Feb. 1994.

Peppas, N.A., "Is There a Future in Glucose-Sensitive, Responsive Insulin Delivery Systems?" Drug Delivery Science and Technology 14(4):247-256, Sep. 2004.

Preliminary Rejection dated Sep. 15, 2015, issued in corresponding Korean Application No. 10-2010-7027808, filed May 13, 2009, 9 pages.

Raso, V., "Intracellular Targeting Using Bispecific Antibodies," Methods in Molecular Medicine 25:37-49, Jan. 2000.

Read, M.L., et al., "Physicochemical and Biological Characterisation of an Antisense Oligonucleotide Targeted Against the Bcl-2 mRNA Complexed With Cationic-Hydrophilic Copolymers," European Journal of Pharmaceutical Sciences 10(3):169-177, May 2000.

Rozema, D.B., et al., "Dynamic PolyConjugates for Targeted In Vivo Delivery of siRNA to Hepatocytes," Proceedings of the National Academy of Sciences (PNAS) 104(32):12982-12987, Aug. 2007.

Satturwar, P., et al., "pH-Responsive Polymeric Micelles of Poly-(ethylene glycol)-b-poly(alkyl(meth)acrylate-co-methacrylic acid): Influence of the Copolymer Composition on Self-Assembling Properties and Release of Candesartan Cilexetil," European Journal of Pharmaceutics and Biopharmaceutics 65(3):379-387, Mar. 2007.

Sawant, R.M., et al., "'SMART' Drug Delivery Systems: Double-Targeted pH-Responsive Pharmaceutical Nanocarriers," Bioconjugate Chemistry 17(4):943-949, Jul.-Aug. 2006.

Scales, C.W., et al., "Corona-Stabilized Interpolyelectrolyte Complexes of SiRNA With Nonimmunogenic, Hydrophilic/Cationic Block Copolymers Prepared by Aqueous RAFT Polymerization," Macromolecules 39(20):6871-6881, Oct. 2006.

Segura, T., and J.A. Hubbell, "Synthesis and In Vitro Characterization of an ABC Triblock Copolymer for siRNA Delivery," Bioconjugate Chemistry 18(3):736-745, May 2007.

Singapore Search Report and Written Opinion dated Jun. 26, 2012, issued in Singapore Application No. 201008332-7, filed May 13, 2009, 13 pages.

Stayton, P.S., and A.S. Hoffman, "'Smart' pH-Responsive Carriers for Intracellular Delivery of Biomolecular Drugs," in V. Torchilin (ed.), "Fundamental Biomedical Technologies: Multifunctional Pharmaceutical Nanocarriers," Springer Science+Business Media, LLC, New York, May 2008, vol. 4, pp. 143-159.

Stayton, P.S., et al., "Intelligent Biohybrid Materials for Therapeutic and Imaging Agent Delivery," Proceedings of the IEEE 93(4):726-736, Apr. 2005.

Takeda, N., et al., "Temperature-Responsive Polymeric Carriers Incorporating Hydrophobic Monomers for Effective Transfection in Small Doses," Journal of Controlled Release 95(2):343-355, Mar. 2004.

Taton, D., et al., "Direct Synthesis of Double Hydrophilic Statistical Di- and Triblock Copolymers Comprised of Acrylamide and Acrylic Acid Units via the MADIX Process," Macromolecular Rapid Communications 22(18):1497-1503, Dec. 2001.

Teoh, S.K., et al., "Self-Assembly of Stimuli-Responsive Water-Soluble [60]Fullerene End-Capped Ampholytic Block Copolymer," Journal of Physical Chemistry B 109(10):4431-4438, Feb. 2005.

Torchilin, V.P., "Micellar Nanocarriers: Pharmaceutical Perspectives," Pharmaceutical Research 24(1):1-16, Jan. 2007.

Turk, M.J., et al., "Characterization of a Novel pH-Sensitive Peptide That Enhances Drug Release From Folate-Targeted Liposomes at Endosomal pHs," Biochimica et Biophysica Acta 1559(1):56-68, Feb. 2002.

Varghese, O.P., et al., "In Situ Cross-Linkable High Molecular Weight Hyaluronan-Bisphosphonate Conjugate for Localized Delivery and Cell-Specific Targeting: A Hydrogel Linked Prodrug Approach," Journal of the American Chemical Society 131(25):8781-8783, Jul. 2009.

Veron, L., et al., "Hydrolyzable p(DMAPEMA) Polymers for Gene Delivery," Macromolecular Bioscience 6(7):540-554, Jul. 2006.

Wakebayashi, D., et al., "Lactose-Conjugated Polyion Complex Micelles Incorporating Plasmid DNA as a Targetable Gene Vector System: Their Preparation and Gene Transfecting Efficiency Against Cultured HepG2 Cells," Journal of Controlled Release 95(3):653-664, Mar. 2004.

Wang, L., et al., "Delivery of Antisense Oligonucleotides Using HPMA Polymer: Synthesis of a Thiol Polymer and Its Conjugation to Water-Soluble Molecules," Bioconjugate Chemistry 9(6):749-757, Nov.-Dec. 1998.

Wei, J.-S., et al., "Temperature- and pH-Sensitive Core-Shell Nanoparticles Self-Assembled From Poly(N-isopropylacrylamide-co-acrylic acid-co-cholesteryl acrylate) for Intracellular Delivery of Anticancer Drugs," Frontiers in Bioscience 10:3058-3067, Sep. 2005.

Yamamoto, S.-I., et al., "Temperature- and pH-Responsive Dense Copolymer Brushes Prepared by ATRP," Macromolecules 41(19):7013-7020, Oct. 2008.

Yasugi, K., et al., "Sugar-Installed Polymer Micelles: Synthesis and Micellization of Poly(ethylene glycol)-poly(D,L-lactide) Block Copolymers Having Sugar Groups at the PEG Chain End," Macromolecules 32(24):8024-8032, Nov. 1999.

Yessine, M.-A., et al., "Proton-Actuated Membrane-Destabilizing Polyion Complex Micelles," Bioconjugate Chemistry 18(3):1010-1014, May-Jun. 2007.

(56) References Cited

OTHER PUBLICATIONS

Yoo, H.S., and T.G. Park, "Folate Receptor Targeted Biodegradable Polymeric Doxorubicin Micelles," Journal of Controlled Release 96(2):273-283, Apr. 2004.

York, A.W., et al., "Advances in the Synthesis of Amphiphilic Block Copolymers via RAFT Polymerization: Stimuli-Responsive Drug and Gene Delivery," Advanced Drug Delivery Reviews 60(9):1018-1036, Jun. 2008.

Canadian Examination Report dated Apr. 12, 2021, issued in corresponding Canadian Application No. 3,065,577 filed May 13, 2009, 3 pages.

* cited by examiner

FIG. 1A

| Polymer | Structure $[D]_{MW_1}\text{-}[B_x\text{-}P_y\text{-}D_z]_{MW_2}$ | Mn Kda | Block Ratio $MW_2/MW_1$ |
|---|---|---|---|
| P7v1 | $[D]_{9.1K}\text{-}[B_{48}\text{-}P_{29}\text{-}D_{23}]_{11.37K}$ | 19 | 1.2 |
| P7v2 | $[D]_{10K}\text{-}[B_{46}\text{-}P_{18}\text{-}D_{37}]_{8.9K}$ | 19 | 0.9 |
| P7v3 | $[D]_{6.5K}\text{-}[B_{41}\text{-}P_{39}\text{-}D_{20}]_{9.5K}$ | 16 | 1.5 |
| P7v6 | $[D]_{9.1K}\text{-}[B_{52}\text{-}P_{26}\text{-}D_{22}]_{21.9K}$ | 31 | 2.4 | x, y, z ARE MOLE %. MOLECULAR WEIGHTS WERE DETERMINED BY GEL PERMEATION CHROMATOGRAPHY USING PMMA STANDARDS. COMPOSITIONS WERE DETERMINED BY NMR SPECTROSCOPY

FIG. 1B

| Polymer | Mn (kDa) | PDI | %PEGMA | %DMAEMA | Mn (kDa) | PDI | %BMA | %DMAEMA | %PAA |
|---|---|---|---|---|---|---|---|---|---|
| | FIRST BLOCK | | | | SECOND BLOCK | | | | |
| P7-PEGMA100 | 22.24 | 1.34 | 100 | 0 | 45.5 | 1.48 | 50 | 28 | 22 |
| P7-PEGMA20 | 11.44 | 1.33 | 17 | 83 | 41.0 | 1.52 | 56 | 23 | 21 |
| P7-PEGMA10 | 11.01 | 1.31 | 10 | 90 | 42.0 | 1.42 | 51 | 23 | 26 |
| P7-PEGMA5 | 10.60 | 1.17 | 5 | 95 | 27.1 | 1.27 | - | - | - |
| P7-PEGMA-50-14kDa | 14.50 | 1.35 | 46 | 54 | 38.1 | 1.44 | 55 | 25 | 20 |
| P7-PEGMA-50-24kDa | 24.25 | 1.23 | 47 | 53 | 38.4 | 1.45 | 52 | 23 | 25 |

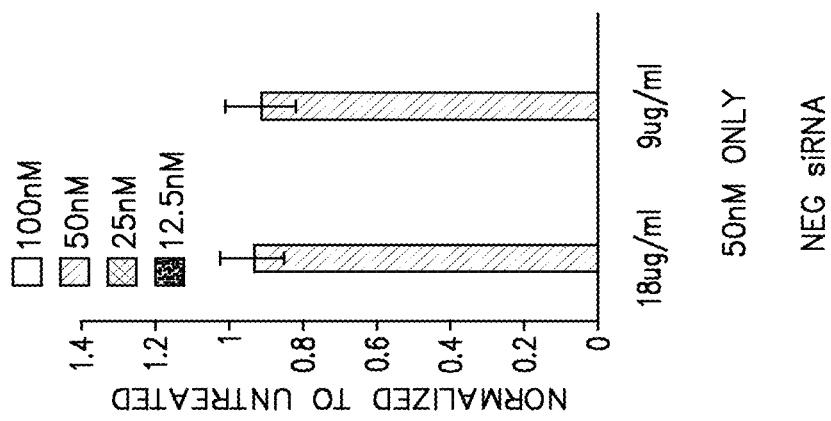
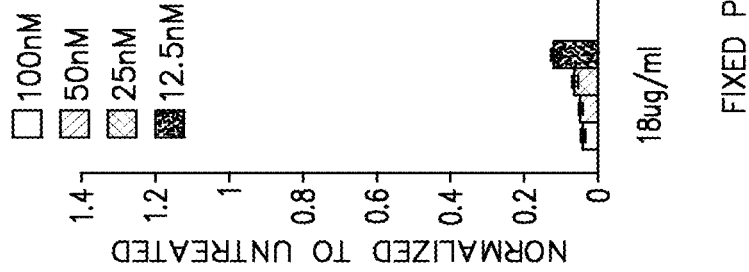
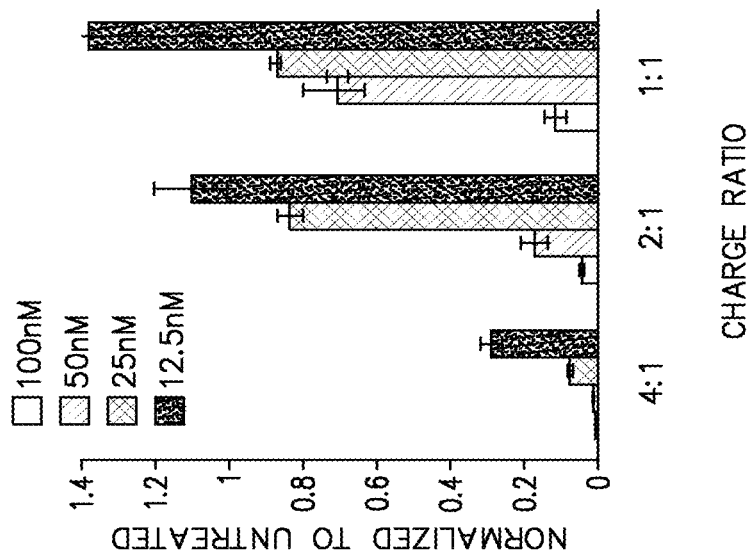

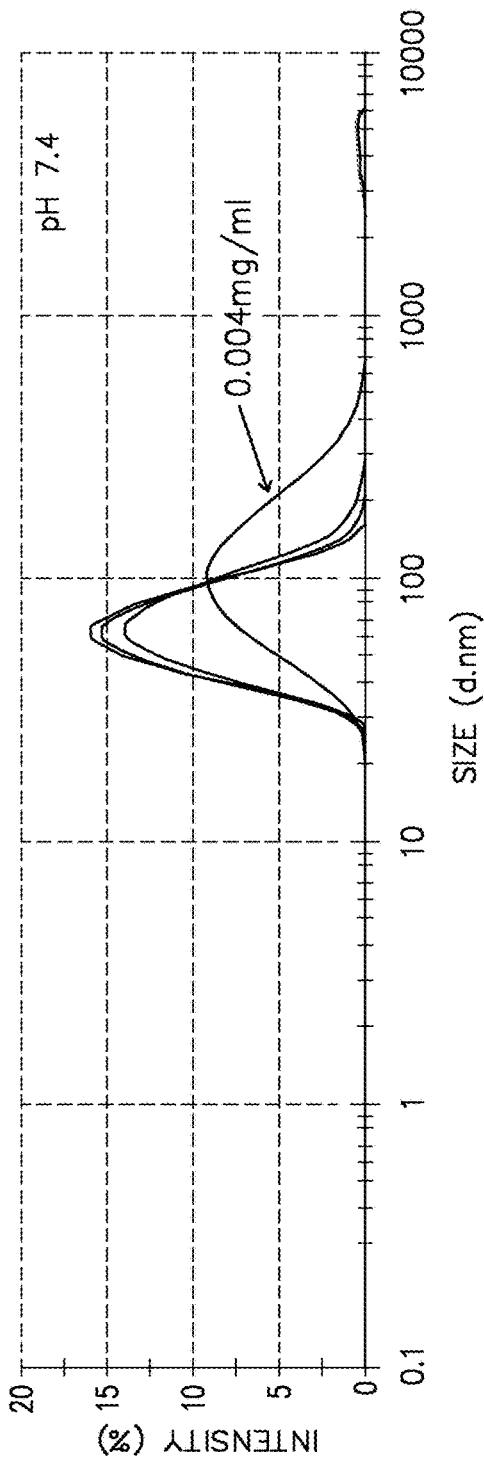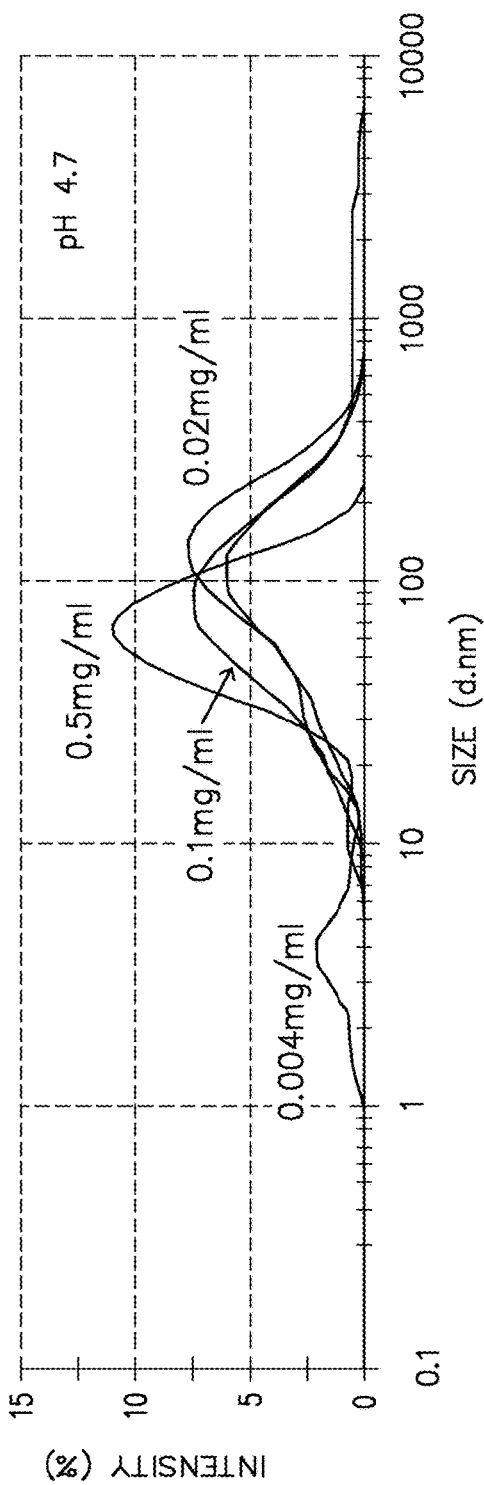

FIG. 12A

Polymer concentrations and charge ratios

|  | 100 nM | 50 nM | 25 nM | 12.5 nM |
|---|---|---|---|---|
| 4:1 | 36 ug/ml | 18 ug/ml | 9 ug/ml | 4.5 ug/ml |
| 2:1 | 18 ug/ml | 9 ug/ml | 4.5 ug/ml | 2.2 ug/ml |
| 1:1 | 9 ug/ml | 4.5 ug/ml | 2.2 ug/ml | 1.1 ug/ml |
| 18 ug/ml | 2:1 | 4:1 | 8:1 | 16:1 |
| 9 ug/ml | 1:1 | 2:1 | 4:1 | 8:1 |
| 4.5 ug/ml | 0.5:1 | 1:1 | 2:1 | 4:1 |
| 2.2 ug/ml | 0.25:1 | 0.5:1 | 1:1 | 2:1 |

FIG. 12B

% Knockdown Results

| 100 nM | 50 nM | 25 nM | 12.5 nM |
|---|---|---|---|
| 99% | 98% | 92% | 71% |
| 95% | 82% | 16% | -10% |
| 88% | 28% | 13% | -38% |
| 96% | 95% | 93% | 88% |
| 89% | 78% | 79% | 63% |
| 94% | 18% | 0% | -7% |
| 43% | 19% | 7% | 0% |

GALACTOSE END FUNCTIONALIZED POLY[DMAEMA]-macro CTA

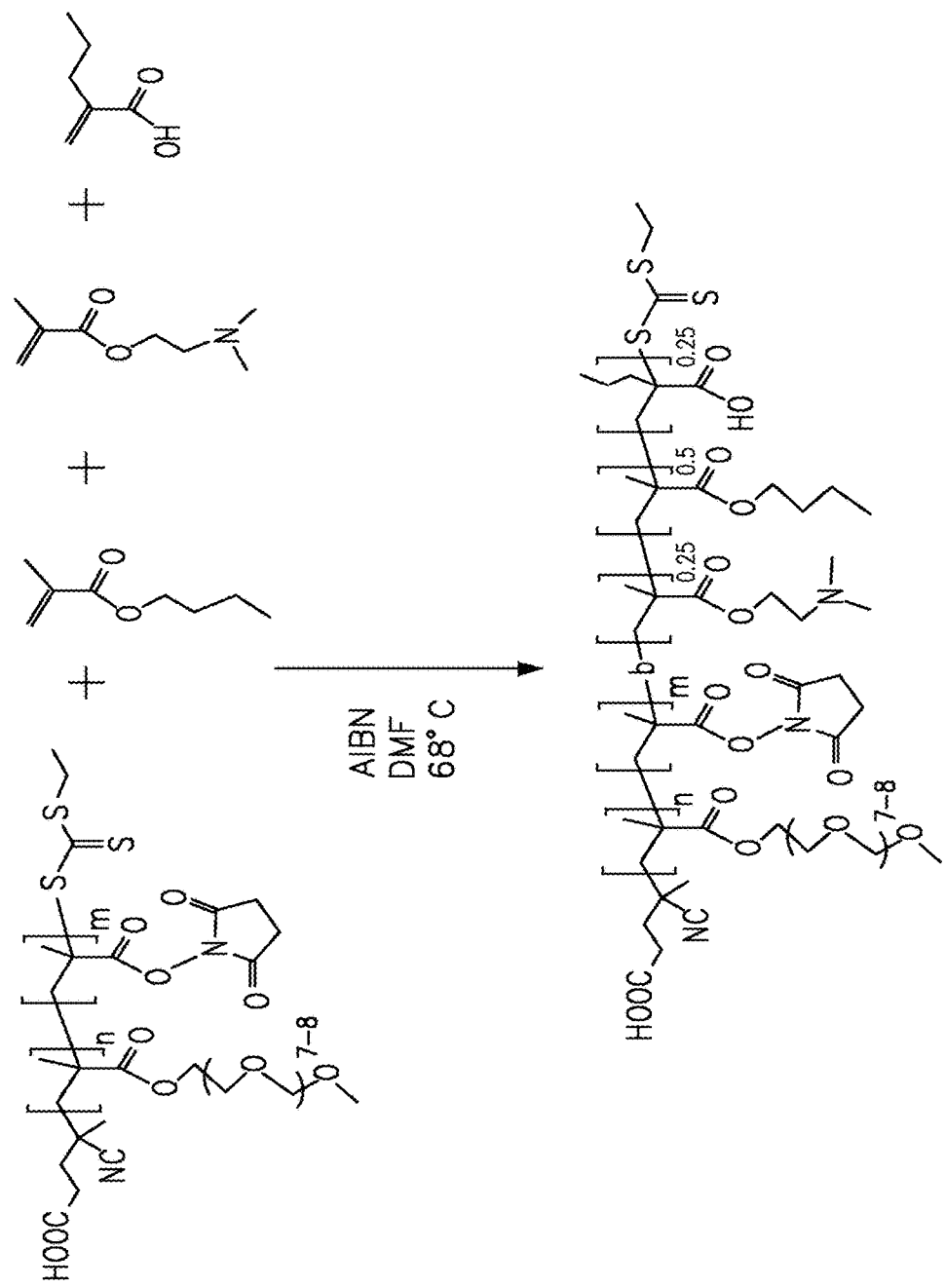

FIG. 15A

RAFT CO-POLYMERIZATION OF PEGMA AND MAA-NHS

[PEGMA]:[MAA-NHS]=75:25

| NAME | FW(g/mol) | EQUIV. | mol | WEIGHT | ACTUAL WEIGHT |
|---|---|---|---|---|---|
| PEGMA | 475 | 112.5 | $5.5958 \times 10^{-3}$ | 2.658g | 2.6641g |
| MAA-NHS | 183.16 | 37.5 | $1.8672 \times 10^{-3}$ | 0.342g | 0.3422g |
| ECT | 263.4 | 1 | $4.9740 \times 10^{-5}$ | 13.1mg | 13.8mg |
| AIBN | 164.21 | 0.04 | $1.9896 \times 10^{-6}$ | 0.33mg | 0.34mg |

DMF = 3.0 g; N$_2$ PURGING: 30 min; CONDUCT POLYMERIZATION AT 68°C. POLYM. TIME=2h 5m COPOLYMERS WERE DIALYZED AGAINST METHANOL (1 L × 8) FOR 50h, USING MWCO MEMBRANE 2K; METHANOL WAS REMOVED UNDER THE HOOD, DRIED UNDER VACUUM 3h, FINALLY LYOPHILIZED FOR 3h.

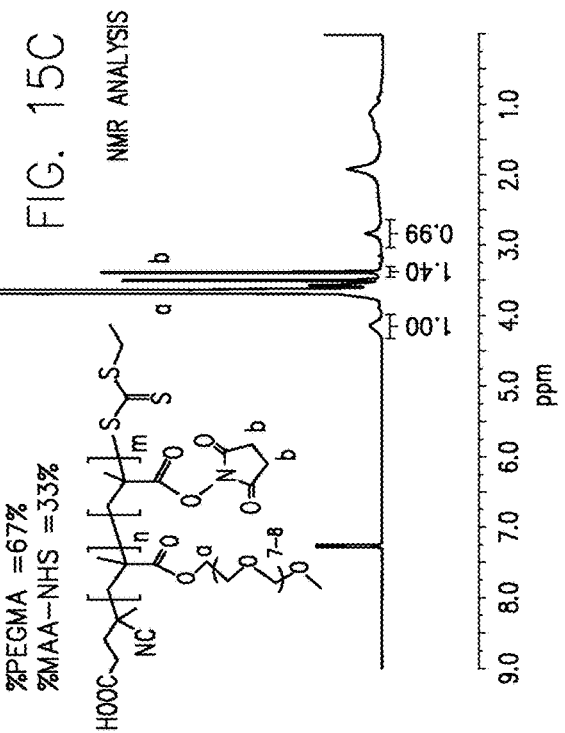

FIG. 15C NMR ANALYSIS

%PEGMA = 67%
%MAA-NHS = 33%

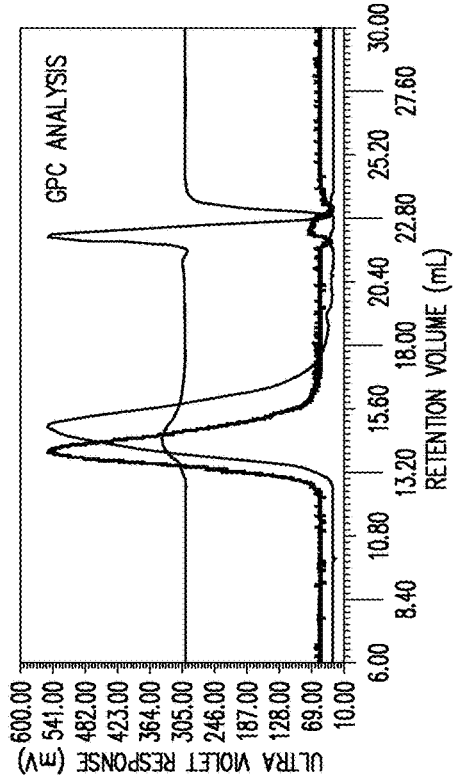

FIG. 15B GPC ANALYSIS dn/dc=0.0465
$M_n$,GPC=33,000 g/mol
PDI=1.42

STRUCTURES OF CONJUGATABLE siRNAs AND PYRIDYL DISULFIDE AMINE

MICELLIC ASSEMBLIES

CROSS-REFERENCE TO RELATED APPLICATIONS

This application is a continuation of U.S. application Ser. No. 15/499,683, filed Apr. 27, 2017, which is continuation of U.S. application Ser. No. 15/059,026, filed Mar. 2, 2016, issued as U.S. Pat. No. 9,662,403, which is a continuation of U.S. Application Ser. No. 12/992,525, filed Feb. 8, 2011, issued as U.S. Pat. No. 9,339,558, which is a National Stage of PCT/US2009/043849, filed May 13, 2009, which claims the benefit of U.S. Provisional Application No. 61/171,369, filed Apr. 21, 2009, U.S. Provisional Application No. 61/140,774, filed Dec. 24, 2008, U.S. Provisional Application No. 61/112,048, filed Nov. 6, 2008, U.S. Provisional Application No. 61/091,294, filed Aug. 22, 2008, U.S. Provisional Application No. 61/052,914, filed May 13, 2008, and U.S. Provisional Application No. 61/052,908, filed May 13, 2008, each of which is hereby incorporated by reference in its entirety.

STATEMENT AS TO FEDERALLY SPONSORED RESEARCH

This invention was made with Government support under Grant No. R01 EB002991, awarded by the National Institutes of Health. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 35789_SEQ-_Final.txt. The text file is 4 KB, was created on Feb. 9, 2011, and is being submitted via EFS-Web.

Statement of Joint Research Agreement

The subject matter of the claimed invention was made as a result of activities undertaken within the scope of a joint research agreement, within the meaning of 35 U.S.C. § 103(c)(3) and 37 C.F.R. § 1.104(c)(4)(ii), by or on behalf of the University of Washington and PhaseRx, Inc., that was in effect on or before the claimed invention was made.

FIELD OF THE INVENTION

Described herein are micellic assemblies formed from polymers and the use of such micellic assemblies.

BACKGROUND OF THE INVENTION

In certain instances, it is beneficial to provide therapeutic agents (e.g., oligonucleotides) to living cells. In some instances, delivery of such polynucleotides to a living cell provides a therapeutic benefit.

SUMMARY OF THE INVENTION

Provided in certain embodiments herein is a micellic assembly comprising a plurality of membrane destabilizing block copolymers, the micellic assembly comprising a core and a shell, wherein the core comprises a plurality of core blocks of the membrane destabilizing block copolymers, wherein the shell comprises a plurality of shell blocks of the membrane destabilizing block copolymers, wherein the core block is a pH dependent membrane destabilizing hydrophobe, and wherein the shell block is hydrophilic at about a neutral pH. In some embodiments, the term 'membrane' refers to a cytoplasmic membrane, a vesicle membrane, a coated pit membrane, an endosome membrane, and/or a cell membrane.

Provided in certain embodiments herein is a micellic assembly comprising a plurality of membrane destabilizing block copolymers, the micellic assembly comprising a core and a shell, wherein the core comprises a plurality of core blocks of the membrane destabilizing block copolymers, wherein the shell comprises a plurality of shell blocks of the membrane destabilizing block copolymers, wherein the core block is a pH dependent membrane destabilizing hydrophobe comprising a first chargeable species that is anionic at about neutral pH, the core block being a copolymer block, and wherein the shell block is hydrophilic at about a neutral pH. When the pH is at about the $pK_a$ of the chargeable species, there will exist an equilibrium distribution of chargeable species in both forms. In the case of an anionic species, about 50% of the population will be anionic and about 50% will be non-charged when the pH is at the $pK_a$ of the anionic species. The further the pH is from the $pK_a$ of the chargeable species, there will be a corresponding shift in this equilibrium such that at higher pH values, the anionic form will predominate and at lower pH values, the uncharged form will predominate. The embodiments described herein include the form of the copolymers at any pH value.

Provided in some embodiments herein is a micellic assembly comprising a plurality of membrane destabilizing block copolymers, the micellic assembly comprising a core and a shell, wherein the core comprises a plurality of core blocks of the membrane destabilizing block copolymers, wherein the shell comprises a plurality of shell blocks of the membrane destabilizing block copolymers, wherein the core block is a pH dependent membrane destabilizing hydrophobe comprising a first chargeable species that is anionic at about neutral pH, the first chargeable species being hydrophobically shielded, and wherein the shell block is hydrophilic at about a neutral pH.

Provided in certain embodiments herein is a micellic assembly comprising a plurality of membrane destabilizing block copolymers, the micellic assembly comprising a core and a shell, wherein the core comprises a plurality of core blocks of the membrane destabilizing block copolymers, wherein the shell comprises a plurality of shell blocks of the membrane destabilizing block copolymers, wherein the core block is a pH dependent membrane destabilizing hydrophobe comprising a first chargeable species that is anionic at about neutral pH and a second chargeable species that is cationic at about neutral pH, and wherein the shell block is hydrophilic at about a neutral pH.

Provided in some embodiments herein is a micellic assembly comprising a plurality of membrane destabilizing block copolymers, the micellic assembly comprising a core and a shell, wherein the core comprises a plurality of core blocks of the membrane destabilizing block copolymers, wherein the shell comprises a plurality of shell blocks of the membrane destabilizing block copolymers, wherein the core block is a pH dependent membrane destabilizing hydrophobe comprising a first chargeable species that is anionic at about neutral pH, and wherein the shell block is a temperature independent hydrophile at about a neutral pH. In one embodiment, "temperature independent hydrophile" refers to a hydrophile that has hydrophilic properties that are substantially invariant over the temperature range 20 to 40 degrees Celsius. As a result, the hydrophilic properties are substantially invariant prior to and following administration of the micellic assembly to a human patient. In some embodiments, a micellic assembly provided herein comprises membrane destabilizing block copolymers that are membrane destabilizing at a pH of about 6.5, or lower, about 5.0 to about 6.5, or about 6.2, or lower.

In some embodiments, membrane destabilizing block copolymers utilized in the micellic assemblies provided herein comprise at least two blocks, or are diblock copolymers.

In certain embodiments, the shell of the micellic assembly comprises a polyethylene glycol group. In specific embodiments, the shell block of the membrane destabilizing block copolymer is or comprises polyethylene glycol. In some embodiments, the shell block comprises a plurality of shell monomeric units, and wherein one or more of the plurality of shell monomeric units are substituted or functionalized with a PEG group.

In some embodiments, the form of the micellic assembly over the pH range of about 6.2 to 7.5 is a micelle, a pseudo-micelle, or a micelle-like structure. In further or alternative embodiments, the form of the micellic assembly over the pH range of about 6.2 to 7.5 is a micelle.

In certain embodiments, provided herein is a micellic assembly in which at least one block of one or more of the membrane destabilizing block copolymers is a gradient block.

In some embodiments, provided herein is a micellic assembly that comprises at least one research reagent. In certain embodiments, a micellic assembly described herein comprises at least one diagnostic agent. In some embodiments, the micellic assembly comprises at least one therapeutic agent. In specific embodiments, the therapeutic agent is attached to the shell block of at least one of the membrane destabilizing block copolymers in the micellic assembly by a covalent bond, a non-covalent interaction, or a combination thereof. In some embodiments, a micellic assembly provided herein comprises a first therapeutic agent attached to the shell block of at least one of the membrane destabilizing block copolymers and at least one second therapeutic agent within the core portion of the micellic assembly. In some embodiments, each micellic assembly comprising on average 1-5, 5-250, 5-1000, 250-1000, at least 2, at least 5, at least 10, at least 20, or at least 50 therapeutic agents. In some embodiments, a therapeutic agent provided in the micellic assemblies described herein comprises at least one nucleotide, at least one carbohydrate or at least one amino acid. In certain embodiments, the therapeutic agent is a polynucleotide, an oligonucleotide, a gene expression modulator, a knockdown agent, an siRNA, an RNAi agent, a dicer substrate, an miRNA, an shRNA, an antisense oligonucleotide, or an aptamer. In some embodiments, the therapeutic agent is a proteinaceous therapeutic agent (e.g., a protein, peptide, enzyme, dominant-negative protein, hormone, antibody, antibody-like molecule, or antibody fragment). In certain embodiments, the therapeutic agent is a carbohydrate, or a small molecule with a molecular weight of greater than about 500 Daltons. In some embodiments, one or more of the plurality of membrane destabilizing block copolymers is attached to a therapeutic agent.

In some embodiments, the shell block of the membrane destabilizing block copolymers comprises at least one nucleotide, at least one carbohydrate, or at least one amino acid. In some embodiments, the shell block is non-peptidic. In certain embodiments, at least one nucleotide is a ribonucleotide. In some embodiments, at least one nucleotide is a gene expression modulator, a knockdown agent, an siRNA, an RNAi agent, a dicer substrate, an miRNA, an shRNA, an antisense oligonucleotide, or an aptamer. In specific embodiments, the knockdown agent is an siRNA, an antisense oligonucleotide, an miRNA, or an shRNA.

In some embodiments, provided herein is a micellic assembly that comprises at least one targeting moiety.

In certain embodiments, the shell block of the membrane destabilizing block copolymers is charged or chargeable. In some embodiments, the shell block of the membrane destabilizing block copolymers is polycationic at about neutral pH. In certain embodiments, the shell block comprises cationic and non-cationic monomeric units. In some embodiments, the shell block comprises at least one cationic chargeable monomeric unit and at least one non-chargeable monomeric unit.

In some embodiments, a micellic assembly provided herein comprises a plurality of membrane destabilizing block copolymers with a shell block that is a homopolymeric block. In further or alternative embodiments, a micellic assembly provided herein comprises a plurality of membrane destabilizing block copolymer with a shell block that is a heteropolymeric block. In some embodiments, the shell block of a membrane destabilizing block copolymer of a micellic assembly provided herein comprises a N,N-di(d-$C_1$-$C_6$)alkyl-amino($C_1$-$C_6$)alkyl-ethacrylate monomeric unit, a N,N-di($C_1$-$C_6$)alkyl-amino($C_1$-$C_6$)alkyl-methacrylate monomeric unit, a N,N-di($C_1$-$C_6$)alkyl-amino($C_1$-$C_6$)alkyl-acrylate monomeric unit, or a combination thereof.

In some embodiments, a micellic assembly provided herein comprises a core with at least one first chargeable species and at least one second chargeable species, wherein the first chargeable species is chargeable or charged to an anionic species, wherein the second chargeable species is chargeable or charged to a cationic species, and wherein the ratio of first chargeable species to second chargeable species present in the core is about 1:4 to about 4:1. In some embodiments, the ratio of positively charged groups to negatively charged groups in the core is about 1:4 to about 4:1 at about neutral pH. In certain embodiments, the ratio of positively charged groups to negatively charged groups in the core is about 1:2 to about 2:1 at about neutral pH. In some embodiments, the ratio of positively charged groups to negatively charged groups in the core is about 1:1.1 to about 1.1:1 at about neutral pH.

In some embodiments, the membrane destabilizing block copolymer comprises more than 5, more than 20, more than 50, or more than 100 chargeable species that are charged or chargeable to anionic species. In some embodiments, the membrane destabilizing block copolymer comprises more than 5, more than 20, more than 50, or more than 100 first chargeable species. In specific embodiments, each first chargeable species is chargeable or charged to an anionic species. In some embodiments, the membrane destabilizing block copolymer comprises more than 5, more than 20, more than 50, or more than 100 second chargeable species. In specific embodiments, each second chargeable species is charged or chargeable to a cationic species. In certain embodiments, the membrane destabilizing block copolymer comprises more than 5, more than 20, more than 50, or more than 100 hydrophobic species. In some embodiments, the core block of the membrane destabilizing block copolymer comprises more than 5, more than 20, more than 50, or more than 100 chargeable species that are charged or chargeable to anionic species. In certain embodiments, the core block of the membrane destabilizing block copolymer provided herein comprises more than 5, more than 20, more than 50, or more than 100 first chargeable species. In specific embodiments, each first chargeable species is chargeable or charged to an anionic species. In some embodiments, the core block of the membrane destabilizing block copolymer comprises more than 5, more than 20, more than 50, or more than 100 second chargeable species. In specific embodiments, each second chargeable species is charged or chargeable to a cationic species. In certain embodiments, the core block of the membrane destabilizing block copolymer provided herein comprises more than 5, more than 20, more than 50, or more than 100 hydrophobic species.

In some embodiments, a core block of at least one membrane destabilizing block copolymer comprises a first chargeable species (e.g., anionic chargeable) present on a first monomeric unit and the second chargeable species (e.g., cationic chargeable) on a second monomeric unit. In alternative embodiments, a first and second chargeable species are on the same monomeric unit (e.g., a zwitteroinically chargeable monomeric unit). In some embodiments, the ratio of the number of first monomeric units to the number of second monomeric units present in the core is about 1:4 to about 4:1.

In certain embodiments, a micellic assembly provided herein comprises at least one membrane destabilizing block copolymer with a core block that comprises at least one first chargeable monomeric unit and at least one second chargeable monomeric unit. In some embodiments, the first chargeable monomeric unit is Brønsted acid. In certain embodiments, at least 80% of the first chargeable monomeric unit is charged, by loss of a $H^+$, to an anionic species at a pH of about 7.4. In further or alternative embodiments, less than 50% of the first chargeable monomeric unit is charged to an anionic species at a pH of about 6. In some embodiments, the first chargeable monomeric unit is a $(C_2-C_8)$alkylacrylic acid. In certain embodiments, the second chargeable monomeric unit is a Brønsted base. In some embodiments, at least 40% of the second chargeable monomeric unit is charged, by gain of a $H^+$, to a cationic species at a pH of about 7.4. In certain embodiments, the second chargeable monomeric unit is N,N-di$(C_1-C_6)$alkyl-amino$(C_1-C_6)$alkyl-ethacrylate, N,N-di$(C_1-C_6)$alkyl-amino$(C_1-C_6)$alkyl-methacrylate, or N,N-di $(C_1-C_6)$alkyl-amino$(C_1-C_6)$alkyl-acrylate. In some embodiments, the core block further comprises at least one non-chargeable monomeric unit. In certain embodiments, the non-chargeable monomeric unit is a $(C_2-C_8)$alkyl-ethacrylate, a $(C_2-C_8)$alkyl-methacrylate, or a $(C_2-C_8)$alkyl-acrylate.

In some embodiments a micellic assembly provided herein is a particle with an average hydrodynamic diameter of about 10 nm to about 200 nm. In specific embodiments, the micellic assembly has an average hydrodynamic diameter of about 20 nm to about 100 nm. In more specific embodiments, the micellic assembly has an average hydrodynamic diameter of about 30 nm to about 80 nm.

In some embodiments, provided herein is a micellic assembly that is self-assembled. In certain embodiments, the micellic assembly self-assembles in an aqueous medium at a pH within about 6.5 to about 7.5. In some embodiments, the self-assembly occurs in less than 2 hours, in less than 1 hour, in less than 30 minutes, in less than 15 minutes. In some embodiments, the micellic assembly is membrane destabilizing in an aqueous medium at a pH within about 5.0 to about 7.4.

In certain embodiments, provided herein is a micellic assembly that comprises a greater net cationic charge at pH of about 5 than at a pH of about 7. In some embodiments, the absolute value of the charge of the micellic assembly is greater at pH of about 5 than at a pH of about 7.

In some embodiments, provided herein is a micellic assembly comprising a plurality of membrane destabilizing block copolymers having a core block and a shell block, wherein the ratio of the number average molecular weight of the core block to the number average molecular weight of the shell block is about 5:1 to about 1:1, or from 1:1 to about 5:1. In more specific embodiments, the ratio of the number average molecular weight of the core block to the number average molecular weight of the shell block is about 2:1.

In certain embodiments, the micellic assembly provided herein comprises a plurality of membrane destabilizing block copolymers with a core block having any suitable number average molecular weight (Mn), e.g., of greater than 2,000 dalton, of about 2,000 dalton to about 200,000 dalton, about 2,000 dalton to about 100,000 dalton, about 2,000 dalton to about 100,000 dalton, about 10,000 dalton to about 200,000 dalton, or about 10,000 dalton to about 100,000 dalton. In some embodiments, the micellic assembly provided herein comprises a plurality of membrane destabilizing block copolymers with a shell block having any suitable number average molecular weight (Mn), e.g., of greater than 5,000 dalton, or of about 5,000 dalton to about 50,000 dalton.

In some embodiments, the membrane destabilizing block copolymers provided herein have a polydispersity index of less than 2, less than 1.8, less than 1.6, less than 1.5, less than 1.4, or less than 1.3.

In some embodiments, provided herein is a micellic assembly that is stable at a pH of about 7.4. In certain embodiments, the micellic assembly is substantially less stable at a pH of about 5.8 than at a pH of about 7.4.

In certain embodiments, provided herein is a micellic assembly that is stable at a concentration of about 10 μg/mL, or greater (e.g., at about neutral pH). In some embodiments, provided herein is a micellic assembly that is stable at a concentration of about 100 μg/mL, or greater (e.g., at about neutral pH).

In certain embodiments described herein are any of the polymers that make up the micellic assemblies described herein. That is, the polymeric subunits (e.g., the block copolymers) or the individual polymers (whether or not in the form of a micellic assembly) are also embodiments described herein. To be explicit, each and every block copolymer that is presented herein is within the scope of the inventions described herein, both as an individual polymer, or as a polymeric unit/strand/component of the micellic assembly described herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A: An illustrative example of the composition and properties of RAFT synthesized polymers.

FIG. 1B: An illustrative example of the composition and properties of PEGMA-DMAEMA copolymers.

FIGS. 7A, 7B, and 7C: illustrative examples of the knock-down activity of siRNA-micelle complexes in cultured mammalian cells.

FIGS. 11A and 11B: illustrative examples of the effect of pH on polymer structure.

FIGS. 12A and 12B: illustrative summaries of knock-down data for siRNA— micelle complexes in cultured mammalian cells.

FIG. 14: An illustrative example of the synthesis of [PEGMA-MAA(NHS) J-[B-P-D].

FIGS. 15A, 15B, and 15C: illustrative examples of the RAFT Co-polymerization of PEGMA and MAA-NHS.

DETAILED DESCRIPTION OF THE INVENTION

Figure 2A:
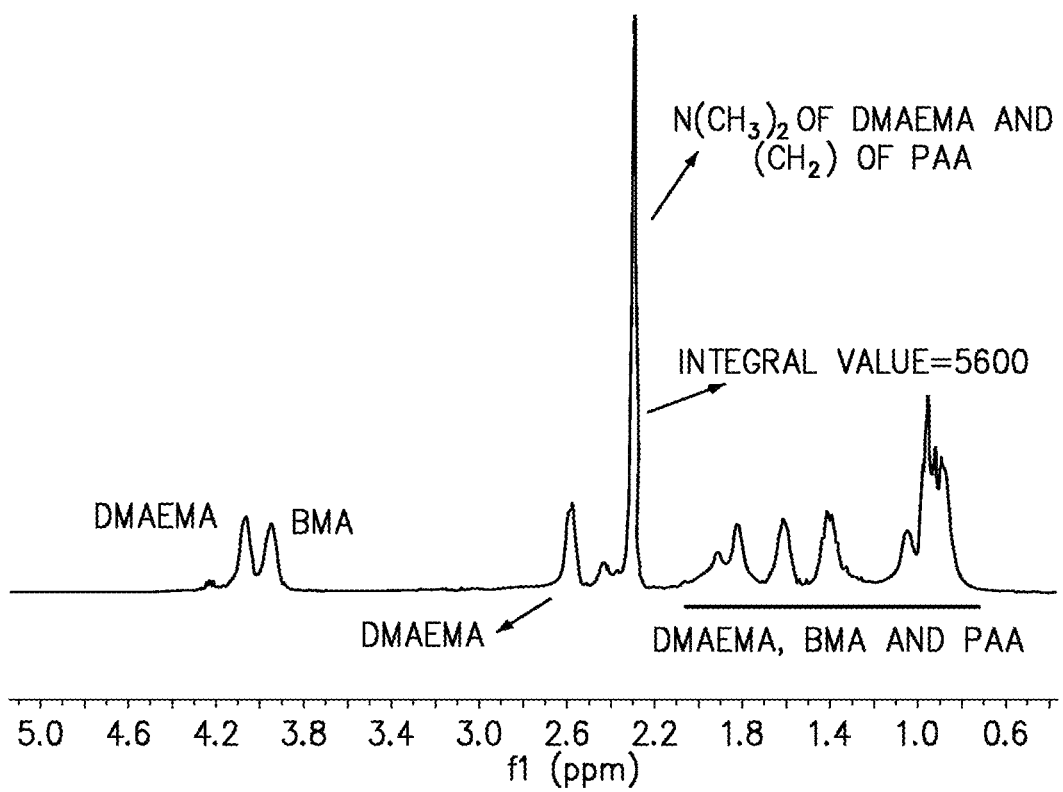
FIGS. 2A and 2B: illustrative examples of the NMR spectroscopy of block copolymer PRx0729v6.

Provided in certain embodiments herein are micellic assemblies and processes for making the same. In some embodiments, a micellic assembly provided herein comprises a plurality of block copolymers, the block copolymers comprising a shell block and a core block. In some embodiments, the micellic assembly comprising a core and a shell, wherein the core comprises a core block of the multiblock polymer, and wherein the shell comprises a shell block of the multiblock polymer. In some embodiments, the micellic assemblies described herein are self-assembled. In specific embodiments, the micellic assemblies are spontaneously self-assembled. In some embodiments, the micellic assembly is a micelle.

In certain embodiments, the core of the micellic assembly comprises a plurality of hydrophobic groups. In some embodiments, the hydrophobic groups are hydrophobic about at a neutral pH. In more specific embodiments, the hydrophobic group is hydrophobic at a slightly acidic pH (e.g., at a pH of about 6 and/or a pH of about 5). In certain embodiments, two or more different hydrophobic groups are present. In some embodiments, a hydrophobic group has a π value of about one, or more. A compound's π value is a measure of its relative hydrophilic-lipophilic value (see, e.g., Cates, L. A., "Calculation of Drug Solubilities by Pharmacy Students" Am. J. Pharm. Educ. 45:11-13 (1981)).

In some embodiments, the core of the micellic assembly comprises at least one charge at about a neutral pH (e.g., about 7.4). In specific embodiments, at least one charge is a negative charge. In a more specific embodiment, at least one charge is at least one negative charge and at least two positive charges.

In specific embodiments, the shell block is hydrophilic (e.g., at about a neutral pH). In some embodiments, the micellic assembly is disrupted or disassociated at a pH within about 4.7 to about 6.8.

In some instances, provided herein are micellic assemblies suitable for the delivery of therapeutic agents (including, e.g., oligonucleotides or peptides) to a living cell. In some embodiments, the micellic assemblies comprise a plurality of block copolymers and, optionally, at least one therapeutic agent. In certain embodiments, the micellic assemblies provided herein are biocompatible, stable (including chemically and/or physically stable), and/or reproducibly synthesized. Additionally, in some embodiments, the micellic assemblies provided herein are non-toxic (e.g., exhibit low toxicity), protect the therapeutic agent (e.g., oligonucleotide or peptide) payload from degradation, enter living cells via a naturally occurring process (e.g., by endocytosis), and/or deliver the therapeutic agent (e.g., oligonucleotide or peptide) payload into the cytoplasm of a living cell after being contacted with the cell. In certain instances, the polynucleotide (e.g., oligonucleotide) is an siRNA and/or another 'nucleotide-based' agent that alters the expression of at least one gene in the cell. Accordingly, in certain embodiments, the micellic assemblies provided herein are useful for delivering siRNA or peptide into a cell. In certain instances, the cell is in vitro, and in other instances, the cell is in vivo. In some embodiments, a therapeutically effective amount of the micellic assemblies comprising an siRNA or peptide is administered to an individual in need thereof (e.g., in need of having a gene knocked down, wherein the gene is capable of being knocked down by the siRNA administered). In specific instances, the micellic assemblies are useful for or are specifically designed for delivery of siRNA or peptide to specifically targeted cells of the individual.

Definitions

It is understood that, with regard to this application, use of the singular includes the plural and visa versa unless expressly stated to be otherwise. That is, "a" and "the" refer to one or more of whatever the word modifies. For example, "the polymer" or "a nucleotide" may refer to one polymer or nucleotide or to a plurality of polymers or nucleotides. By the same token, "polymers" and "nucleotides" would refer to one polymer or one nucleotide as well as to a plurality of polymers or nucleotides unless, again, it is expressly stated or obvious from the context that such is not intended.

As used herein, two moieties or compounds are "attached" if they are held together by any interaction including, by way of non-limiting example, one or more covalent bonds, one or more non-covalent interactions (e.g., ionic bonds, static forces, van der Waals interactions, combinations thereof, or the like), or a combination thereof.

Aliphatic or aliphatic group: the term "aliphatic" or "aliphatic group", as used herein, means a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms.

Anionic monomer: "Anionic monomer" or "anionic monomeric unit", as used herein, is a monomer or monomeric unit bearing a group that is present in an anionic charged state or in a non-charged state, but in the non-charged state is capable of becoming anionic charged, e.g., upon removal of an electrophile (e.g., a proton (H+), for example in a pH dependent manner). In certain instances, the group is substantially negatively charged at an approximately physiological pH but undergoes protonation and becomes substantially neutral at a weakly acidic pH. The non-limiting examples of such groups include carboxyl groups, barbituric acid and derivatives thereof, xanthine and derivatives thereof, boronic acids, phosphinic acids, phosphonic acids, sulfinic acids, phosphates, and sulfonamides.

Anionic species: "Anionic species", as used herein, is a group, residue or molecule that is present in an anionic charged or non-charged state, but in the non-charged state is capable of becoming anionic charged, e.g., upon removal of an electrophile (e.g., a proton (H+), for example in a pH dependent manner). In certain instances, the group, residue or molecule is substantially negatively charged at an approximately physiological pH but undergoes protonation and becomes substantially neutral at a weakly acidic pH.

Aryl or aryl group: as used herein, the term "aryl" or "aryl group" refers to monocyclic, bicyclic, and tricyclic ring systems having a total of five to fourteen ring members, wherein at least one ring in the system is aromatic and wherein each ring in the system contains three to seven ring members.

As used herein, a "charge neutralized" means a particle having a Zeta potential that is between ±10 to ±30 mV, and/or the presence of a first number (z) of chargeable species that are chargeable to a negative charge (e.g., acidic species that become anionic upon deprotonation) and a second number (0.5-z) of chargeable species that are chargeable to a positive charge (e.g., basic species that become cationic upon protonation).

As used herein, normal physiological pH refers to the pH of the predominant fluids of the mammalian body such as blood, serum, the cytosol of normal cells, etc. In certain instances, normal physiologic pH is about neutral pH, including, e.g., a pH of about 7.2 to about 7.4. In some instances, about neutral pH is a pH of 6.6 to 7.6. As used herein, the terms neutral pH, physiologic and physiological pH are synonymous and interchangeable.

As used herein, a micellic assembly is "disrupted" if it does not function in an identical, substantially similar or similar manner and/or possess identical, substantially similar or similar physical and/or chemical characteristics as would a stable micellic assembly. In "disruption" of a micellic assembly can be determined in any suitable manner. hi one instance, a micellic assembly is "disrupted" if it does not have a hydrodynamic particle size that is less than 5 times, 4 times, 3 times, 2 times, 1.8 times, 1.6 times, 1.5 times, 1.4 times, 1.3 times, 1.2 times, or 1.1 times the hydrodynamic particle size of a micellic assembly comprising the same block copolymers and as formed in an aqueous solution at a pH of 7.4, or formed in human serum. In one instance, a micellic assembly is "disrupted" if it does not have a concentration of assembly that is less than 5 times, 4 times, 3 times, 2 times, 1.8 times, 1.6 times, 1.5 times, 1.4 times, 1.3 times, 1.2 times, or 1.1 times the concentration of assembly of a micellic assembly comprising the same block copolymers and as formed in an aqueous solution at a pH of 7.4, or formed in human serum.

Heteroalkyl: the term "heteroalkyl" means an alkyl group wherein at least one of the backbone carbon atoms is replaced with a heteroatom.

Heteroaryl: the term "heteroaryl" means an aryl group wherein at least one of the ring members is a heteroatom.

As used herein, a "chargeable species", "chargeable group", or "chargeable monomeric unit" is a species, group or monomeric unit in either a charged or non-charged state. In certain instances, a "chargeable monomeric unit" is one that can be converted to a charged state (either an anionic or cationic charged state) by the addition or removal of an electrophile (e.g., a proton ($H^+$), for example in a pH dependent manner). The use of any of the terms "chargeable species", "chargeable group", or "chargeable monomeric unit" includes the disclosure of any other of a "chargeable species", "chargeable group", or "chargeable monomeric unit" unless otherwise stated. A "chargeable species" that is "charged or chargeable to an anion" or "charged or chargeable to an anionic species" is a species or group that is either in an anionic charged state or non-charged state, but in the non-charged state is capable of being converted to an anionic charged state, e.g., by the removal of an electrophile, such as a proton (H+). In specific embodiments, a chargeable species is a species that is charged to an anion at about neutral pH. It should be emphasized that not every chargeable species on a polymer will be anionic at a pH near the $pK_a$ (acid dissociation constant) of the chargeable species, but rather an equilibrium of anionic and non-anionic species will co-exist. A "chargeable species" that is "charged or chargeable to a cation" or "charged or chargeable to a cationic species" is a species or group that is either in an cationic charged state or non-charged state, but in the non-charged state is capable of being converted to a cationic charged state, e.g., by the addition of an electrophile, such as a proton (H+). In specific embodiments, a chargeable species is a species that is charged to an cation at about neutral pH. It should be emphasized that not every charged cationic species on a polymer will be cationic at a pH near the $pK_a$ (acid dissociation constant) of the charged cationic species, but rather an equilibrium of cationic and non-cationic species will co-exist. "Chargeable monomeric units" described herein are used interchangeably with "chargeable monomeric residues".

Heteroatom: the term "heteroatom" means an atom other than hydrogen or carbon, such as oxygen, sulfur, nitrogen, phosphorus, boron, arsenic, selenium or silicon atom.

Hydrophobic species: "hydrophobic species" (used interchangeably herein with "hydrophobicity-enhancing moiety"), as used herein, is a moiety such as a substituent, residue or a group which, when covalently attached to a molecule, such as a monomer or a polymer, increases the molecule's hydrophobicity or serves as a hydrophobicity enhancing moiety. The term "hydrophobicity" is a term of art describing a physical property of a compound measured by the free energy of transfer of the compound between a non-polar solvent and water (Hydrophobicity regained. Karplus P. A., *Protein Sci.,* 1997, 6: 1302-1307.) A compound's hydrophobicity can be measured by its logP value, the logarithm of a partition coefficient (P), which is defined as the ratio of concentrations of a compound in the two phases of a mixture of two immiscible solvents, e.g. octanol and water. Experimental methods of determination of hydrophobicity as well as methods of computer-assisted calculation of logP values are known to those skilled in the art. Hydrophobic species of the present invention include but are not limited to aliphatic, heteroaliphatic, aryl, and heteroaryl groups.

As used herein, a "hydrophobic core" comprises hydrophobic moieties. In certain instances, a "hydrophobic core" is substantially non-charged (e.g., the charge is substantially net neutral).

Inhibition: The terms "inhibition," "silencing," and "attenuation" as used herein refer to a measurable reduction in expression of a target inRNA or the corresponding protein as compared with the expression of the target mRNA or the corresponding protein in the absence of a knockdown agent. "Knockdown", or the reduction in expression of the target mRNA or the corresponding protein, can be assessed by measuring the mRNA levels using techniques well known in the art such as quantitative polymerase chain reaction (qPCR) amplification, RNA solution hybridization, nuclease protection, northern blotting and hybridization, and gene expression monitoring with a microarray; and in the case of proteins by techniques well known in the art such as SDS-PAGE, antibody binding, western blot analysis, immunoprecipitation, radioimmunoassay or enzyme-linked immunosorbent assay (ELISA), fluorescence activated cell analysis and immunocytochemistry.

Without being bound by theory not expressly recited in the claims, a membrane destabilizing polymer can directly or indirectly elicit a change (e.g., a permeability change) in a cellular membrane structure (e.g., an endosomal membrane) so as to permit an agent (e.g., polynucleotide), in association with or independent of a micellic assembly or micelle (or a constituent polymer thereof), to pass through such membrane structure—for example to enter a cell or to exit a cellular vesicle (e.g., an endosome). A membrane destabilizing polymer can be (but is not necessarily) a membrane disruptive polymer. A membrane disruptive polymer can directly or indirectly elicit lysis of a cellular vesicle or disruption of a cellular membrane (e.g., as observed for a substantial fraction of a population of cellular membranes).

Generally, membrane destabilizing or membrane disruptive properties of polymers or micelles can be assessed by various means. In one non-limiting approach, a change in a cellular membrane structure can be observed by assessment in assays that measure (directly or indirectly) release of an agent (e.g., polynucleotide) from cellular membranes (e.g., endosomal membranes)—for example, by determining the presence or absence of such agent, or an activity of such agent, in an environment external to such membrane. Another non-limiting approach involves measuring red blood cell lysis (hemolysis)—e.g., as a surrogate assay for a cellular membrane of interest. The assays are optionally done at a single pH value or at multiple pH values.

As used herein, a "micelle" includes a particle comprising a core and a hydrophilic shell, wherein the core is held together at least partially, predominantly or substantially through hydrophobic interactions. In certain instances, as used herein, a "micelle" is a multi-component, nanoparticle comprising at least two domains, the inner domain or core, and the outer domain or shell. The core is at least partially, predominantly or substantially held together by hydrophobic interactions, and is present in the center of the micelle. As used herein, the "shell of a micelle" is defined as non-core portion of the micelle.

As used herein, a particle or assembly is "micelle-like" if it substantially behaves like a micelle: (1) it is formed by spontaneous self association of block copolymers to form organized assemblies (e.g., micelles) upon dilution from a water-miscible solvent (such as but not limited to ethanol) to aqueous solvents (for example phosphate-buffered saline, pH 7.4); (2) it is stable to dilution (e.g., down to a polymer concentration of 100 ug/ml, 50 ug/ml, 10 ug/ml or 1 ug/ml, which constitutes the critical stability concentration or the critical micelle concentration (CMC)); (3) it is stable to high ionic strength of the surrounding media (e.g. 0.5M NaCl); and/or (4) it has an increasing instability as the concentration of organic solvent increases, such organic solvents including, but not limited to dimethylformamide (DMF), dimethylsulfoxide (DMS), and dioxane.

A "pH dependent membrane-destabilizing hydrophobe" is a group that is at least partially, predominantly, or substantially hydrophobic and is membrane destabilizing in a pH dependent manner. In certain instances, a pH dependent membrane destabilizing chargeable hydrophobe is a hydrophobic polymeric segment of a block copolymer and/or comprises a plurality of hydrophobic species; and comprises a plurality of anionic chargeable species. In some embodiments, the anionic chargeable species is anionic at about neutral pH. In further or alternative embodiments, the anionic chargeable species is non-charged at a lower, e.g., endosomal pH. In some embodiments, the membrane destabilizing chargeable hydrophobe comprises a plurality of cationic species. The pH dependent membrane-destabilizing chargeable hydrophobe comprises a non-peptidic and non-lipidic polymer backbone.

As used herein, a micellic assembly described herein is "stable" if the assembly does not disassociate or become destabilized. In certain instances, a stable micellic assembly is one that has a hydrodynamic particle size that is within approximately 60%, 50%, 40%, 30%, 20%, or 10% of the hydrodynamic particle size of a micellic assembly comprising the same block copolymers initially formed in an aqueous solution at a pH of 7.4 (e.g., a phosphate-buffered saline, pH 7.4). In some instances, a stable micellic assembly is one that has a concentration of formation/assembly that is within about 60%, 50%, 40%, 30%, 20%, or 10% of the concentration of formation/assembly of a micellic assembly comprising the same block copolymers initially in an aqueous solution at a pH of 7.4 (e.g., a phosphate-buffered saline, pH 7.4).

Nanoparticle: As used herein, the term "nanoparticle" refers to any particle having a diameter of less than 1000 nanometers (nm). In general, the nanoparticles should have dimensions small enough to allow their uptake by eukaryotic cells. Typically the nanoparticles have a longest straight dimension (e.g., diameter) of 200 nm or less. In some embodiments, the nanoparticles have a diameter of 100 nm or less. Smaller nanoparticles, e.g. having diameters of about 10 nm to about 200 nm, about 20 nm to about 100 nm, or 50 nm or less, e.g., 5 nm-30 nm, or 10 nm-30 nm, are used in some embodiments.

Nucleotide: As used herein, the term "nucleotide," in its broadest sense, refers to any compound and/or substance that is or can be incorporated into a polynucleotide (e.g., oligonucleotide) chain. In some embodiments, a nucleotide is a compound and/or substance that is or can be incorporated into a polynucleotide (e.g., oligonucleotide) chain via a phosphodiester linkage. In some embodiments, "nucleotide" refers to individual nucleic acid residues (e.g. nucleotides and/or nucleosides). In certain embodiments, "at least one nucleotide" refers to one or more nucleotides present; in various embodiments, the one or more nucleotides are discrete nucleotides, are non-covalently attached to one another, or are covalently attached to one another. As such, in certain instances, "at least one nucleotide" refers to one or more polynucleotide (e.g., oligonucleotide). In some embodiments, a polynucleotide is a polymer comprising two or more nucleotide monomeric units.

Oligonucleotide gene expression modulator: as used herein, an "oligonucleotide gene expression modulator" is an oligonucleotide agent capable of inducing a selective modulation of gene expression in a living cell by mechanisms including but not limited to an antisense mechanism or by way of an RNA interference (RNAi)-mediated pathway which may include (i) transcription inactivation; (ii) mRNA degradation or sequestration; (iii) transcriptional inhibition or attenuation or (iv) inhibition or attenuation of translation. Oligonucleotide gene expression modulators include, regulatory RNA (including virtually any regulatory RNA) such as, but not limited to, antisense oligonucleotides, miRNA, siRNA, RNAi, shRNA, aptamers and any analogs or precursors thereof.

Oligonucleotide knockdown agent: as used herein, an "oligonucleotide knockdown agent" is an oligonucleotide species which can inhibit gene expression by targeting and binding an intracellular nucleic acid in a sequence-specific manner. Non-limiting examples of oligonucleotide knockdown agents include siRNA, miRNA, shRNA, dicer substrates, antisense oligonucleotides, decoy DNA or RNA, antigene oligonucleotides and any analogs and precursors thereof.

As used herein, the term "oligonucleotide" refers to a polymer comprising 7-200 nucleotide monomeric units. In some embodiments, "oligonucleotide" encompasses single and or/double stranded RNA as well as single and/or double-stranded DNA. Furthermore, the terms "nucleotide", "nucleic acid," "DNA," "RNA," and/or similar terms include nucleic acid analogs, i.e. analogs having a modified backbone, including but not limited to peptide nucleic acids (PNA), locked nucleic acids (LNA), phosphono-PNA, morpholino nucleic acids, or nucleic acids with modified phosphate groups (e.g., phosphorothioates, phosphonates, 5'-N-phosphoramidite linkages). Nucleotides can be purified from natural sources, produced using recombinant expression systems and optionally purified, chemically synthesized, etc. As used herein, a "nucleoside" is the term describing a compound comprising a monosaccharide and a base. The monosaccharide includes but is not limited to pentose and hexose monosaccharides. The monosaccharide also includes monosaccharide mimetics and monosaccharides modified by substituting hydroxyl groups with halogens, methoxy, hydrogen or amino groups, or by esterification of additional hydroxyl groups. In some embodiments, a nucleotide is or comprises a natural nucleoside phosphate (e.g. adenosine, thymidine, guanosine, cytidine, uridine, deoxy adenosine, deoxythymidine, deoxyguanosine, and deoxycytidine phosphate). In some embodiments, the base includes any bases occurring naturally in various nucleic acids as well as other modifications which mimic or resemble such naturally occurring bases. Nonlimiting examples of modified or derivatized bases include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxy acetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, 2-aminoadenine, pyrrolopyrimidine, and 2,6-diaminopurine. Nucleoside bases also include universal nucleobases such as difluorotolyl, nitroindolyl, nitropyrrolyl, or nitroimidazolyl. Nucleotides also include nucleotides which harbor a label or contain abasic, i.e. lacking a base, monomers. A nucleic acid sequence is presented in the 5' to 3' direction unless otherwise indicated. A nucleotide can bind to another nucleotide in a sequence-specific manner through hydrogen bonding via Watson-Crick base pairs. Such base pairs are said to be complementary to one another. An oligonucleotide can be single stranded, double-stranded or triple-stranded.

RNA interference (RNAi): As used herein, the term "RNA interference" or "RNAi" refers to sequence-specific inhibition of gene expression and/or reduction in target mRNA and protein levels mediated by an at least partially double-stranded RNA, which also comprises a portion that is substantially complementary to a target RNA.

RNAi agent: As used herein, the term "RNAi agent" refers to an oligonucleotide which can mediate inhibition of gene expression through an RNAi mechanism and includes but is not limited to siRNA, microRNA (miRNA), short hairpin RNA (shRNA), asymmetrical interfering RNA (aiRNA), dicer substrate and the precursors thereof.

Short interfering RNA (siRNA): As used herein, the term "short interfering RNA" or "siRNA" refers to an RNAi agent comprising a nucleotide duplex that is approximately 15-50 base pairs in length and optionally further comprises zero to two single-stranded overhangs. One strand of the siRNA includes a portion that hybridizes with a target RNA in a complementary manner. In some embodiments, one or more mismatches between the siRNA and the targeted portion of the target RNA may exist. In some embodiments, siRNAs mediate inhibition of gene expression by causing degradation of target transcripts.

Short hairpin RNA (shRNA): Short hairpin RNA (shRNA) refers to an oligonucleotide having at least two complementary portions hybridized or capable of hybridizing with each other to form a double-stranded (duplex) structure and at least one single-stranded portion.

Dicer Substrate: a "dicer substrate" is a greater than approximately 25 base pair duplex RNA that is a substrate for the RNase III family member Dicer in cells. Dicer substrates are cleaved to produce approximately 21 base pair duplex small interfering RNAs (siRNAs) that evoke an RNA interference effect resulting in gene silencing by mRNA knockdown.

Inhibit gene expression: As used herein, the phrase "inhibit gene expression" means to cause any measurable reduction in the amount of an expression product of the gene. The expression product can be an RNA transcribed from the gene (e.g. an mRNA) and/or a polypeptide translated from an mRNA transcribed from the gene. The level of expression may be determined using standard techniques for measuring mRNA or protein.

As used herein, a "substantially non-charged" includes a Zeta potential that is between ±10 to ±30 mV, and/or the presence of a first number (z) of chargeable species that are chargeable to a negative charge (e.g., acidic species that become anionic upon deprotonation) and a second number (0.5-z) of chargeable species that are chargeable to a positive charge (e.g., basic species that become cationic upon protonation).

Therapeutic agent: As used herein, the phrase "therapeutic agent" refers to any agent that, when administered to a subject, organ, tissue, or cell has a therapeutic effect and/or elicits a desired biological and/or pharmacological effect.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition.

Micellic Assembly Structure

Provided in some embodiments herein is a micellic assembly comprising a plurality of membrane destabilizing block copolymers. In certain embodiments, the micellic assembly comprises a core and a shell.

In some embodiments, the core blocks of the membrane destabilizing block copolymers are membrane destabilizing. In specific embodiments, the core block of the membrane destabilizing block copolymers described herein is a pH dependent membrane destabilizing hydrophobe. In certain embodiments, the shell block is hydrophilic. In specific embodiments, the shell block is hydrophilic at about a neutral pH.

As used herein, membrane-destabilizing block copolymers include membrane-disruptive block copolymers (e.g., polymers that lyse an endosomal membrane) and block copolymers that locally destabilize a membrane (e.g., via a temporary rift in an endosomal membrane). In some embodiments, a membrane-destabilizing block copolymer comprises (i) a plurality of hydrophobic monomeric residues, (ii) a plurality of anionic monomeric residues having a chargeable species, the chargeable species being anionic at serum physiological pH, and being substantially neutral or non-charged at an endosomal pH and (iii) optionally a plurality of cationic monomeric residues. In some embodiments, modification of the ratio of anionic to cationic species in a block copolymer allows for modification of membrane destabilizing activity of a micellic assembly described herein. In some of such embodiments, the ratio of anionic: cationic species in a block copolymer ranges from about 4:1 to about 1:4 at serum physiological pH. In some of such embodiments, modification of the ratio of anionic to cationic species in a hydrophobic block of a block copolymer allows for modification of membrane destabilizing activity of a micellic assembly described herein. In some of such embodiments, the ratio of anionic: cationic species in a hydrophobic block of a block copolymer described herein ranges from about 1:2 to about 3:1, or from about 1:1 to about 2:1 at serum physiological pH.

In certain embodiments, the membrane destabilizing block copolymers present in a micellic assembly provided herein comprise a core section (e.g., core block) that comprises a plurality of hydrophobic groups. In more specific embodiments, the core section (e.g., core block) comprises a plurality of hydrophobic groups and a plurality of first chargeable species or groups. In still more specific embodiments, such first chargeable species or groups are negatively charged and/or are chargeable to a negatively charged species or group (e.g., at about a neutral pH, or a pH of about 7.4). In some specific embodiments, the core section (e.g., core block) comprises a plurality of hydrophobic groups, a plurality of first chargeable species or groups, and a plurality of second chargeable species or groups. In more specific embodiments, the first chargeable species or groups are negatively charged and/or are chargeable to a negatively charged species or group, and the second chargeable species or groups are positively charged and/or are chargeable to a positively charged species or group (e.g., at about a neutral pH, or a pH of about 7.4).

In certain embodiments, the shell of the micellic assembly and/or the shell blocks of the membrane destabilizing block copolymers described herein also comprise a chargeable species or groups. In some embodiments, one or more of the membrane destabilizing block copolymers present in a micellic assembly provided herein has a shell section that comprises a plurality of cationically chargeable species or groups. Depending on the concentration of electrolytes in a medium surrounding the micellic assembly (e.g., on the pH), these cationically chargeable species are in either in a cationically charged, or in a non-charged state.

In certain embodiments, a micellic assembly provided herein has a net cationic charge at a pH of about 5. In some embodiments, a micellic assembly described herein has a net neutral charge at about a neutral pH. In certain embodiments, a micellic assembly described herein has a net cationic charge at about neutral pH (e.g., at a pH of about 7.4). In some embodiments, a micellic assembly described herein has a greater net cationic charge at pH of about 5 than at a pH of about 7. In further or alternative embodiments, a micellic assembly provided herein has a nominal (or absolute value of) charge that is greater at pH of about 5 than at a pH of about 7.

In certain embodiments, provided herein is a micellic assembly wherein the form of the micellic assembly is a micelle, a pseudo-micelle, or a micelle-like structure over the pH range of about 6 and up, about 6.5 and up, about 7 and up, about 6 to about 14, or more; about 6 to about 10, or more; about 6 to about 9.5, or more; about 6 to about 9, or more; about 6 to about 8.5, or more; about 6 to about 8, or more; about 6.5 to about 14, or more; about 6.5 to about 10, or more; about 6.5 to about 9.5, or more; about 6.5 to about 9, or more; about 6.5 to about 8.5, or more; about 7 to about 14, or more; about 7 to about 10, or more; about 7 to about 9.5, or more; about 7 to about 9, or more; about 7 to about 8.5, or more; about 6.2 to about 7.5, or more; 6.2 to 7.5; or about 7.2 to about 7.4. In certain embodiments, at a pH of about 7, or below; about 6.8, or below; about 6.5, or below; about 6.2, or below; about 6, or below; about 5.8, or below; or about 5.7, or below, the micellic assembly, micelle, pseudo-micelle, or micelle-like structure provided herein become substantially, or at least partially disrupted or disassociated. In specific embodiments, the form of the micellic assembly over the pH range of about 6.2 to 7.5 is a micelle. It is to be understood that as used herein, the micellic assemblies have a form over at least the pH described and may also have the described form at a pH outside the pH range described.

In certain embodiments, the "block copolymers" described herein comprise a core section and a shell section. As discussed herein, the core section optionally is or comprises a core block and the shell section optionally comprises or is a shell block. In some embodiments, at least one of such blocks is a gradient polymer block. In further embodiments, the block copolymer utilized herein is optionally substituted with a gradient polymer (i.e., the polymer utilized in the micellic assembly is a gradient polymer having a core section and a shell section).

In certain embodiments, the micellic assembly is a nanoparticle. In specific embodiments, the micellic assembly is a micelle. In yet further embodiments, the micellic assembly is a nanoparticle or micelle with the size of approximately 10 nm to about 200 nm, about 10 nm to about 100 nm, or about 30-80 nm. Particle size can be determined in any manner, including, but not limited to, by gel permeation chromatography (GPC), dynamic light scattering (DLS), electron microscopy techniques (e.g., TEM), and other methods.

In certain embodiments, the shell and/or shell block is hydrophilic and/or charged (e.g., non-charged, cationic, polycationic, anionic, polyanionic, or zwitterionic). In certain embodiments, the shell and/or shell block is hydrophilic and neutral (non-charged). In specific embodiments, the shell and/or shell block comprises a net positive charge. In specific embodiments, the shell and/or shell block comprises a net negative charge. In specific embodiments, the shell and/or shell block comprises a net neutral charge. In some embodiments, the core and/or core block is hydrophobic and/or comprises hydrophobic groups, moieties, monomeric units, species, or the like. In specific embodiments, the hydrophobic core and/or core block comprise a plurality of hydrophobic groups, moieties, monomeric units, species, or the like and a plurality of chargeable species or monomeric units. In more specific embodiments, the plurality of chargeable monomeric units or species comprises a plurality of anionic chargeable monomeric units or species. In more specific embodiments, the plurality of chargeable monomeric units or species comprises a plurality of cationic chargeable monomeric units or species. In still more specific embodiments, the plurality of chargeable monomeric units or species comprises a plurality of cationic and a plurality of anionic chargeable monomeric units or species. In some embodiments, the block copolymers each have (1) a hydrophilic, charged block (e.g., anionic or polyanionic; or cationic or polycationic; or zwitterionic; or non-charged) forming the shell of the micellic assemblies (e.g., micelle), (2) a hydrophobic block, and (3) a plurality of anionic chargeable species, and are membrane destabilizing (e.g., become membrane destabilizing in a pH dependent manner). In some embodiments, the plurality of anionic chargeable species is present in the hydrophobic block. In certain embodiments, the hydrophobic core and/or core block optionally comprise spacer monomeric units which may or may not comprise hydrophobic groups, chargeable groups, or a combination thereof. In some embodiments, a polymer block forming or present in the core of the micellic assemblies (e.g., micelle) (e.g., one or more core block of the copolymer) is chargeable (e.g., contains cationic and/or anionic species at a physiological pH). In some instances, the micellic assemblies (e.g., micelles) provided herein are formed from a plurality of block copolymers which self-associate. In certain instances, the self-association occurs through the interactions of the hydrophobic blocks of the block copolymers and the resulting micellic assemblies (e.g., micelles) are stabilized through hydrophobic interactions of the hydrophobic blocks present in the core of the micellic assemblies.

In some embodiments, the micellic assemblies (e.g., micelles) provided herein retain activity (e.g., the activity of the micellic assembly to deliver a therapeutic agent, e.g., a polynucleotide) in 50% human serum for at least 2 hours, at least 4 hours, at least 6 hours, at least 8 hours, at least 12 hours, or at least 24 hours. In further or alternative embodiments, the micellic assemblies (e.g., micelles) provided herein retain activity (e.g., the activity of the micellic assembly to deliver a polynucleotide) in at least 50% human plasma for at least 2 hours, at least 4 hours, at least 6 hours, at least 8 hours, at least 12 hours, or at least 24 hours. In further or alternative embodiments, the micellic assemblies (e.g., micelles) provided herein retain activity (e.g., the activity of the micellic assembly to deliver a polynucleotide) in 50% mouse serum for at least 2 hours, at least 4 hours, at least 6 hours, at least 8 hours, at least 12 hours, or at least 24 hours. In still further or alternative embodiments, the micellic assemblies (e.g., micelles) provided herein retain activity (e.g., the activity of the micellic assembly to deliver a therapeutic agent, e.g., a polynucleotide) in at least 50% mouse plasma for at least 2 hours, at least 4 hours, at least 6 hours, at least 8 hours, at least 12 hours, or at least 24 hours. In specific embodiments, the micellic assemblies (e.g., micelles) provided herein retain activity (e.g., the activity of the micellic assembly to deliver a therapeutic agent, e.g., a polynucleotide) in 50% human serum for at least 2 hours, in at least 50% human plasma for at least 2 hours, in 50% mouse serum for at least 2 hours, in at least 50% mouse plasma for at least 2 hours, or a combination thereof.

In various embodiments, block copolymers utilized in the micellic assemblies (e.g., micelles) described herein have or are selected to have an influence on a certain aspect or functionality of the micellic assemblies (e.g., micelles) provided herein, including but not limited to: (1) the biophysical properties of the micellic assembly (e.g., micelle) such as, by way of non-limiting example, solubility, aqueous solubility, stability, stability in an aqueous medium, hydrophilicity, lipophilicity, hydrophobicity, or the like; (2) the facilitation of the formulation of the micellic assembly into an administrable form, or other purposes; (3) the ability of the micellic assembly to target a specific or selected type of cell (e.g., by carrying a targeting moiety); and/or (4) the ability to increase biocompatibility of the micellic assemblies (e.g., micelles). In some embodiments, a micellic assembly (e.g., micelle) provided herein is characterized by one or more of the following: (1) the micellic assembly (e.g., micelle) is formed by spontaneous self association of block copolymers to form organized assemblies (e.g., micelles) upon dilution from a water-miscible solvent (such as but not limited to ethanol) to aqueous solvents (for example phosphate-buffered saline, pH 7.4); (2) the micellic assembly (e.g., micelle) is stable to dilution (e.g., down to a polymer concentration of 100 ug/ml, 50 ug/ml, 10m/ml, 5 ug/ml or 1 ug/ml, which constitutes the critical stability concentration or the critical micelle concentration (CMC)); (3) the micellic assembly (e.g., micelle) is stable to high ionic strength of the surrounding media (e.g. 0.5M NaCl); and/or (4) the micellic assembly (e.g., micelle) has an increasing instability as the concentration of organic solvent increases, such organic solvents including, but not limited to dimethylformamide (DMF), dimethylsulfoxide (DMS), and dioxane. In some embodiments, a micellic assembly (e.g., micelle) provided herein is characterized by having at least two of the aforementioned properties. In some embodiments, a micellic assembly (e.g., micelle) provided herein is characterized by having at least three of the aforementioned properties. In some embodiments, a micellic assembly (e.g., micelle) provided herein is characterized by having all of the aforementioned properties.

In certain embodiments, micellic assemblies (e.g., micelles) provided herein are further or alternatively characterized by other criteria: (1) the molecular weight of the individual blocks and their relative length ratios is decreased or increased in order to govern the size of the micellic assembly formed and its relative stability and (2) the size of the polymer cationic block that forms the shell is varied in order to provide effective complex formation with and/or charge neutralization of an anionic therapeutic agent (e.g., an oligonucleotide drug).

Moreover, in certain embodiments, micellic assemblies provided herein selectively uptake small hydrophobic molecules, such as hydrophobic small molecule compounds (e.g., hydrophobic small molecule drugs) into the hydrophobic core of the micellic assemblies. In specific embodiments, micellic assemblies provided herein selectively uptake small hydrophobic molecules, such as the hydrophobic small molecule compound pyrene into the hydrophobic core of a micellic assembly.

Core

Provided in certain embodiments herein, the core of a micellic assembly described herein comprises a plurality of pH dependent membrane destabilizing hydrophobes. In certain embodiments, the core of a micellic assembly described herein is held together at least partially, substantially, or predominantly by hydrophobic interactions.

In some embodiments, the core of a micellic assembly described herein comprises a plurality of first chargeable species. In specific embodiments, the first chargeable species are charged or chargeable to an anionic species. It is to be understood that none, some, or all of the first chargeable species within the core are charged.

In certain embodiments, the core block of a membrane destabilizing polymer described herein comprises a plurality of first chargeable species, and a plurality of second chargeable species. In some instances, the first chargeable species is charged or chargeable to an anionic species; and the second chargeable species is charged or chargeable to a cationic species. In some embodiments, the core of a micellic assembly described herein comprises a plurality of first chargeable species; a plurality of second chargeable species; and a plurality of hydrophobic species.

In certain embodiments, where the core comprises a plurality of anionic chargeable species and a plurality of cationic chargeable species, the ratio of the number of the plurality of anionic chargeable species to the number of the plurality of cationic chargeable species is about 1:10 to about 10:1, about 1:8 to about 8:1, about 1:6 to about 6:1, about 1:4 to about 4:1, about 1:2 to about 2:1, about 3:2 to about 2:3, or is about 1:1. In some embodiments, the core comprises a plurality of anionic chargeable species that are anionically charged and a plurality of cationically chargeable species that is cationically charged, wherein the ratio of the number of anionically charged species to the number of cationically charged species present in the core is about 1:10 to about 10:1, about 1:8 to about 8:1, about 1:6 to about 6:1, about 1:4 to about 4:1, about 1:2 to about 2:1, about 3:2 to about 2:3, or is about 1:1.

In some embodiments, the ratio, at about a neutral pH (e.g., at a pH of about 7.4), of the number of the plurality of anionic chargeable species to the number of the plurality of cationic chargeable species is about 1:10 to about 10:1, about 1:8 to about 8:1, about 1:6 to about 6:1, about 1:4 to about 4:1, about 1:2 to about 2:1, about 2:3 to about 3:2, about 1:1.1 to about 1.1:1, or is about 1:1. In some embodiments, the core comprises a plurality of anionic chargeable species that is anionically charged and a plurality of cationically chargeable species that is cationically charged, wherein the ratio, at about a neutral pH (e.g., at a pH of about 7.4), of the number of anionically charged species to the number of cationically charged species present in the core is about 1:10 to about 10:1, about 1:8 to about 8:1, about 1:6 to about 6:1, about 1:4 to about 4:1, about 1:2 to about 2:1, about 2:3 to about 3:2, about 1:1.1 to about 1.1:1, or is about 1:1. In specific embodiments, the ratio of positively charged species present in the core to negatively charged species in the core is about 1:4 to about 4:1 at about neutral pH. In more specific embodiments, the ratio of positively charged species present in the core to negatively charged species in the core is about 1:2 to about 2:1 at about neutral pH. In specific embodiments, the ratio of positively charged species present in the core to negatively charged species in the core is about 1:1.1 to about 1.1:1 at about neutral pH.

In specific embodiments, the first chargeable species is Brønsted acid. In certain instances, as used herein, a chargeable species includes species wherein addition or removal of a proton (e.g., in a pH dependent manner), provides a cationic or anionic, respectively, species, group, or monomeric unit.

In some embodiments, the first chargeable species present in the core are species that are at least 50%, at least 60%, at least 70%, at least 80%, at least 85%, or at least 95% negatively charged at about neutral pH (e.g., at a pH of about 7.4). In specific embodiments, these first chargeable species are charged by loss of a $H^+$, to an anionic species at about neutral pH. In further or alternative embodiments, the first chargeable species present in the core are species that are at least 20%, at least 30%, at least 40%, at least 50%, at least 60%, at least 70%, at least 80%, at least 85%, or at least 95% neutral or non-charged at a slightly acidic pH (e.g., a pH of about 6.5, or less; about 6.2, or less; about 6, or less; about 5.9, or less; about 5.8, or less; or about endosomal pH).

In some embodiments, the first chargeable species is, by way of non-limiting example, a carboxylic acid, anhydride, sulfonamide, sulfonic acid, sulfinic acid, sulfuric acid, phosphoric acid, phosphinic acid, boric acid, phosphorous acid, or the like.

In some embodiments, the second chargeable species present in the core are species that are at least 20%, at least 30%, at least 40%, at least 50%, at least 60%, at least 70%, at least 80%, at least 85%, or at least 95% positively charged at about neutral pH (e.g., at a pH of about 7.4). In specific embodiments, these second chargeable species are charged by addition of an $H^+$, to a cationic species. In further or alternative embodiments, the second chargeable species present in the core are species that are at least 20%, at least 30%, at least 40%, at least 50%, at least 60%, at least 70%, at least 80%, at least 85%, or at least 95% positively charged at a slightly acidic pH (e.g., a pH of about 6.5, or less; about 6.2, or less; about 6, or less; about 5.9, or less; about 5.8, or less; or about endosomal pH).

In some embodiments provided herein is a micellic assembly comprising a plurality of membrane destabilizing moieties in the core of the micellic assembly.

Shell

In some embodiments, the shell of a micellic assembly described herein is hydrophilic. In specific embodiments, the shell of a micellic assembly described herein comprises a plurality of chargeable species. In specific embodiments, the chargeable species is charged or chargeable to a cationic species. In other specific embodiments, the chargeable species is charged or chargeable to an anionic species. In other embodiments, the shell of the micellic assembly is hydrophilic and non-charged (e.g., substantially non-charged). It is to be understood that such shell blocks include species wherein none, some, or all of the chargeable species are charged.

In specific embodiments, the shell of a micellic assembly described herein is polycationic at about neutral pH (e.g., at a pH of about 7.4). In some embodiments, the chargeable species in the shell of a micellic assembly are species, groups, or monomeric units that are at least 20%, at least 30%, at least 40%, at least 50%, at least 60%, at least 70%, at least 80%, at least 85%, or at least 95% positively charged at about neutral pH (e.g., at a pH of about 7.4). In specific embodiments, these chargeable species in the shell of a micellic assembly are charged by addition of an $H^+$, to a cationic species (e.g., a Brønsted base). In further or alternative embodiments, the chargeable species in the shell of a micellic assembly described herein are species that are at least 20%, at least 30%, at least 40%, at least 50%, at least 60%, at least 70%, at least 80%, at least 85%, or at least 95% positively charged at a slightly acidic pH (e.g., a pH of about 6.5, or less; about 6.2, or less; about 6, or less; about 5.9, or less; about 5.8, or less; or about endosomal pH).

In some embodiments, the shell of a micellic assembly described herein is cationic at or near physiological pH (e.g., the pH of circulating human plasma). In some embodiments, the shell block is polycationic. In some embodiments, the shell comprises one or more therapeutic agents (e.g., a polynucleotide, such as siRNA), wherein the therapeutic agents are polyanionic. In some embodiments, the plurality of therapeutic agents comprise a total of x anions, and the polycationic shell of a micellic assembly described herein comprises about 0.6 x, about 0.7 x, about 0.8 x, about 0.9 x, about 1.0 x, about 1.1 x cations, or more.

In some embodiments, the shell of a micellic assembly described herein is hydrophilic and non-charged. Hydrophilic, non-charged species useful herein include, by way of non-limiting example, polyethylene glycol (PEG), polyethylene oxide (PEO), or the like.

In certain embodiments, the shell of a micellic assembly described herein comprises a plurality of different hydrophilic species (e.g., at least one non-charged hydrophilic species and at least one charged hydrophilic species).

Particle Size

In certain embodiments, the micellic assembly provided herein is a nanoparticle having any suitable size. Size of the nanoparticles is adjusted to meet specific needs by adjusting the degree of polymerization of the core sections, shell sections, additional sections, or a combination thereof. In specific embodiments, a micellic assembly provided herein has an average hydrodynamic diameter of about 10 nm to about 200 nm. In more specific embodiments, the micellic assembly provided herein has an average hydrodynamic diameter of about 1 nm to about 500 nm, about 5 nm to about 250 nm, about 10 nm to about 200 nm, about 10 nm to about 100 nm, about 20 nm to about 100 nm, about 30 nm to about 80 nm, or the like in an aqueous medium. In still more specific embodiments, a micellic assembly provided herein has an average hydrodynamic diameter of about 1 nm to about 500 nm, about 5 nm to about 250 nm, about 10 nm to about 200 nm, about 10 nm to about 100 nm, about 20 nm to about 100 nm, about 30 nm to about 80 nm, or the like in an aqueous medium with about a neutral pH (e.g., a pH of about 7.4). In some embodiments, a micellic assembly provided herein has an average hydrodynamic diameter of about 1 nm to about 500 nm, about 5 nm to about 250 nm, about 10 nm to about 200 nm, about 10 nm to about 100 nm, about 20 nm to about 100 nm, about 30 nm to about 80 nm, or the like in human serum. In specific embodiments, provided herein is a micellic assembly that has a particle size of about 10 nm to about 200 nm in both an aqueous medium having a pH of about 7.4 and in human serum.

Assembly

In some embodiments, a micellic assembly provided herein is self-assembled. In certain embodiments, the micellic assembly is self-assembled or is capable of being self-assembled in an aqueous medium. In some embodiments, the micellic assembly is self-assembled or is capable of being self-assembled in an aqueous medium having about neutral pH (e.g., having a pH of about 7.4). In some embodiments, the micellic assembly is self-assembled or is capable of being self-assembled upon dilution of an organic solution of the block copolymers with an aqueous medium having about neutral pH (e.g., having a pH of about 7.4). In some embodiments, the micellic assembly is self-assembled or is capable of being self-assembled in human serum. In some embodiments, a micellic assembly provided herein is self-assembled.

In specific embodiments, a micellic assembly provided herein self-assembles in an aqueous medium at least one pH value within about 6 to about 9, about 6 to about 8, about 6.5 to about 9, about 6.5 to about 8, about 6.5 to about 7.5, about 7 to about 9, or about 7 to about 8. In some embodiments, a micellic assembly is membrane destabilizing in an aqueous medium at a pH value within about 5.0 to about 7.4. It is to be understood that as used herein, the micellic assemblies self assemble at least the pH described herein, but may also self assemble at one or more pH values outside the pH range described.

In some embodiments, a micellic assembly provided herein self-assembles at any suitable concentration. In certain embodiments, a micellic assembly provided herein self-assembles (e.g., has a critical assembly concentration (CAC), or the minimum concentration at which a micellic assembly forms) of about 2 µg/mL, about 5 µg/mL, about 8 µg/mL, about 10 µg/mL, about 20 µg/mL, about 25 µg/mL, about 30 µg/mL, about 40 µg/mL, about 50 µg/mL, about 60 µg/mL, about 70 µg/mL, about 80 µg/mL, about 90 µg/mL, about 100 µg/mL, or greater. In certain embodiments, a micellic assembly provided herein self assembles at least one concentration between about 1 µg/mL and about 100 µg/mL.

In some embodiments, the micellic assembly (e.g., micelles) provided herein are prepared by spontaneous self-assembly of the polymers described herein. In certain embodiments, the polymers described herein assemble into the micellic assemblies provided herein upon (a) dilution of a solution of the polymer in water-miscible organic solvent into aqueous media; or (b) being dissolved directly in an aqueous solution. In some embodiments, the polymers described herein assemble into the micellic assemblies provided herein in the absence of polynucleotides.

In some embodiments, the micellic assemblies (e.g., micelles) are stable to dilution in an aqueous solution. In specific embodiments, the micellic assemblies (e.g., micelles) are stable to dilution at physiologic pH (including the pH of circulating blood in a human) with a critical stability concentration (e.g., a critical micelle concentration (CMC)) of approximately 50 to approximately 100 µg/mL, or approximately 10 to approximately 50 µg/mL, less than 10 µg/mL, less than 5 µg/mL, or less than 2 µg/mL. As used herein, "destabilization of a micellic assembly" means that the polymeric chains forming a micellic assembly at least partially disaggregate, structurally alter (e.g., expand in size and/or change shape), and/or may form amorphous supramolecular structures (e.g., non-micellic supramolecular structures). The terms critical stability concentration (CSC), critical micelle concentration (CMC), and critical assembly concentration (CAC) are used interchangeably herein.

Stability

In some embodiments, a micellic assembly provided herein is stable in an aqueous medium. In certain embodiments, a micellic assembly provided herein is stable in an aqueous medium at a selected pH, e.g., about physiological pH (e.g., the pH of circulating human plasma). In specific embodiments, a micellic assembly provided herein is stable at about a neutral pH (e.g., at a pH of about 7.4) in an aqueous medium. In specific embodiments, the aqueous medium is animal (e.g., human) serum or animal (e.g., human) plasma. In certain embodiments, a micellic assembly provided herein is stable in human serum and/or human plasma. In specific embodiments, the micellic assembly is stable in circulating human plasma. It is to be understood that stability of the micellic assembly is not limited to designated pH, but that it is stable at pH values that include, at a minimum, the designated pH. In specific embodiments, a micellic assembly described herein is substantially less stable at an acidic pH than at a pH that is about neutral. In more specific embodiments, a micellic assembly described herein is substantially less stable at a pH of about 5.8 than at a pH of about 7.4.

In specific embodiments, the micellic assembly is stable at a concentration of about 10 µg/mL, or greater (e.g., at about a neutral pH). In some embodiments, the micellic assembly is stable at a concentration of about 100 µg/mL, or greater (e.g., at about a neutral pH).

Block Copolymers

In some embodiments, membrane destabilizing block copolymers provided herein are membrane destabilizing at any suitable pH. In some embodiments, the membrane destabilizing block copolymers are membrane destabilizing (e.g., in an aqueous medium) at an endosomal pH, a pH of about 6.5, or lower, about 5.0 to about 6.5, or about 6.2, or lower.

In specific embodiments, the core block of the membrane destabilizing block copolymers provided herein comprise a plurality of first chargeable groups, species, or monomeric units and a plurality of second chargeable species, groups, or monomeric units. In certain instances, the first chargeable groups, species or monomeric units are negatively charged or chargeable to a negative species, group, or monomeric unit. In some instances, the second chargeable groups, species, or monomeric units are positively charged or chargeable to cationic species, groups, or monomeric units. In certain embodiments, as the pH of an aqueous medium comprising a micellic assembly described herein increases, the core block of the membrane destabilizing block copolymers and the core of the micellic assembly become more positively charged, resulting in a disruption of the shape and/or size of the micellic assembly, and causing partial or substantial disruption of a membrane (e.g., an endosomal membrane surrounding the micellic assembly).

In certain embodiments, the micellic assemblies provided herein comprise a plurality of membrane-destabilizing block copolymers which destabilize an endosomal membrane in a pH-dependent manner. In various embodiments, the membrane-destabilizing block copolymers destabilize a membrane when assembled in the micellic assemblies and/or when present independent of the micellic assemblies form (e.g., when the micellic assemblies are disassociated and/or destabilized). In some embodiments, at or near physiological pH (e.g., pH of circulating blood), the polymers making up the micellic assemblies are minimally membrane-destabilizing, but upon exposure to decreased pH (e.g., endosomal pH), the polymer is membrane-destabilizing. In certain instances, this transition to a membrane-destabilizing state occurs via the protonation of weakly acidic residues that are incorporated into the polymers, such protonation leading to an increase in the hydrophobicity of the polymers. In certain instances, the increased hydrophobicity of the polymer results in a conformational change of the micellic assemblies, making the micellic assemblies membrane-destabilizing (e.g., causing destabilization of the membrane). In some embodiments, the mechanism of membrane destabilization of the micellic assemblies provided herein does not rely on a purely proton-sponge membrane destabilizing mechanism of polycations such as PEI or other polycations. In some embodiments, the combination of two mechanisms of membrane disruption, (a) a polycation (such as DMAEMA) and (b) a hydrophobized poly anion (such as propylacrylic acid), acting together have an additive or synergistic effect on the potency of the membrane destabilization conferred by the polymer.

In some embodiments, polymer blocks are optionally selected from, by way of non-limiting example, polynucleotides, oligonucleotides, polyethyleneglycols, hydrophilic block, hydrophobic blocks, charged blocks, or the like.

In certain embodiments, micellic assemblies described herein comprise membrane destabilizing block copolymers, wherein the block copolymers are non-peptidic and/or non-lipidic. Provided herein are micellic assemblies comprising membrane destabilizing block copolymers wherein the core block is non-peptidic and/or non-lipidic. In certain embodiments, the micellic assemblies described herein comprise membrane destabilizing block copolymers wherein the shell block is non-peptidic and/or non-lipidic. In some embodiments, the backbone of the block copolymers forming the micellic assembly is non-peptidic and/or non-lipidic. In certain embodiments, the backbone of the core block is non-peptidic and/or non-lipidic. In some embodiments, the shell block is non-peptidic and/or non-lipidic. As used herein, lipids are a diverse group of compounds broadly defined as hydrophobic or amphiphilic molecules that originate entirely or in part from two distinct types of biochemical subunits: ketoacyl and isoprene groups, e.g., fatty acids, glycerolipids, glycerophoispholipids, sphingolipids, saccharolipids, polyke tides, sterol lipids, and prenol lipids.

In some embodiments, provided herein is a micellic assembly comprising a plurality of membrane destabilizing block copolymers comprising a core section (e.g., core block) and a shell section (e.g., shell block) wherein the ratio of the number average molecular weight of the core section (e.g., core block) to the number average molecular weight of the shell section (e.g., shell block) is present in any suitable ratio. In specific embodiments, membrane destabilizing block copolymers wherein the ratio of the number average molecular weight of the core section (e.g., core block) to the number average molecular weight of the shell section (e.g., shell block) is present in a ratio of about 1:10 to about 5:1, about 1:1 to about 5:1, about 5:4 to about 5:1, about 1:2 to about 2:1, about 2:1, about 1.5:1, about 1.1:1, about 1.2:1, about 1.3:1, about 1.4:1, about 1.6:1, about 1.7:1, about 1.8:1, about 1.9:1, or about 2.1:1. In some embodiments, membrane destabilizing block copolymers wherein the ratio of the number average molecular weight of the core section (e.g., core block) to the number average molecular weight of the shell section (e.g., shell block) is present in a ratio of about 2 (or more) to 1; about 1.5 (or more) to 1; about 1.1 (or more) to 1; about 1.2 (or more) to 1; about 1.3 (or more) to 1; about 1.4 (or more) to 1; about 1.6 (or more) to 1; about 1.7 (or more) to 1; about 1.8 (or more) to 1; about 1.9 (or more) to 1; or about 2.1 (or more) to 1. In specific embodiments, the ratio of the number average molecular weight of the core block to the number average molecular weight of the shell block is about 2:1.

In specific embodiments, the micellic assembly provided herein comprises at least one type of polymer (e.g., block copolymers and/or monoblock polymers, including monoblock copolymers) having a hydrophilic segment and a hydrophobic segment. In certain embodiments, the hydrophilic segment is a hydrophilic block and the hydrophobic segment is a hydrophobic block. In some embodiments, these polymers are non-peptidic. In other embodiments, the hydrophilic segment and the hydrophobic segment are different regions of a monoblock gradient copolymer. In various instances, a "polymeric segment" is a polymer section with a given physical property (e.g., a physical property of a block described herein, e.g., hydrophobicity, hydrophilicity, chargeability, etc.) or which comprises one or more blocks with similar physical properties (e.g., hydrophobicity, hydrophilicity, chargeability, etc.).

In certain embodiments, one or more or all of the polymers (including at least a plurality of membrane destabilizing block copolymers, and, optionally, non-membrane destabilizing block copolymers) of a micellic assembly described herein each have (1) an optionally charged hydrophilic segment (e.g., a shell block) forming at least a portion of the shell of the micellic assembly (e.g., micelle); and (2) a substantially hydrophobic segment (e.g., a core block) forming at least a portion of the hydrophobic core of the micellic assembly (e.g., micelle) which is stabilized through hydrophobic interactions of the core-forming polymeric segments. In some embodiments the hydrophilic segment is neutral or non-charged. In some embodiments the hydrophilic segment is charged and cationic, or polycationic. In some embodiments the hydrophilic segment is charged and anionic, or polyanionic. In some embodiments the hydrophilic segment is charged and zwitterionic. In some cases, the hydrophilic segment may serve at least three functions: (1) to form the shell of the micellic structure, (2) to increase the aqueous dispersability of the micellic assembly, and (3) to attach to (e.g., bind) one or more therapeutic agent (e.g., oligonucleotide-based therapeutic molecules such as siRNA). In some embodiments, core block of the membrane destabilizing block copolymers and/or core of the micellic assembly also comprise chargeable or charged species (e.g., anionic and/or cationic species/monomeric units at a physiological pH) and are membrane-destabilizing (e.g., membrane destabilizing in a pH dependent manner). In some embodiments, the substantially hydrophobic block (e.g., core block) and/or the core of the micellic assembly comprises one or more chargeable species (e.g., monomeric unit, moiety, group, or the like). In more specific embodiments, the substantially hydrophobic block and/or core of the micellic assembly comprise a plurality of cationic species and a plurality of anionic species. In still more specific embodiments, the core block of the membrane destabilizing block copolymers and/or core of the micellic assembly comprises a substantially similar number of cationic and anionic species (i.e., the hydrophobic block and/or core are substantially net neutral).

In certain embodiments, a micellic assembly provided herein comprises a hydrophobic core block comprising a first and a second chargeable species. In some embodiments, the first chargeable species is as described herein and the second chargeable species is chargeable to a cationic species upon protonation. In specific embodiments, the first chargeable species is non-charged at an acidic pH (e.g., an endosomal pH, a pH below about 6.5, a pH below about 6.0, a pH below about 5.8, a pH below about 5.7, or the like). In specific embodiments, the $pK_a$ of the second chargeable species is about 6 to about 10, about 6.5 to about 9, about 6.5 to about 8, about 6.5 to about 7.5, or any other suitable $pK_a$. In certain embodiments, at least one of the first chargeable species and at least one of the second chargeable species are present on a single monomeric unit. In some embodiments, the first chargeable species is found on a first chargeable monomeric unit and the second chargeable species is on a second chargeable monomeric unit. In certain embodiments, the first chargeable species is chargeable to an anionic species upon deprotonation, the second chargeable species is chargeable to a cationic species upon protonation, and the ratio of the anionic species to the cationic species is between about 1:10 and about 10:1, about 1:6 and about 6:1, about 1:4 and about 4:1, about 1:2 and about 2:1, about 1:2 and 3:2, or about 1:1 at about a neutral pH. In some embodiments, the ratio of the first chargeable monomeric unit to the second chargeable monomeric unit is about 1:10 and about 10:1, about 1:6 and about 6:1, about 1:4 and about 4:1, about 1:2 and about 2:1, about 1:2 and 3:2, or about 1:1.

The term "copolymer", as used herein, signifies that the polymer is the result of polymerization of two or more different monomers. A "monoblock polymer" or a "subunit polymer" of a micellic assembly described herein is a synthetic product of a single polymerization step. The term monoblock polymer includes a copolymer (i.e. a product of polymerization of more than one type of monomers) and a homopolymer (i.e., a product of polymerization of a single type of monomers). A "block" copolymer refers to a structure comprising one or more sub-combination of constitutional or monomeric units, used interchangeably herein. Such constitutional or monomeric units comprise residues of polymerized monomers. In some embodiments, a block copolymer described herein comprises non-lipidic constitutional or monomeric units. In some embodiments, the block copolymer is a diblock copolymer. A diblock copolymer comprises two blocks; a schematic generalization of such a polymer is represented by the following: $[A_aB_bC_c \ldots ]_m$-$[X_xY_yZ_z \ldots ]_n$, wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight of each block in the diblock copolymer. As suggested by the schematic, in some instances, the number and the nature of each constitutional unit is separately controlled for each block. The schematic is not meant and should not be construed to infer any relationship whatsoever between the number of constitutional units or the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the non-limiting form: x-x-y-z-x-y-z-y-z-z-z . . . A non-limiting, exemplary alternating random configuration may have the non-limiting form: x-y-x-z-y-x-y-z-y-x-z . . . , and an exemplary regular alternating configuration may have the non-limiting form: x-y-z-x-y-z-x-y-z .. . An exemplary regular block configuration may have the following non-limiting configuration: . . . x-x-x-y-y-y-z-z-z-x-x-x . . . , while an exemplary random block configuration may have the non-limiting configuration: . . . x-x-x-z-z-x-x-y-y-y-y-z-z-z-x-x-z-z-z- . . . In a gradient polymer, the content of one or more monomeric units increases or decreases in a gradient manner from the α end of the polymer to the w end. In none of the preceding generic examples is the particular juxtaposition of individual constitutional units or blocks or the number of constitutional units in a block or the number of blocks meant nor should they be construed as in any manner bearing on or limiting the actual structure of block copolymers forming the micellic assembly of this invention. In certain embodiments, provided herein is any subunit polymer or composition of subunit polymers described herein, regardless of whether or not such polymers are assembled into a micellic assembly.

As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers. In some embodiments, the block copolymers are dendrimer, star or graft copolymers.

In certain embodiments, block copolymers (e.g., membrane destabilizing block copolymers) of the micellic assemblies provided herein comprise ethylenically unsaturated monomers. The term "ethylenically unsaturated monomer" is defined herein as a compound having at least one carbon double or triple bond. The non-limiting examples of the ethylenically unsaturated monomers are: an alkyl (alkyl) acrylate, a methacrylate, an acrylate, an alkylacrylamide, a methacrylamide, an acrylamide, a styrene, an allylamine, an allylammonium, a diallylamine, a diallylammonium, an N-vinyl formamide, a vinyl ether, a vinyl sulfonate, an acrylic acid, a sulfobetaine, a carboxybetaine, a phosphobetaine, or maleic anhydride.

In various embodiments, any monomer suitable for providing the polymers (including, e.g., the membrane destabilizing block copolymers) of the micellic assemblies described herein is used. In some embodiments, monomers suitable for use in the preparation of the polymers (including, e.g., the membrane destabilizing block copolymers) of the micellic assemblies provided herein include, by way of non-limiting example, one or more of the following monomers: methyl methacrylate, ethyl acrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, oligoethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolacrylamide, N-ethylolacrylamide, vinyl benzoic acid (all isomers), diethylaminostyrene (all isomers), alpha-methyl vinyl benzoic acid (all isomers), diethylamino alpha-methylstyrene (all isomers), p-vinylbenzenesulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropylmethacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysillpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-arylmaleimide, N-phenylmaleimide, N-alkylmaleimide, N-butylimaleimide, N-vinylpyrrolidone, N-vinylcarbazole, butadiene, isoprene, chloroprene, ethylene, propylene, 1,5-hexadienes, 1,4-hexadiencs, 1,3-butadienes, 1,4-pcntadiencs, vinylalcohol, vinylamine, N-alkylvinylamine, allylamine, N-alkylallylamine, diallylamine, N-alkyldiallylamine, alkylenimine, acrylic acids, alkylacrylates, acrylamides, methacrylic acids, alkylmethacrylates, methacrylamides, N-alkylacrylamides, N-alkylmethacrylamides, N-isopropylacrylamide, vinylnaphthalene, vinyl pyridine, ethylvinylbenzene, aminostyrene, vinylpyridine, vinylimidazole, vinylbiphenyl, vinylanisole, vinylimidazolyl, vinylpyridinyl, vinylpolyethyleneglycol, dimethylaminomethylstyrene, trimethylammonium ethyl methacrylate, trimethylammonium ethyl acrylate, dimethylamino propylacrylamide, trimethylammonium ethylacrylate, trimethylanunonium ethyl methacrylate, trimethylammonium propyl acrylamide, dodecyl acrylate, octadecyl acrylate, or octadecyl methacrylate monomers, or combinations thereof.

In some embodiments, functionalized versions of these monomers are optionally used. A functionalized monomer, as used herein, is a monomer comprising a masked or non-masked functional group, e.g. a group to which other moieties can be attached following the polymerization. The non-limiting examples of such groups are primary amino groups, carboxyls, thiols, hydroxyls, azides, and cyano groups. Several suitable masking groups are available (see, e.g., T. W. Greene & P. G. M. Wuts, Protective Groups in Organic Synthesis (2nd edition) J. Wiley & Sons, 1991. P. J. Kocienski, Protecting Groups, Georg Thieme Verlag, 1994)

Polymers described here are prepared in any suitable manner. Suitable synthetic methods used to produce the polymers provided herein include, by way of non-limiting example, cationic, anionic and free radical polymerization. In some instances, when a cationic process is used, the monomer is treated with a catalyst to initiate the polymerization. Optionally, one or more monomers are used to form a copolymer. In some embodiments, such a catalyst is an initiator, including, e.g., protonic acids (Brønsted acid) or Lewis acids, in the case of using Lewis acid some promoter such as water or alcohols are also optionally used. In some embodiments, the catalyst is, by way of non-limiting example, hydrogen iodide, perchloric acid, sulfuric acid, phosphoric acid, hydrogen fluoride, chlorosulfonic acid, methansulfonic acid, trifluoromehtanesulfonic acid, aluminum trichloride, alkyl aluminum chlorides, boron trifluoride complexes, tin tetrachloride, antimony pentachloride, zinc chloride, titanium tetrachloride, phosphorous pentachloride, phosphorus oxychloride, or chromium oxychloride. In certain embodiments, polymer synthesis is performed neat or in any suitable solvent. Suitable solvents include, but are not limited to, pentane, hexane, dichloromethane, chloroform, or dimethyl formamide (DMF). In certain embodiments, the polymer synthesis is performed at any suitable reaction temperature, including, e.g., from about −50° C. to about 100° C., or from about 0° C. to about 70° C.

In certain embodiments, the polymers are prepared by the means of a free radical polymerization. When a free radical polymerization process is used, (i) the monomer, (ii) optionally, the co-monomer, and (iii) an optional source of free radicals are provided to trigger a free radical polymerization process. In some embodiments, the source of free radicals is optional because some monomers may self-initiate upon heating at high temperature. In certain instances, after forming the polymerization mixture, the mixture is subjected to polymerization conditions. Polymerization conditions are those conditions that cause at least one monomer to form at least one polymer, as discussed herein. Such conditions are optionally varied to any suitable level and include, by way of non-limiting example, temperature, pressure, atmosphere, ratios of starting components used in the polymerization mixture and reaction time. The polymerization is carried out in any suitable manner, including, e.g., in solution, dispersion, suspension, emulsion or bulk.

In some embodiments, initiators are present in the reaction mixture. Any suitable initiators is optionally utilized if useful in the polymerization processes described herein. Such initiators include, by way of non-limiting example, one or more of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, or azo compounds. In specific embodiments, benzoylperoxide (BPO) and/or AIBN are used as initiators.

In some embodiments, polymerization processes are carried out in a living mode, in any suitable manner, such as but not limited to Atom Transfer Radical Polymerization (ATRP), nitroxide-mediated living free radical polymerization (NMP), ring-opening polymerization (ROP), degenerative transfer (DT), or Reversible Addition Fragmentation Transfer (RAFT). Using conventional and/or living/controlled polymerizations methods, various polymer architectures can be produced, such as but not limited to block, graft, star and gradient copolymers, whereby the monomer units are either distributed statistically or in a gradient fashion across the chain or homopolymerized in block sequence or pendant grafts. In other embodiments, polymers are synthesized by Macromolecular design via reversible addition-fragmentation chain transfer of Xanthates (MADIX) (Direct Synthesis of Double Hydrophilic Statistical Di-and Triblock Copolymers Comprised of Acrylamide and Acrylic Acid Units via the MADIX Process", Daniel Taton, et al., Macromolecular Rapid Communications, 22, No. 18, 1497-1503 (2001).)

In certain embodiments, Reversible Addition-Fragmentation chain Transfer or RAFT is used in synthesizing ethylenic backbone polymers of this invention. RAFT is a living polymerization process. RAFT comprises a free radical degenerative chain transfer process. In some embodiments, RAFT procedures for preparing a polymer described herein employs thiocarbonylthio compounds such as, without limitation, dithioesters, dithiocarbamates, trithiocarbonates and xanthates to mediate polymerization by a reversible chain transfer mechanism. In certain instances, reaction of a polymeric radical with the C=S group of any of the preceding compounds leads to the formation of stabilized radical intermediates. Typically, these stabilized radical intermediates do not undergo the termination reactions typical of standard radical polymerization but, rather, reintroduce a radical capable of re-initiation or propagation with monomer, reforming the C=S bond in the process. In most instances, this cycle of addition to the C=S bond followed by fragmentation of the ensuing radical continues until all monomer has been consumed or the reaction is quenched. Generally, the low concentration of active radicals at any particular time limits normal termination reactions.

In some embodiments, polymers (e.g., membrane destabilizing block copolymers) utilized in the micellic assemblies (e.g., micelles) provided herein have a low polydispersity index (PDI) or differences in chain length. Polydispersity index (PDI) can be determined in any suitable manner, e.g., by dividing the weight average molecular weight of the polymer chains by their number average molecular weight. The number average molecule weight is sum of individual chain molecular weights divided by the number of chains. The weight average molecular weight is proportional to the square of the molecular weight divided by the number of molecules of that molecular weight. Since the weight average molecular weight is always greater than the number average molecular weight, polydispersity is always greater than or equal to one. As the numbers come closer and closer to being the same, i.e., as the polydispersity approaches a value of one, the polymer becomes closer to being monodisperse in which every chain has exactly the same number of constitutional units. Polydispersity values approaching one are achievable using radical living polymerization. Methods of determining polydispersity, such as, but not limited to, size exclusion chromatography, dynamic light scattering, matrix-assisted laser desorption/ionization chromatography and electrospray mass chromatography are well known in the art. In some embodiments, block copolymers (e.g., membrane destabilizing block copolymers) of the micellic assemblies (e.g., micelles) provided herein have a polydispersity index (PDI) of less than 2.0, or less than 1.8, or less than 1.6, or less than 1.5, or less than 1.4, or less than 1.3, or less than 1.2.

Polymerization processes described herein optionally occur in any suitable solvent or mixture thereof. Suitable solvents include water, alcohol(e.g., methanol, ethanol, n-propanol, isopropanol, butanol), tetrahydrofuran (THF) dimethyl sulfoxide (DMSO), dimethylformamide (DMF), acetone, acetonitrile, hexamethylphosphor amide, acetic acid, formic acid, hexane, cyclohexane, benzene, toluene, dioxane, methylene chloride, ether (e.g., diethyl ether), chloroform, and ethyl acetate. In one aspect, the solvent includes water, and mixtures of water and water-miscible organic solvents such as DMF.

In certain embodiments, poly(DMAEMA) and other polymeric entities used herein (e.g., copolymers or copolymer blocks of BMA, DMAEMA and PAA) are prepared in any suitable manner. In one embodiment, poly(DMAEMA) is prepared by polymerizing DMAEMA in the presence of the RAFT CTA, ECT, and a radical initiator. In some embodiments, a block, poly(DMAEMA) macroCTA is used to prepare a series of diblock copolymers where the second block contained BMA, DMAEMA and PAA. In other specific embodiments, the orientation of the blocks on the diblock polymer is reversed, such that upon self-assembly, the co end of the polymer is exposed on the hydrophilic segment of the micelle or micellic assembly. In various embodiments, this is achieved in any suitable manner, including a number of ways synthetically. For example, in some embodiments, the synthesis of the block copolymers described herein begins with the preparation of the PAA/BMA/DMAEMA core-forming hydrophobic block, and the shell-forming hydrophilic, charged block is added in the second synthetic step by subjecting the resulting PAA/BMA/DMAEMA macroCTA to a second RAFT polymerization step. Alternate approaches include reducing the PAA/BMA/

DMAEMA macroCTA to form a thiol end and then covalently attaching a pre-formed hydrophilic, charged polymer to the formed thiol. This synthetic approach provides a method for introduction of a reactive group on the w-end of the polymeric chain exposed to the surface of micelle thus providing alternate approaches to chemical conjugation to the micelle.

In some embodiments, block copolymers are synthesized by chemical conjugation of several polymer blocks that are prepared by separate polymerization processes.

In some instances, the block copolymers (e.g., membrane destabilizing block copolymers) comprise monomers bearing reactive groups which can be used for post-polymerization introduction of additional functionalities via know in the art chemistries, for example, "click" chemistry (for example of "click" reactions, see Wu, P.; Fokin, V. V. Catalytic Azide-Alkyne Cycloaddition: Reactivity and Applications. *Aldrichim. Acta*, 2007, 40, 7-17).

In specific instances, provided herein are the polymers (e.g., block copolymers including membrane destabilizing block copolymers) of the following structure:

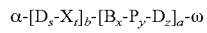  [Structure 1]

  [Structure 2]

wherein x, y, z, s and t are the mole % composition (generally, 0-50%) of the individual monomeric units D (DMAEMA), B (BMA), P (PAA), and a hydrophilic neutral monomer (X) in the polymer block, a and b are the molecular weights of the blocks, $[D_s\text{-}X_t]$ is the hydrophilic core block, and $\alpha$ and $\omega$ denote the opposite ends of the polymer. In certain embodiments, x is 50%, y is 25% and z is 25%. In certain embodiments, x is 60%, y is 20% and z is 20%. In certain embodiments, x is 70%, y is 15% and z is 15%. In certain embodiments, x is 50%, y is 25% and z is 25%. In certain embodiments, x is 33%, y is 33% and z is 33%. In certain embodiments, x is 50%, y is 20% and z is 30%. In certain embodiments, x is 20%, y is 40% and z is 40%. In certain embodiments, x is 30%, y is 40% and z is 30%. In some embodiments, a micellic assembly described herein comprises a hydrophilic block of about 2,000 Da to about 30,000 Da, about 5,000 Da to about 20,000 Da, or about 7,000 Da to about 15,000 Da. In specific embodiments, the hydrophilic block is of about 7,000 Da, 8,000 Da, 9,000 Da, 10,000 Da, 11,000 Da, 12,000 Da, 13,000 Da, 14,000 Da, or 15,000 Da. In certain embodiments, a micellic assembly described herein comprises a hydrophobic core block of about 2,000 Da to about 50,000 Da, about 10,000 Da to about 50,000 Da, 15,000 Da to about 35,000 Da, or about 20,000 Da to about 30,000 Da. In some specific embodiments, the polymer with a hydrophilic block is of 12,500 Da and a hydrophobic core block of 25,000 Da (length ratio of 1:2) forms micellic assemblies (e.g., micelles). In some specific embodiments, the polymer with a hydrophilic block is of 10,000 Da and a hydrophobic core block of 30,000 Da (length ratio of 1:3) forms micellic assemblies (e.g., micelles). In some specific embodiments, the polymer with a hydrophilic block is of 10,000 Da and a hydrophobic core block of 25,000 Da (length ratio of 1:2.5) forms micellic assemblies (e.g., micelles) of approximately 45 nm (as determined by dynamic light scattering measurements or electron microscopy). In some specific embodiments, the micelles are 80 or 130 nm (as determined by dynamic light scattering measurements or electron microscopy). Typically, as the molecular weight (or length) of $[D_s\text{-}X_t]$, which forms the micelle shell, increases relative to $[B_x\text{-}P_y\text{-}D_z]$ the hydrophobic core block that forms the core, the size of the micelle increases. In some instances, the size of the polymer cationic block that forms the shell ($[D_s\text{-}X_t]$) is important in providing effective complex formation/charge neutralization with the oligonucleotide drug. For example, in certain instances, for siRNA of approximately 20 base pairs (i.e., 40 anionic charges) a cationic block has a length suitable to provide effective binding, for example 40 cationic charges. For a shell block containing 80 DMAEMA monomers (MW=11,680) with a $pK_a$ value of 7.4, the block contains 40 cationic charges at pH 7.4. In some instances, stable polymer-siRNA conjugates (e.g., complexes) form by electrostatic interactions between similar numbered opposite charges. In certain instances, avoiding a large number of excess positive charge helps to prevent significant in vitro and in vivo toxicity.

In specific embodiments, the hydrophobic core block of the block copolymer comprises a plurality a cationic chargeable species, for example, dimethylaminoethylmethacrylate (DMAEMA). Thus, in some embodiments, the structure of such a polymeric segment is represented by the Structure 3:

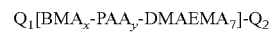  [Structure 3]

wherein $Q_1$ and $Q_2$ in the above designation denote other polymer blocks or end group functionalities, and wherein x, y, and z are the mole % composition (generally, 0-50%) of the individual monomeric units. In certain instances, the individual monomeric units serve individual and synergistic functions. For example, polypropyl acrylic acid, which comprises both anionic species and hydrophobic species, with a $pK_a$ value of ~6.7 is hydrophilic above a pH of about 6.7 and is increasingly hydrophobic below a pH of about 6.7, where the carboxylates become protonated. In certain instances, increasing the hydrophobicity of the local environment, for example, by increasing the mole % of the predominantly hydrophobic monomer unit BMA in the block raises the PAA $pK_a$ and results in protonation of PAA at a higher pH, that is, the PAA containing block becomes more membrane destabilizing at a higher pH and thus more responsive to smaller acidic changes in pH below physiological pH ~7.4. In some instances, protonation of PAA results in a large increase in hydrophobicity and subsequent conformational change to a form with membrane destabilizing properties. A third monomeric unit in the above described polymer block is the cationic species, for example DMAEMA, which, in some instances, serves multiple functions, including but not limited to the following. When matched in equivalent molar amounts to the anionic species of PAA, it creates charge neutralization and the potential for forming electrostatic interactions that can contribute to the stability of the hydrophobic core of a micelle structure where either $Q_1$ or $Q_2$ in the above structure is a hydrophilic homopolymer block, for example polyDMAEMA.

In certain embodiments, the block copolymer (e.g., membrane destabilizing block copolymer) has the chemical Formula I:

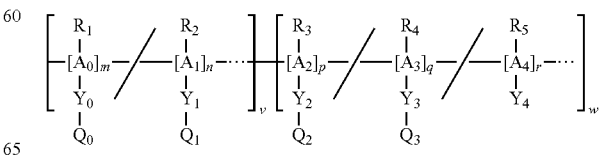

In Some Embodiments:

$A_0$, $A_1$, $A_2$, $A_3$ and $A_4$ are selected from the group consisting of —C—, —C—C—, —C(O)(C)$_a$C(O)O—, —O(C)$_a$C(O)— and —O(C)$_b$O—; wherein, a is 1-4;

b is 2-4;

$Y_4$ is selected from the group consisting of hydrogen, (1C-10C)alkyl, (3C-6C)cycloalkyl, O-(1C-10C)alkyl, —C(O)O(1C-10C)alkyl, C(O)NR$_6$(1C-10C), (4C-10C)heteroaryl and (6C-10C)aryl, any of which is optionally substituted with one or more fluorine groups;

$Y_0$, $Y_1$ and $Y_2$ are independently selected from the group consisting of a covalent bond, (1C-10C)alkyl-, —C(O)O (2C-10C) alkyl-, —OC(O)(1C-10C) alkyl-, —O(2C-10C) alkyl- and —S(2C-10C)alkyl-, —C(O)NR$_6$(2C-10C) alkyl-, -(4C-10C)heteroaryl- and -(6C-10C)aryl-;

$Y_3$ is selected from the group consisting of a covalent bond, -(1C-10C)alkyl-, -(4C-10C)heteroaryl- and -(6C-10C) aryl-; wherein tetravalent carbon atoms of $A_0$-$A_4$ that are not fully substituted with $R_1$-$R_5$ and $Y_0$-$Y_4$ are completed with an appropriate number of hydrogen atoms;

$R_1$, $R_2$, $R_3$, $R_4$, $R_5$, and $R_6$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_0$ is a residue selected from the group consisting of residues which are hydrophilic at physiologic pH, and are at least partially positively charged at physiologic pH (e.g., amino, alkylamino, ammonium, alkylammonium, guanidine, imidazolyl, pyridyl, or the like); at least partially negatively charged at physiologic pH but undergo protonation at lower pH (e.g., carboxyl, sulfonamide, boronate, phosphonate, phosphate, or the like); substantially neutral (or non-charged) at physiologic pH (e.g., hydroxy, polyoxylated alkyl, polyethylene glycol, polypropylene glycol, thiol, or the like); at least partially zwitterionic at physiologic pH (e.g., a monomeric residue comprising a phosphate group and an ammonium group at physiologic pH); conjugatable or functionalizable residues (e.g. residues that comprise a reactive group, e.g., azide, alkyne, succinimide ester, tetrafluorophenyl ester, pentafluorophenyl ester, p-nitrophenyl ester, pyridyl disulfide, or the like); or hydrogen;

$Q_1$ is a residue which is hydrophilic at physiologic pH, and is at least partially positively charged at physiologic pH (e.g., amino, alkylamino, ammonium, alkylammonium, guanidine, imidazolyl, pyridyl, or the like); at least partially negatively charged at physiologic pH but undergoes protonation at lower pH (e.g., carboxyl, sulfonamide, boronate, phosphonate, phosphate, or the like); substantially neutral at physiologic pH (e.g., hydroxy, polyoxylated alkyl, polyethylene glycol, polypropylene glycol, thiol, or the like); or at least partially zwitterionic at physiologic pH (e.g., comprising a phosphate group and an ammonium group at physiologic pH);

$Q_2$ is a residue which is positively charged at physiologic pH, including but not limited to amino, alkylamino, ammonium, alkylammonium, guanidine, imidazolyl, and pyridyl;

$Q_3$ is a residue which is negatively charged at physiologic pH, but undergoes protonation at lower pH, including but not limited to carboxyl, sulfonamide, boronate, phosphonate, and phosphate;

m is about 0 to less than 1.0 (e.g., 0 to about 0.49);

n is greater than 0 to about 1.0 (e.g., about 0.51 to about 1.0); wherein $m+n=1$ p is about 0.1 to about 0.9 (e.g., about 0.2 to about 0.5);

q is about 0.1 to about 0.9 (e.g., about 0.2 to about 0.5); wherein:

r is 0 to about 0.8 (e.g., 0 to about 0.6); wherein $p+q+r=1$ v is from about 1 to about 25 kDa, or about 5 to about 25 kDa; and, w is from about 1 to about 50 kDa, or about 5 to about 50 kDa.

In some embodiments, the number or ratio of monomeric residues represented by p and q are within about 30% of each other, about 20% of each other, about 10% of each other, or the like. In specific embodiments, p is substantially the same as q. In certain embodiments, at least partially charged generally includes more than a trace amount of charged species, including, e.g., at least 20% of the residues are charged, at least 30% of the residues are charged, at least 40% of the residues are charged, at least 50% of the residues are charged, at least 60% of the residues are charged, at least 70% of the residues are charged, or the like.

In certain embodiments, m is 0 and $Q_1$ is a residue which is hydrophilic and substantially neutral (or non-charged) at physiologic pH. In some embodiments, substantially non-charged includes, e.g., less than 5% are charged, less than 3% are charged, less than 1% are charged, or the like. In certain embodiments, m is 0 and $Q_1$ is a residue which is hydrophilic and at least partially cationic at physiologic pH. In certain embodiments, m is 0 and $Q_1$ is a residue which is hydrophilic and at least partially anionic at physiologic pH. In certain embodiments, m is >0 and n is >0 and one of and $Q_0$ or $Q_1$ is a residue which is hydrophilic and at least partially cationic at physiologic pH and the other of $Q_0$ or $Q_1$ is a residue which is hydrophilic and is substantially neutral at physiologic pH. In certain embodiments, m is >0 and n is >0 and one of and $Q_0$ or $Q_1$ is a residue which is hydrophilic and at least partially anionic at physiologic pH and the other of $Q_0$ or $Q_1$ is a residue which is hydrophilic and is substantially neutral at physiologic pH. In certain embodiments, m is >0 and n is >0 and $Q_1$ is a residue which is hydrophilic and at least partially cationic at physiologic pH and $Q_0$ is a residue which is a conjugatable or functionalizable residue. In certain embodiments, m is >0 and n is >0 and $Q_1$ is a residue which is hydrophilic and substantially neutral at physiologic pH and $Q_0$ is a residue which is a conjugatable or functionalizable residue.

In certain embodiments, a micellic assembly described herein comprises a block copolymer of Formula II:

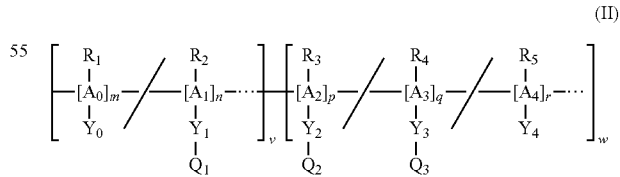

(II)

In Some Embodiments:

$A_0$, $A_1$, $A_2$, $A_3$ and $A_4$ are selected from the group consisting of —C—C—, —C(O)(C)$_a$C(O)O—, —O(C)$_a$C(O)— and —O(C)$_b$O—; wherein, a is 1-4;

b is 2-4;

$Y_0$ and $Y_4$ are independently selected from the group consisting of hydrogen, (1C-10C)alkyl, (3C-6C)cycloalkyl, O-(1C-10C)alkyl, —C(O)O(1C-10C)alkyl, C(O)NR$_6$(1C-10C), (4C-10C)heteroaryl and (6C-10C)aryl, any of which is optionally substituted with one or more fluorine groups;

$Y_1$ and $Y_2$ are independently selected from the group consisting of a covalent bond, (1C-10C)alkyl-, —C(O)O(2C-10C)alkyl-, —OC(O)(1C-10C)alkyl-, —O(2C-10C)alkyl-, —S(2C-10C)alkyl-, —C(O)NR$_6$(2C-10C) alkyl, -(4C-10C)heteroaryl- and -(6C-10C)aryl-;

$Y_3$ is selected from the group consisting of a covalent bond, (1C-10C)alkyl, (4C-10C)heteroaryl and (6C-10C)aryl; wherein tetravalent carbon atoms of $A_p$-$A_4$ that are not fully substituted with $R_1$-$R_5$ and $Y_0$-$Y_4$ are completed with an appropriate number of hydrogen atoms;

$R_1$, $R_2$, $R_3$, $R_4$, $R_5$, and $R_6$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_1$ and $Q_2$ are residues which are positively charged at physiologic pH, including but not limited to amino, alkylamino, ammonium, alkylammonium, guanidine, imidazolyl, and pyridyl.

$Q_3$ is a residue which is negatively charged at physiologic pH, but undergoes protonation at lower pH, including but not limited to carboxyl, sulfonamide, boronate, phosphonate, and phosphate.

m is 0 to about 0.49;

n is about 0.51 to about 1.0; wherein $$m+n=1$$

p is about 0.2 to about 0.5;

q is about 0.2 to about 0.5; wherein:

p is substantially the same as q;

r is 0 to about 0.6; wherein $$p+q+r=1$$

v is from about 1 to about 25 kDa, or about 5 to about 25 kDa; and, w is from about 1 to about 50 kDa, or about 5 to about 50 kDa.

In certain embodiments, a micellic assembly described herein comprises a block copolymer (e.g., at normal physiological pH) of Formula III:

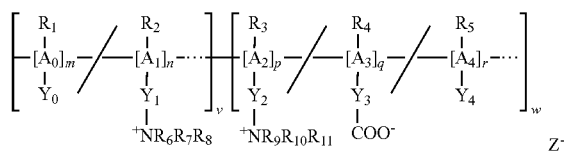
(III)

In certain embodiments, $A_0$, $A_1$, $A_2$, $A_3$, and $A_4$, substituted as indicated comprise the constitutional units (used interchangeably herein with "monomeric units" and "monomeric residues") of the polymer of Formula III. In specific embodiments, the monomeric units of constituting the A groups of Formula III are polymerizably compatible under appropriate conditions. In certain instances, an ethylenic backbone or constitutional unit, —(C—O)$_m$-polymer, wherein each C is di-substituted with H and/or any other suitable group, is polymerized using monomers containing a carbon-carbon double bond, >C=C<. In certain embodiments, each A group (e.g., each of $A_0$, Ai, $A_2$, $A_3$, and $A_4$) may be (i.e., independently selected from) —C—C— (i.e., an ethylenic monomeric unit or polymer backbone), —C(O)(C)$_a$C(O)O— (i.e., a polyanhydride monomeric unit or polymer backbone), —O(C)$_a$C(O)—(i.e., a polyester monomeric unit or polymer backbone), —O(C)$_b$O— (i.e., a polyalkylene glycol monomeric unit or polymer backbone), or the like (wherein each C is di-substituted with H and/or any other suitable group such as described herein, including $R_{12}$ and/or $R_{13}$ as described above). In specific embodiments, the term "a" is an integer from 1 to 4, and "b" is an integer from 2 to 4. In certain instances, each "Y" and "R" group attached to the backbone of Formula III (i.e., any one of $Y_0$, $Y_1$, $Y_2$, $Y_3$, $Y_4$, $R_1$, $R_2$, $R_3$, $R_4$, $R_5$) is bonded to any "C" (including any (C)a or (C)$_b$) of the specific monomeric unit. In specific embodiments, both the Y and R of a specific monomeric unit is attached to the same "C". In certain specific embodiments, both the Y and R of a specific monomeric unit is attached to the same "C", the "C" being alpha to the carbonyl group of the monomeric unit, if present.

In specific embodiments, $R_1$-$R_{11}$ are independently selected from hydrogen, alkyl (e.g., 1C-5C alkyl), cycloalkyl (e.g., 3C-6C cycloalkyl), or phenyl, wherein any of $R_1$-$R_{11}$ is optionally substituted with one or more fluorine, cycloalkyl, or phenyl, which may optionally be further substituted with one or more alkyl group.

In certain specific embodiments, $Y_0$ and $Y_4$ are independently selected from hydrogen, alkyl (e.g., 1C-10C alkyl), cycloalkyl (e.g., 3C-6C cycloalkyl), O-alkyl (e.g., O-(2C-10C)alkyl, —C(O)O-alkyl (e.g., —C(O)O-(2C-10C)alkyl), or phenyl, any of which is optionally substituted with one or more fluorine.

In some embodiments, $Y_1$ and $Y_2$ are independently selected from a covalent bond, alkyl, preferably at present a (1C-10C)alkyl, —C(O)O-alkyl, preferably at present —C(O)O-(2C-10C)alkyl, —OC(0)alkyl, preferably at present-OC(O)-(2C-10C)alkyl, O-alkyl, preferably at present —O(2C-10C)alkyl and —S-alkyl, preferably at present —S—(2C-10C)alkyl. In certain embodiments, $Y_3$ is selected from a covalent bond, alkyl, preferably at present (1C-5C) alkyl and phenyl.

In some embodiments, Z- is present or absent. In certain embodiments, wherein $R_1$ and/or $R_4$ is hydrogen, Z- is OH—. In certain embodiments, Z⁻ is any counterion (e.g., one or more counterion), preferably a biocompatible counter ion, such as, by way of non-limiting example, chloride, inorganic or organic phosphate, sulfate, sulfonate, acetate, propionate, butyrate, valerate, caproate, caprylate, caprate, laurate, myristate, palmate, stearate, palmitolate, oleate, linolate, arachidate, gadoleate, vaccinate, lactate, glycolate, salicylate, desamionphenylalanine, desaminoserine, desaminothreonine, E-hydroxycaproate, 3-hydroxybutylrate, 4-hydroxybutyrate or 3-hydroxyvalerate. In some embodiments, when each Y, R and optional fluorine is covalently bonded to a carbon of the selected backbone, any carbons that are not fully substituted are completed with the appropriate number of hydrogen atoms. The numbers m, n, p, q and r represent the mole fraction of each constitutional unit in its block and v and w provide the molecular weight of each block.

In certain embodiments, $A_0$, $A_1$, $A_2$, $A_3$ and $A_4$ are selected from the group consisting of —C—, —C—C—, —C(O)(CR$_{12}$R$_{13}$)$_a$C(O)O—, —O(CR$_{12}$R$_{13}$)$_a$C(O)— and O(CR$_{12}$R$_{13}$)$_b$O; wherein, a is 1-4;
b is 2-4;
$R_1$, $R_2$, $R_3$, $R_4$, $R_5$, $R_6$, $R_7$, $R_8$, $R_9$, $R_{10}$, $R_{11}$, $R_{12}$, and $R_{13}$ are independently selected from the group consisting of hydrogen, (1C-5C)alkyl, (3C-6C)cycloalkyl, (5C-10C)aryl, (4C-10C)heteroaryl, any of which may be optionally substituted with one or more fluorine atoms;

$Y_0$ and $Y_4$ are independently selected from the group consisting of hydrogen, (1C-10C)alkyl, (3C-6C)cycloalkyl, O-(1C-10C)alkyl, —C(O)O(1C-10C)alkyl and phenyl, any of which is optionally substituted with one or more fluorine groups;

$Y_1$ and $Y_2$ are independently selected from the group consisting of a covalent bond, (1C-10C)alkyl-, —C(O)O (2C-10C) alkyl-, —OC(O)(1C-10C)alkyl-, —O(2C-10C)alkyl- and
—S(2C-10C)alkyl-;

$Y_3$ is selected from the group consisting of a covalent bond, (1C-5C)alkyl and phenyl; wherein tetravalent carbon atoms of $A_0$-$A_4$ that are not fully substituted with $R_1$-$R_5$ and $Y_0$-$Y_4$ are completed with an appropriate number of hydrogen atoms;

Z is one or more physiologically acceptable counterions,
m is 0 to about 0.49;
n is about 0.51 to about 1.0; wherein $m+n=1$ p is about 0.2 to about 0.5;
q is about 0.2 to about 0.5; wherein:
p is substantially the same as q;
r is 0 to about 0.6; wherein $p+q+r=1$ v is from about 1 to about 25 kDa, or about 5 to about 25 kDa; and,
w is from about 1 to about 50 kDa, or about 5 to about 50 kDa.

In a specific embodiment,
$A_0$, $A_1$, $A_2$, $A_3$ and $A_4$ are independently selected from the group consisting of —C—C—, —C(O)(C)$_a$C(O)O—, —O(C)$_a$C(O)— and —OC)$_b$O—; wherein,
a is 1-4;
b is 2-4;
$R_1$, $R_2$, $R_3$, $R_4$, $R_5$, $R_6$, $R_7$, $R_8$, $R_9$, $R_{10}$ and $R_{11}$ are independently selected from the group consisting of hydrogen, (1C-5C)alkyl, (3C-6C)cycloalkyl and phenyl, any of which may be optionally substituted with one or more fluorine atoms;

$Y_0$ and $Y_4$ are independently selected from the group consisting of hydrogen, (1C-10C)alkyl, (3C-6C)cycloalkyl, 0-(1C-10C)alkyl, —C(O)O(1C-10C)alkyl and phenyl, any of which is optionally substituted with one or more fluorine groups;

$Y_1$ and $Y_2$ are independently selected from the group consisting of a covalent bond, (1C-10C)alkyl-, —C(O)O (2C-10C) alkyl-, —OC(O)(1C-10C) alkyl-, —O(2C-10C) alkyl- and —S(2C-10C)alkyl-;

$Y_3$ is selected from the group consisting of a covalent bond, (1C-5C)alkyl and phenyl;
wherein tetravalent carbon atoms of $A_0$-$A_4$ that are not fully substituted with $R_1$-$R_5$ and $Y_0$-$Y_4$ are completed with an appropriate number of hydrogen atoms;

Z is a physiologically acceptable counterion,
m is 0 to about 0.49;
n is about 0.51 to about 1.0;
wherein m+n=1
p is about 0.2 to about 0.5;
q is about 0.2 to about 0.5; wherein:
p is substantially the same as q;
r is 0 to about 0.6; wherein $p+q+r=1$ v is from about 5 to about 25 kDa; and
w is from about 5 to about 25 kDa.
In some embodiments,
$A_1$ is —C—C—
$Y_1$ is —C(O)OCH$_2$CH$_2$—;
$R_6$ is hydrogen;
$R_7$ and $R_8$ are each —CH$_3$; and,
$R_2$ is —CH3.
In some embodiments,
$A_2$ is —C—C—;
$Y_2$ is —C(O)OCH$_2$CH$_2$—;
$R_9$ is hydrogen;
$R_{10}$ and $R_{11}$ are each —CH$_3$; and, $R_3$ is —CH$_3$.
In some embodiments,
$A_3$ is —C—C—;
$R_4$ is CH$_3$CH$_2$CH$_2$—;
$Y_3$ is a covalent bond; and
Z is a physiologically acceptable anion.
In some embodiments,
$A_4$ is —C—C—;
$R_5$ is selected from the group consisting of hydrogen and
—CH$_3$; and,
$Y_4$ IS —C(O)O(CH$_2$)$_3$CH$_3$.
In some embodiments,
$A_0$ is C—C—
$R_1$ is selected from the group consisting of hydrogen and (1C-3C)alkyl; and,
$Y_0$ is selected from the group consisting of —C(O)O(1C-3C)alkyl.
In some embodiments, m is 0.
In some embodiments, r is 0.
In some embodiments, m and r are both 0.

In various embodiments described herein, constitutional units, that are cationic or positively charged at physiological pH (including, e.g., certain hydrophilic constitutional units) described herein comprise one or more amino groups, alkylamino groups, guanidine groups, imidazolyl groups, pyridyl groups, or the like, or the protonated, alkylated or otherwise charged forms thereof. In some embodiments, constitutional units that are cationic at normal physiological pH that are utilized herein include, by way of non-limiting example, monomeric residues of dialkylaminoalkylmethacrylates (e.g., DMAEMA). In various embodiments described herein, constitutional units, that are anionic or negatively charged at physiological pH (including, e.g., certain hydrophilic constitutional units) described herein comprise one or more acid group or conjugate base thereof, including, by way of non-limiting example, carboxylate, sulfonamide, boronate, phosphonate, phosphate, or the like. In some embodiments, constitutional units that are anionic or negatively charged at normal physiological pH that are utilized herein include, by way of non-limiting example, monomeric residues of acrylic acid, alkyl acrylic acid (e.g., methyl acrylic acid, ethyl acrylic acid, propyl acrylic acid, etc.), or the like. In various embodiments described herein, hydrophilic constitutional units that are neutral at physiologic pH comprise one or more hydrophilic group, e.g., hydroxy, polyoxylated alkyl, polyethylene glycol, polypropylene glycol, thiol, or the like. In some embodiments, hydrophilic constitutional units that are neutral at normal physiological pH that are utilized herein include, by way of non-limiting example, monomeric residues of PEGylated acrylic acid, PEGylated methacrylic acid, hydroxyalkylacrylic acid, hydroxyalkylalkacrylic acid (e.g, HPMA), or the like. In various embodiments described herein, hydrophilic constitutional units that are zwitterionic at physiologic pH comprise an anionic or negatively charged group at physiologic pH and a cationic or positively charged group at physiologic pH. In some embodiments, hydrophilic constitutional units that are zwitterionic at normal physiological pH that are utilized herein include, by way of non-limiting example, monomeric residues of comprising a phosphate group and an ammonium group at physiologic pH, such as set forth in U.S. Pat. No. 7,300,990, which is hereby incorporated herein for such disclosure, or the like.

In certain embodiments, polymers provided herein further comprise one or more constitutional unit comprising a conjugatable or functionalizable side chain (e.g., a pendant group of a monomeric residue). In some instances, a conjugatable or functionalizable side chain is a group bearing one or more reactive groups that can be used for post-polymerization introduction of additional functionalities via know in the art chemistries, for example, "click" chemistry (for example of "click" reactions, see Wu, P.; Fokin, V. V. Catalytic Azide-Alkyne Cycloaddition: Reactivity and Applications. *Aldrichim. Acta,* 2007, 40, 7-17). In certain embodiments, conjugatable or functionalizable side chains provided herein comprise one or more of any suitable activated group, such as but not limited to N-hydroxysuccinimide (NHS)ester, HOBt (1-hydroxybenzotriazole) ester, p-nitrophenyl ester, tetrafluorophenyl ester, pentafluorophenyl ester, pyridyl disulfide group or the like.

Provided in certain embodiments, the block copolymer is a diblock copolymer, having the chemical formula (at normal physiological or about neutral pH) of Formula IV1:

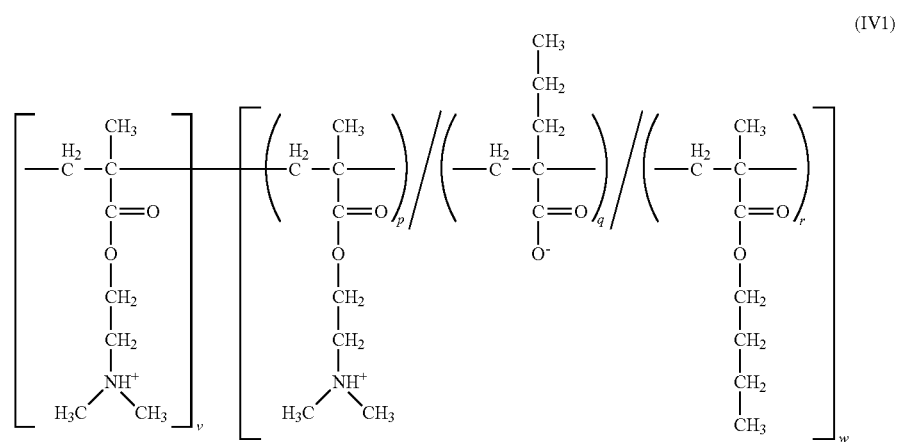

In certain instances, the constitutional units of the compound IV1 are as shown within the square bracket on the left and the curved brackets on the right and they are derived from the monomers:

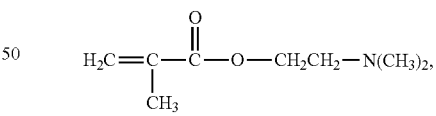

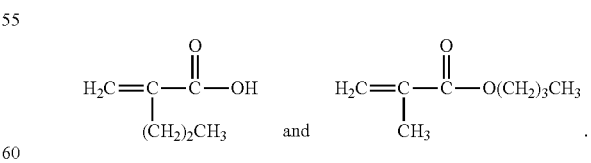

The letters p, q and r represent the mole fraction of each constitutional unit within its block. The letters v and w represent the molecular weight (number average) of each block in the diblock copolymer.

Provided in some embodiments, a compound provided herein is a compound having the structure:

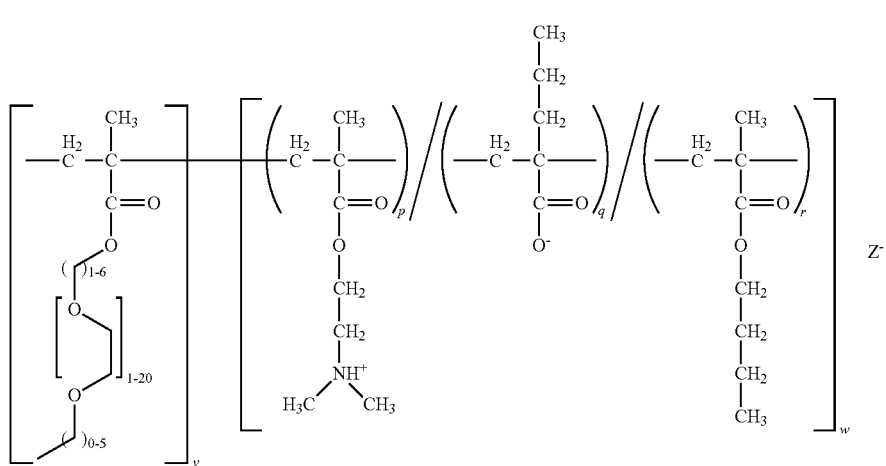

(IV2)

As discussed above, letters p, q and r represent the mole fraction of each constitutional unit within its block. The letters v and w represent the molecular weight (number average) of each block in the diblock copolymer.
In some embodiments, provided herein are the following polymers:

$[DMAEMA]_v\text{-}[B_r\text{-}/\text{-}P_q\text{-}/\text{-}D_p]_w$,      IV3

$[PEGMA]_v\text{-}[B_r\text{-}/\text{-}P_q\text{-}/\text{-}D_p]_w$      IV4

$[PEGMA_m\text{-}/\text{-}DMAEMA_n]_v\text{-}[B_r\text{-}/\text{-}P_q\text{-}/\text{-}D_p]_w$      IV5

$[PEGMA_m\text{-}/\text{-}MAA(NHS)_n]_v\text{-}[B_r\text{-}/\text{-}P_q\text{-}/\text{-}D_p]_w$      IV6

$[DMAEMA_m\text{-}/\text{-}MAA(NHS)_n]_v\text{-}[B_r\text{-}/\text{-}P_q\text{-}/\text{-}D_p]_w$      IV7

$[HPMA_m\text{-}/\text{-}PDSM_n]_v\text{-}[B_r\text{-}/\text{-}P_q\text{-}/\text{-}D_p]_w$      IV8

$[PEGMA_m\text{-}/\text{-}PDSM_n]_v\text{-}[B_r\text{-}/\text{-}P_q\text{-}/\text{-}D_p]_w$      IV9

In some embodiments, B is butyl methacrylate residue; P is propyl acrylic acid residue; D and DMAEMA are dimethylaminoethyl methacrylate residue; PEGMA is polyethyleneglycol methacrylate residue (e.g., with 1-20 ethylene oxide units, such as illustrated in compound IV2, or 4-5 ethylene oxide units, or 7-8 ethylene oxide units); MAA (NHS) is methylacrylic acid-N-hydroxy succinamide residue; HPMA is N-(2-hydroxypropyl) methacrylamide residue; and PDSM is pyridyl disulfide methacrylate residue. In certain embodiments, the terms m, n, p, q, r, w and v are as described herein. In specific embodiments, w is about 1x to about 5x v.

Compounds of Formulas IV1-IV9 are examples of polymers provided herein comprising a variety of constitutional unit(s) making up the first block of the polymer. In some embodiments, the constitutional unit(s) of the first block are varied or chemically treated in order to create polymers where the first block is or comprises a constitutional unit that is neutral (e.g., PEGMA), cationic (e.g., DMAEMA), anionic (e.g., PEGMA-NHS, where the NHS is hydrolyzed to the acid, or acrylic acid), ampholytic (e.g., DMAEMA-NHS, where the NHS is hydrolyzed to the acid), or zwiterrionic (for example, poly[2-methacryloyloxy-2'trimethyl-ammoniumethyl phosphate]). In some embodiments, polymers comprising pyridyl disulfide functionality in the first block, e.g., [PEGMA-PDSM]-[B-P-D], that can be and is optionally reacted with a thiolated siRNA to form a polymer-siRNA conjugate.

In a specific embodiment, a compound of Formula IV3 is a polymer of the P7 class, as described herein, and has the molecular weight, polydispersity, and monomer composition as set forth in Table 1.

TABLE 1

Molecular weights, polydispersities, and monomer compositions for a species of P7 polymer

| Polymer Class | P7 |
|---|---|
| Mn of "v" block[a] | 9100 |
| Mn of "w" block[a] | 11300 |
| PDI | 1.45 |
| Theoretical % BMA residue of "w" block | 40 |
| Theoretical % PPA residue of "w" block | 30 |
| Theoretical % DMAEMA residue of "w" block | 30 |
| Experimental % BMA residue 4 "w" block[b] | 48 |
| Experimental % PPA residue of "w" block[b] | 29 |
| Experimental % DMAEMA residue of "w" block[b] | 23 |

[a]As determined by SEC Tosoh TSK-GEL R-3000 and R-4000 columns (Tosoh Bioscience, Mongomeryville, PA) connected in series to a Viscotek GPCmax VE2001 and refractometer VE3580 (Viscotek, Houston, TX). HPLC-grade DMF containing 0.1 wt % LiBr was used as the mobile phase. The molecular weights of the synthesized copolymers were determined using a series of poly(methyl methacrylate) standards.
[b]As determined by $^1$H NMR spectroscopy (3 wt % in CDCL$_3$; Bruker DRX 499)

In some specific embodiments, a polymer of Formula IV3 is a polymer of the P7 class according to Table 2. In some specific embodiments, a polymer of Formula IV3 is a polymer of the P7 class called P7v6. PRx0729v6 is used interchangeably with P7v6 in this application and in various priority applications.

TABLE 2

| Polymer | Structure | Block Ratio (w/v) | Particle Size (nm) |
|---|---|---|---|
| PRx-1 | $[D]_{11.3K}\text{—}[B_{50}\text{—}P_{30}\text{—}D_{20}]_{20.7K}$ | 1.83 | 41 |
| PRx-2 | $[D]_{14.5K}\text{—}[B_{57}\text{—}P_{23}\text{—}D_{20}]_{26.4K}$ | 1.82 | 49 |

TABLE 2-continued

| Polymer | Structure | Block Ratio (w/v) | Particle Size (nm) |
|---|---|---|---|
| PRx-3 | $[D]_{11.5K}$—$[B_{35}$—$P_{27}$—$D_{38}]_{33.4K}$ | 2.92 | 60 |
| PRx-4 | $[D]_{10.7K}$—$[B_{30}$—$P_{27}$—$D_{23}]_{33.8K}$ | 3.16 | 50 |
| PRx-5 | $[D]_{10.7K}$—$[B_{46}$—$P_{31}$—$D_{29}]_{32.2K}$ | 3.00 | 59 |
| PRx-6 | $[D]_{14.5K}$—$[B_{53}$—$P_{31}$—$D_{16}]_{67.0K}$ | 4.62 | 115 |

Core Block

Provided in certain embodiments herein, the core block of a membrane destabilizing block copolymer described herein is or comprises a pH dependent membrane destabilizing hydrophobe. In certain embodiments, the core block of the membrane destabilizing block copolymer is at least partially, substantially, or predominantly hydrophobic.

In some embodiments, the core block of a membrane destabilizing block copolymer described herein comprises a first chargeable species that is anionic at about neutral pH. In certain embodiments, the core block of a membrane destabilizing block copolymer described herein comprises a first chargeable species that is anionic at about neutral pH, the core block being a copolymer block. In some embodiments, the core block of a membrane destabilizing block copolymer described herein comprises a first chargeable species that is anionic at about neutral pH, the first chargeable species being hydrophobically shielded (e.g., by being in proximity of the polymer backbone of a polymer block comprising pendant hydrophobic moieties). In certain embodiments, the core block of a membrane destabilizing block copolymer described herein comprises a first chargeable species that is anionic at about neutral pH and a second chargeable species that is cationic at about neutral pH.

In some embodiments, the core block of a membrane destabilizing polymer described herein comprises at least one first chargeable species, group, or monomeric unit. In specific embodiments, the first chargeable species, group, or monomeric unit is charged or chargeable to an anionic species, group, or monomeric unit. It is to be understood that such core blocks include species, groups, and/or monomeric units wherein none, some, or all of the chargeable species, groups, or monomeric units are charged.

In certain embodiments, the core block of a membrane destabilizing polymer described herein comprises at least one first chargeable species, group, or monomeric unit, and at least one second chargeable species, group, or monomeric unit. In some instances, the first chargeable species, group, or monomeric unit is as described above and the second chargeable species, group, or monomeric unit is charged or chargeable to a cationic species, group, or monomeric unit. In some embodiments, the core block of a membrane destabilizing polymer described herein comprises at least one first chargeable species, group, or monomeric unit; at least one second chargeable species, group, or monomeric unit; and at least one additional species, group, or monomeric unit. In specific embodiments, the additional species, group, or monomeric unit is a non-chargeable species, group, or monomeric unit. In certain embodiments, the additional species, group, or monomeric unit is a hydrophobic species, group, or monomeric unit.

In certain embodiments, where the core block comprises at least one anionic chargeable species, group, or monomeric unit and at least one cationic chargeable species, group, or monomeric unit, the ratio of the number of the at least one anionic chargeable species, group, or monomeric unit to the number of the at least one cationic chargeable species, group, or monomeric unit is about 1:10 to about 10:1, about 1:8 to about 8:1, about 1:6 to about 6:1, about 1:4 to about 4:1, about 1:2 to about 2:1, about 3:2 to about 2:3, or is about 1:1. In some embodiments, the core block comprises at least one anionic chargeable species, group, or monomeric unit that is anionically charged and at least one cationic chargeable species, group, or monomeric unit that is cationically charged, wherein the ratio of the number of anionically charged species, group, or monomeric unit to the number of cationically charged species, group, or monomeric unit present on the core block is about 1:10 to about 10:1, about 1:8 to about 8:1, about 1:6 to about 6:1, about 1:4 to about 4:1, about 1:2 to about 2:1, about 3:2 to about 2:3, or is about 1:1.

In some embodiments, the ratio, at about a neutral pH (e.g., at a pH of about 7.4), of the number of the at least one anionic chargeable species, group, or monomeric unit to the number of the at least one cationic chargeable species, group, or monomeric unit is about 1:10 to about 10:1, about 1:8 to about 8:1, about 1:6 to about 6:1, about 1:4 to about 4:1, about 1:2 to about 2:1, about 2:3 to about 3:2, about 1:1.1 to about 1.1:1, or is about 1:1. In some embodiments, the core block comprises at least one anionic chargeable species, group, or monomeric unit that is anionically charged and at least one cationic chargeable species, group, or monomeric unit that is cationically charged, wherein the ratio, at about a neutral pH (e.g., at a pH of about 7.4), of the number of anionically charged species, groups, or monomeric units to the number of cationically charged species, groups, or monomeric units present on the core block is about 1:10 to about 10:1, about 1:8 to about 8:1, about 1:6 to about 6:1, about 1:4 to about 4:1, about 1:2 to about 2:1, about 2:3 to about 3:2, about 1:1.1 to about 1.1:1, or is about 1:1. In specific embodiments, the ratio of positively charged species, groups, or monomeric units present on the core block to negatively charged species, groups, or monomeric units in the core is about 1:4 to about 4:1 at about neutral pH. In more specific embodiments, the ratio of positively charged species, groups, or monomeric units present on the core block to negatively charged species, groups, or monomeric units in the core is about 1:2 to about 2:1 at about neutral pH. In specific embodiments, the ratio of positively charged species, groups, or monomeric units present on the core block to negatively charged species, groups, or monomeric units in the core is about 1:1.1 to about 1.1:1 at about neutral pH.

In specific embodiments, the first chargeable monomeric unit is Brønsted acid. In certain instances, as used herein, a chargeable species, group, or monomeric unit includes species, groups, and/or monomeric units wherein addition or removal of a proton (e.g., in a pH dependent manner), provides a cationic or anionic, respectively, species, group, or monomeric unit.

In some embodiments, the first chargeable species, groups, or monomeric units present in the core block are species, groups, or monomeric units that are at least 50%, at least 60%, at least 70%, at least 80%, at least 85%, or at least 95% negatively charged at about neutral pH (e.g., at a pH of about 7.4). In specific embodiments, these first chargeable species, groups, or monomeric units are charged by loss of an H$^+$, to an anionic species at about neutral pH. In further or alternative embodiments, the first chargeable species, groups, or monomeric units present in the core block are species, groups, or monomeric units that are at least 20%, at least 30%, at least 40%, at least 50%, at least 60%, at least 70%, at least 80%, at least 85%, or at least 95% neutral or non-charged at a slightly acidic pH (e.g., a pH of about 6.5, or less; about 6.2, or less; about 6, or less; about 5.9, or less; about 5.8, or less; or about endosomal pH).

In some embodiments, the first chargeable species or group is, by way of non-limiting example, a carboxylic acid, anhydride, sulfonamide, sulfonic acid, sulfinic acid, sulfuric acid, phosphoric acid, phosphinic acid, boric acid, phosphorous acid, or the like. Similarly, in certain embodiments, a first chargeable monomeric unit useful herein is a monomeric unit that comprises a carboxylic acid, anhydride, sulfonamide, sulfonic acid, sulfinic acid, sulfuric acid, phosphoric acid, phosphinic acid, boric acid, phosphorous acid, or the like. In specific embodiments, a first chargeable monomeric unit useful herein is a $(C_2-C_8)$alkylacrylic acid.

In some embodiments, the second chargeable species, groups, or monomeric units present in the core block are species, groups, or monomeric units that are at least 20%, at least 30%, at least 40%, at least 50%, at least 60%, at least 70%, at least 80%, at least 85%, or at least 95% positively charged at about neutral pH (e.g., at a pH of about 7.4). In specific embodiments, these second chargeable species, groups, or monomeric units are charged by addition of an $H^+$, to a cationic species. In further or alternative embodiments, the second chargeable species, groups, or monomeric units present in the core block are species, groups, or monomeric units that are at least 20%, at least 30%, at least 40%, at least 50%, at least 60%, at least 70%, at least 80%, at least 85%, or at least 95% positively charged at a slightly acidic pH (e.g., a pH of about 6.5, or less; about 6.2, or less; about 6, or less; about 5.9, or less; about 5.8, or less; or about endosomal pH).

In specific embodiments, the second chargeable monomeric unit is Brønsted base. In certain embodiments, the second chargeable species or group is an amine (including, e.g., non-cyclic and cyclic amines). In some embodiments, the second chargeable monomeric unit is a monomeric unit comprising an amine, such as, by way of non-limiting example, N,N-di$(C_1-C_6)$alkyl-amino$(C_1-C_6)$alkyl-ethacrylate, N,N-di$(C_1-C_6)$alkyl-amino$(C_1-C_6)$alkyl-methacrylate, or N,N-di$(C_1-C_6)$alkyl-amino$(C_1-C_6)$alkyl-acrylate. In some embodiments, the second chargeable monomeric unit comprises a nitrogen heterocycle, e.g. an imidazole, a pyridine, a piperidine, a pyrimidine, or the like.

In certain embodiments, the core segment (e.g., core block) of a membrane destabilizing block copolymer described herein is hydrophobic and comprises one or more types of chargeable species. In specific embodiments, the chargeable species is chargeable to a cationic species. The micellic assemblies described herein, comprising chargeable species include micellic assemblies wherein each of chargeable species are, each individually present in the micellic assembly in a charged state or a non-charged state. Furthermore, wherein the micellic assemblies described herein comprise a population of a first chargeable species, a population of second chargeable species and/or a population of any additional chargeable species, the micellic assemblies described herein include micellic assemblies wherein each of the population of first, second, and any additional chargeable species are, each individually, present in the micellic assembly in a completely charged state, a partially charged state or a completely non-charged state.

In some embodiments, the anionic chargeable species is any organic or inorganic acid residue that is optionally present, either as a protected species, e.g., an ester, or as the free acid, in the selected polymerization process. In some embodiments, the anionic chargeable species is a weak acid, such as but not limited to the following groups: boronic acid, sulfonamide, phosphonic acid, arsonic acid, phosphinic acid, phosphate, carboxylic acid, xanthenes, tetrazole or their derivatives (e.g. esters). In certain embodiments monomers such as maleic-anhydride, (Scott M. Henry, Mohamed E. H. El-Sayed, Christopher M. Pine, Allan S. Hoffman, and Patrick S. Stayton pH-Responsive Poly(styrene-alt-maleic anhydride) Alkylamide Copolymers for Intracellular Drug Delivery. *Biomacromolecules* 2006, 7, 2407-2414) are used for introduction of first chargeable species by post-polymerization hydrolysis of the maleic anhydride monomeric units. In specific embodiments, a chargeable species that are anionic at normal physiological pH are carboxylic acids such as, but not limited to, 2-propyl acrylic acid or, more accurately, the constitutional unit derived from it, 2-propylpropionic acid, $—CH_2C((CH_2)_2CH_3)(COOH)$ (PAA).

In some embodiments, the chargeable species is cationic. In certain embodiments, the chargeable species is cationic at physiological pH. In specific embodiments, cationic at physiological pH species are nitrogen species such as ammonium, $—NRR'R''$, guanidinium ($—NRC(=NWH)+NR''R''$, including canonical forms), wherein the R groups are independently hydrogen, alkyl, cycloalkyl or aryl or two R groups bonded to the same or adjacent nitrogen atoms may be also be joined to one another to form a heterocyclic species such as but not limited to pyrrole, imidazole, pyrimidine, or indole.

In some embodiments, the chargeable species is present in a zwitterionic monomeric units (i.e., wherein an anionic and a cationic chargeable species are present in the same monomeric unit).

In certain embodiments, the core block comprises at least one non-chargeable monomeric unit, group, or species. In some embodiments, the non-chargeable monomeric unit is hydrophobic or comprises a hydrophobic group or species. In certain embodiments, the hydrophobic group has a 7t value of about 1, or more; about 2, or more; about 3, or more; about 4, or more; about 5, or more; or the like. In specific embodiments, the non-chargeable monomeric unit is, by way of non-limiting example, a $(C_2-C_8)$alkyl-ethacrylate, a $(C_2-C_8)$alkyl-methacrylate, or a $(C_2-C_8)$alkyl-acrylate.

In some embodiments, the block copolymers comprise a plurality of hydrophobic species. In some embodiments, the block copolymer comprises hydrophobic monomeric units. In certain embodiments, the hydrophobic monomeric unit is a vinyl substituted aromatic or heteroaromatic compound. In further specific embodiments, hydrophobic monomers are alkyl (alkyl)acrylates. In specific embodiments, the hydrophobic monomer is a styrene derivative.

In some embodiments, provided herein the core block of the membrane destabilizing block copolymer has a number average molecular weight (Mn) of about 2,000 dalton to about 250,000 dalton; 2,000 dalton to about 100,000 dalton; about 5,000 dalton to about 100,000 dalton; about 5,000 dalton to about 50,000 dalton; or about 10,000 dalton to about 50,000 dalton.

Shell Block

In some embodiments, the shell block of a membrane destabilizing polymer described herein is hydrophilic. In some embodiments, the shell block of a membrane destabilizing polymer described herein is hydrophilic and non-charged at an approximately physiological pH, e.g. pH 7.4. In some embodiments, the shell block of a membrane destabilizing polymer described herein is hydrophilic and charged at an approximately physiological pH, e.g. pH 7.4. In some embodiments, the shell block of the membrane destabilizing polymer comprises at least one hydrophilic (e.g., non-charged, cationic, anionic, or zwitterionic) species, group, or monomeric unit. In specific embodiments, the shell block of the membrane destabilizing polymer comprises at least one chargeable species, group, or monomeric unit. In specific embodiments, the chargeable species, group, or monomeric unit is charged or chargeable to a cationic species, group, or monomeric. In other specific embodiments, the chargeable species, group, or monomeric unit is charged or chargeable to an anionic species, group, or monomeric unit. In specific embodiments, the chargeable species, group, or monomeric unit is charged or chargeable to a zwitterionic species, group, or monomeric. It is to be understood that such shell blocks include species, groups, and/or monomeric units wherein none, some, or all of the chargeable species, groups, or monomeric units are charged.

In some embodiments, a shell block of a membrane destabilizing polymer is temperature independent.

In specific embodiments, the shell block of one or more of the membrane destabilizing block copolymers is non-charged at about neutral pH (e.g., at a pH of about 7.4). In specific embodiments, the shell block of one or more of the membrane destabilizing block copolymers is also non-charged at about endosomal pH.

In specific embodiments, the shell block of one or more of the membrane destabilizing block copolymers is polycationic at about neutral pH (e.g., at a pH of about 7.4). In specific embodiments, the shell block of one or more of the membrane destabilizing block copolymers is also polycationic at about endosomal pH.

In specific embodiments, the shell block of one or more of the membrane destabilizing block copolymers is polyanionic at about neutral pH (e.g., at a pH of about 7.4). In specific embodiments, the shell block of one or more of the membrane destabilizing block copolymers is also polyanionic at about endosomal pH.

In specific embodiments, the shell block of one or more of the membrane destabilizing block copolymers is zwitterionic at about neutral pH (e.g., at a pH of about 7.4). In specific embodiments, the shell block of one or more of the membrane destabilizing block copolymers is also zwitterionic at about endosomal pH.

In some embodiments, the shell block of one or more of the membrane destabilizing block copolymers is a homopolymeric block. In certain embodiments, a homopolymeric shell block comprises cationic chargeable monomeric units, wherein some of the cationic chargeable monomeric units are cationic and wherein others of the cationic chargeable monomeric units are non-charged. In further or alternative embodiments, the shell block of one or more of the membrane destabilizing block copolymers is heteropolymeric. In specific embodiments, a heteropolymeric shell block comprises cationic chargeable monomeric units and non-chargeable monomeric units. In certain embodiments, a homopolymeric shell block comprises anionic chargeable monomeric units, wherein some of the anionic chargeable monomeric units are anionic and wherein others of the anionic chargeable monomeric units are non-charged. In further or alternative embodiments, the shell block of one or more of the membrane destabilizing block copolymers is heteropolymeric. In specific embodiments, a heteropolymeric shell block comprises anionic chargeable monomeric units and non-charged monomeric units. Non-charged monomeric units include, e.g., residues of polyoxylated olefins, such as PEGMA, residues of hydroxy-alkyl olefins, such as HPMA, residues of thiol-alkyl olefins or the like.

In some embodiments, the chargeable species, groups, or monomeric units present in the shell block of one or more of the membrane destabilizing block copolymers are species, groups, or monomeric units that are at least 20%, at least 30%, at least 40%, at least 50%, at least 60%, at least 70%, at least 80%, at least 85%, or at least 95% positively charged at about neutral pH (e.g., at a pH of about 7.4). In specific embodiments, these chargeable species, groups, or monomeric units in the shell block of one or more of the membrane destabilizing block copolymers are charged by addition of an to a cationic species. In further or alternative embodiments, the chargeable species, groups, or monomeric units in the shell block of one or more of the membrane destabilizing block copolymers are species, groups, or monomeric units that are at least 20%, at least 30%, at least 40%, at least 50%, at least 60%, at least 70%, at least 80%, at least 85%, or at least 95% positively charged at a slightly acidic pH (e.g., a pH of about 6.5, or less; about 6.2, or less; about 6, or less; about 5.9, or less; about 5.8, or less; or about endosomal pH).

In some embodiments, the anionic chargeable species is any organic or inorganic acid residue that is optionally present, either as a protected species, e.g., an ester, or as the free acid, in the selected polymerization process. In some embodiments, the anionic chargeable species is a weak acid, such as but not limited to the following groups: boronic acid, sulfonamide, phosphonic acid, arsonic acid, phosphinic acid, phosphate, carboxylic acid, xanthenes, tetrazole or their derivatives (e.g. esters). In certain embodiments monomers such as maleic-anhydride, (Scott M. Henry, Mohamed E. H. El-Sayed, Christopher M. Pirie, Allan S. Hoffman, and Patrick S. Stayton pH-Responsive Poly(styrene-alt-maleic anhydride) Alkylamide Copolymers for Intracellular Drug Delivery. *Biomacromolecules* 2006, 7, 2407-2414) are used for introduction of first chargeable species by post-polymerization hydrolysis of the maleic anhydride monomeric units. In specific embodiments, a chargeable species that are anionic at normal physiological pH are carboxylic acids such as, but not limited to, 2-propyl acrylic acid or, more accurately, the constitutional unit derived from it, 2-propylpropionic acid, $-CH_2C((CH_2)_2CH_3)(COOH)$ (PAA).

In some embodiments, the shell block is cationic at or near physiological pH (e.g., the pH of circulation human plasma). In some embodiments, the shell block comprises a polycation. In some embodiments, the shell block is attached to a therapeutic agent (e.g., a polynucleotide, such as siRNA) which is a polyanion comprising x anions, and the polycationic shell block comprises about 0.6 x, about 0.7 x, about 0.8 x, about 0.9 x, about 1.0 x, about 1.1 x cations, or more. In specific embodiments, the therapeutic agent (e.g., a polynucleotide, such as siRNA) is polyanionic comprising x anions, and the polycationic shell block comprises about 0.7-x cations, or more.

In some embodiments, the chargeable species is cationic. In certain embodiments, the chargeable species is cationic at physiological pH. In specific embodiments, cationic at physiological pH species are nitrogen species such as ammonium, $-NRR'R''$, guanidinium ($-NRC(=NR'H)^+NR''R''$, including canonical forms) wherein the R groups are independently hydrogen, alkyl, cycloalkyl or aryl or two R groups bonded to the same or adjacent nitrogen atoms may be also be joined to one another to form a heterocyclic species such as but not limited to pyrrole, imidazole, or indole. In some embodiments, the shell block is a nucleic-acid binding polyamide, an intercalator, or a duplex-or triplex-forming oligonucleotide. In certain instances, the shell block is optionally the α-end block, or the ω-end block of the block copolymer (e.g., membrane destabilizing block copolymer). Likewise, the core block is optionally the α-end block, or the ω-end block of the block copolymer (e.g., membrane destabilizing block copolymer).

In some embodiments, the chargeable species is present in a zwitterionic monomeric units (i.e., wherein an anionic and a cationic chargeable species are present in the same monomeric unit).

In specific embodiments, the chargeable monomeric unit of the shell block of the one or more of the membrane destabilizing block copolymers is Brønsted base. In certain embodiments, the chargeable species or group of the shell block is an amine (including, e.g., non-cyclic and cyclic amines). In some embodiments, the chargeable monomeric unit of the shell block is a monomeric unit comprising an amine, such as, by way of non-limiting example, N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, or N,N-di($C_1$-$C_6$)alkyl-amino($C_1$-$C_6$)alkyl-acrylate. In some embodiments, the chargeable monomeric unit of the shell block is a monomeric unit comprising a nitrogen heterocycle, e.g., an imidazole or pyridine.

In some embodiments, provided herein the shell block of the membrane destabilizing block copolymer has a number average molecular weight (Mn) of about 1,000 dalton to about 200,000 dalton; 1,000 dalton to about 100,000 dalton; about 3,000 dalton to about 100,000 dalton; about 5,000 dalton to about 50,000 dalton; about 5,000 dalton to about 25,000 dalton; or about 5,000 dalton to about 20,000 dalton.

In specific embodiments, the shell block of the membrane destabilizing block copolymer is non-charged and hydrophilic at about neutral pH (e.g., at a pH of about 7.4). In certain embodiments, the hydrophilic shell block is free or substantially free of chargeable groups. In some embodiments, a non-charged hydrophilic shell block comprises or is polyethylene glycol (PEG), polyethylene oxide (PEO) or the like.

In certain embodiments, the shell block of the membrane destabilizing block copolymer comprises a functionalizing group (e.g., a solubilizing group). In specific embodiments, the functionalizing group is a polyethylene glycol (PEG) group. In certain embodiments, the shell block comprises a polyethylene gylcol (PEG) groups, chains or blocks with molecular weights of approximately from 1,000 to approximately 30,000. In some embodiments, the PEG is a part of (e.g., incorporated into) the shell block chain. In certain embodiments, the PEG is incorporated into the shell block chain during polymerization. In some embodiments, the shell block of one or more of the membrane destabilizing block copolymers is PEG. In certain embodiments, provided herein are micellic assemblies comprising a first membrane destabilizing block copolymer with a polycationic shell block, and a second membrane destabilizing block copolymer with a PEG shell block. In certain embodiments, one or more monomeric units of the shell block are substituted or functionalized with a PEG group. In some embodiments, PEG is conjugated to block copolymer ends groups, or to one or more pendant modifiable group present in a micellic assembly provided herein. In some embodiments, PEG residues are conjugated to modifiable groups within the hydrophilic segment or block (e.g., a shell block) of a polymer (e.g., block copolymer) of a micellic assembly provided herein. In certain embodiments, a monomer comprising a PEG residue is co-polymerized to form the hydrophilic portion of the polymer forming the micellic assembly provided herein Shielding Hydrophilic Segment/Block In certain embodiments, the micellic assemblies described herein comprise one or more shielding agents. In some embodiments, the polynucleotide carrier block/segment comprises a PEG substituted monomeric unit (e.g., the PEG is a side chain and does not comprise the backbone of the polynucleotide carrier block). In some instances, one or more of the polymers (e.g., block copolymers) utilized in the micellic assemblies described herein comprise polyethyleneglycol (PEG) chains or blocks with molecular weights of approximately from 1,000 to approximately 30,000. In some embodiments, PEG is conjugated to polymer ends groups, or to one or more pendant modifiable group present in a polymer of a micellic assembly provided herein. In some embodiments, PEG residues are conjugated to modifiable groups within the hydrophilic segment or block (e.g., a shell block) of a polymer (e.g., block copolymer) of a micellic assembly provided herein. In certain embodiments, a monomer comprising a PEG residue of 2-20 ethylene oxide units is co-polymerized to form the hydrophilic portion of the polymer forming a micellic assembly provided herein.

In some instances a shielding agent enhances the stability of the therapeutic agent (e.g., polynucleotide or peptide, etc.) against enzymatic digestion in plasma. In some instances, a shielding agent reduces toxicity of micellic assemblies described herein (e.g., block copolymer attached to polynucleotides). In some embodiments, a shielding agent comprises a plurality of neutral hydrophilic monomeric residues. In some instances, a shielding polymer is covalently coupled to a membrane destabilizing block copolymer through an end group of the polymer. In some embodiments, a shielding agent is a covalently coupled pendant moiety attached to one or more monomeric residues of the polymer. In some embodiments, a plurality of monomeric residues in a micellic assembly described herein comprise pendant shielding species (e.g., a polyethylene glycol (PEG) oligomer (e.g., having 20 or less repeat units) or polymer (e.g, having more than 20 repeat units)) covalently coupled through a functional group to the polyethylene glycol oligomer or polymer. In some instances, a block copolymer comprises a polyethylene gylcol (PEG) oligomer or polymer covalently coupled to the alpha end or the omega end of the membrane destabilizing block of the copolymer.

In certain embodiments, the polynucleotide carrier block/segment comprises a monomeric unit that serves to shield, at least in part, the charge (e.g., cationic charges) on the polynucleotide carrier block/segment. In particular embodiments, the shielding arises, at least in part, form a pendant moiety on the monomeric unit that comprises, at least part, of the polynucleotide carrier block/segment. Such shielding optionally lowers the cellular toxicity from excessive charges in this segment.

Therapeutic Agents

Provided in certain embodiments herein is a micellic assembly comprising at least one research reagent, at least one diagnostic agent, at least one therapeutic agent, or a combination thereof. In some embodiments, such therapeutic agents are present in the shell of the micellic assembly, in the core of the micellic assembly, on the surface of the micellic assembly, or a combination thereof.

In various embodiments, research reagents, diagnostic agents, and/or therapeutic agents are attached to the micellic assembly or membrane destabilizing block copolymers thereof in any suitable manner. In specific embodiments, attachment is achieved through covalent bonds, non-covalent interactions, static interactions, hydrophobic interactions, or the like, or combinations thereof. In some embodiments, the research reagents, diagnostic agents, and/or therapeutic agents are attached to a shell block of membrane destabilizing block copolymers. In certain embodiments, the research reagents, diagnostic agents, or therapeutic agents form the shell block of a membrane destabilizing block copolymer. In some embodiments, the research reagents, diagnostic agents, or therapeutic agents are in the shell of the micellic assembly.

In some embodiments, provided herein is a micellic assembly comprising a first therapeutic agent in the shell of the micellic assembly and a second therapeutic agent in the core of the micellic assembly. In specific embodiments, the first therapeutic agent is a polynucleotide. And the second therapeutic agent is a hydrophobic drug. In certain embodiments, provided herein is a micellic assembly comprising a hydrophobic drug (e.g., small molecule hydrophobic drug) in the core of the micellic assembly.

In certain embodiments, provided herein is a micellic assembly comprising at least 1-5, 5-250, 5-1000, 250-1000, at least 2, at least 5, at least 10, at least 20, or at least 50 therapeutic agents. In some embodiments, provided herein is a composition comprising a plurality of micellic assemblies described herein, wherein the micellic assemblies therein comprise, on average, at least 1-5, 5-250, 5-1000, 250-1000, at least 2, at least 5, at least 10, at least 20, or at least 50 therapeutic agents.

In some embodiments, therapeutic agents, diagnostic agents, etc., are selected from, by way of non-limiting example, at least one nucleotide (e.g., a polynucleotide), at least one carbohydrate or at least one amino acid (e.g., a peptide). In specific embodiments, the therapeutic agent is a polynucleotide, an oligonucleotide, a gene expression modulator, a knockdown agent, an siRNA, an RNAi agent, a dicer substrate, an miRNA, an shRNA, an antisense oligonucleotide, or an aptamer. In other specific embodiments, the therapeutic agent is an aiRNA (Asymmetric RNA duplexes mediate RNA interference in mammalian cells. Xiangao Sun, Harry A Rogoff, Chiang J Li *Nature Biotechnology* 26, 1379-1382 (2008)). In certain embodiments, the therapeutic agent is a protein, peptide, dominant-negative protein, enzyme, antibody, or antibody fragment. In some embodiments, the therapeutic agent is a carbohydrate, or a small molecule with a molecular weight of greater than about 500 Daltons.

In certain embodiments, one or more of the plurality of membrane destabilizing block copolymers is attached to a therapeutic agent. In some embodiments, one or more of the plurality of membrane destabilizing block copolymers is attached to a first therapeutic agent, and wherein one or more of the plurality of membrane destabilizing block copolymers is attached to a second therapeutic agent. In certain embodiments, one or more of the plurality of membrane destabilizing block copolymers is attached to a first therapeutic agent, and wherein one or more of the additional polymers is attached to a second therapeutic agent.

In some embodiments, the shell of the micellic assembly and/or shell block of one or more of the membrane destabilizing block copolymers comprises at least one nucleotide, at least one carbohydrate, or at least one amino acid. In certain embodiments, the shell of the micellic assembly and/or shell block of one or more of the membrane destabilizing block copolymers comprises polynucleotide, an oligonucleotide, a gene expression modulator, a knockdown agent, an siRNA, an RNAi agent, a dicer substrate, an miRNA, an shRNA, an antisense oligonucleotide, an aptamer, a proteinaceous therapeutic agent, a protein, a peptide, an enzyme, a hormone, an antibody, an antibody fragment, a carbohydrate, a small molecule with a molecular weight of greater than about 500 Daltons, or a combination thereof.

In some embodiments, the micellic assemblies described herein comprise a polynucleotide, wherein the polynucleotide is a mammalian expression vector. In another embodiment, the micellic assemblies described herein comprise a polynucleotide that is designed to recombine with and correct an endogenous gene sequence in a human. In some embodiments, a polynucleotide provided in a micellic assembly described herein is a gene expression modulator.

A mammalian expression vector comprises a complimentary DNA sequence (a "cDNA" or mini-gene) that is functionally linked to a promoter region such that the promoter drives expression of the cDNA. In certain instances, mammalian expression vectors also comprise a polyadenylation signal at the 3' end of the cDNA. A promoter region is a nucleotide segment that is recognized by a RNA polymerase molecule, in order to initiate RNA synthesis (i.e., transcription), and may also include other transcriptional regulatory elements such as enhancers. Any number of transcriptional regulatory sequences may be used to mediate expression of linked genes in mammalian expression vectors. Promoters include but are not limited to retroviral promoters, other viral promoters such as those derived from HSV or CMV, and promoters from endogenous cellular genes. Mammalian expression vectors also typically have an origin of replication from *E. Coli* to enable propagation as plasmids in bacteria.

In certain instances, it is desirable to be able to introduce mammalian expression vectors into mammalian cells in culture or in vivo. In some embodiments, expression vectors are transfected into mammalian cells using the micellic assemblies provided herein.

As described herein, the micellic assemblies provided herein are used, in some embodiments, for delivery of polynucleotides into a cell or to an individual in need thereof. In certain embodiments, the micellic assembly's polycationic blocks (e.g., the shell blocks of the membrane destabilizing block copolymers described herein) bind to the mammalian expression vector DNA and complexes the DNA with the micellic assembly. In certain instances, polycations bind to and complex with mammalian expression vectors DNA. In some embodiments, a micellic assembly comprising a polynucleotide complex is charge neutralized (e.g., the shell of the micellic assembly or the shell block of a polymer of the micellic assembly and the polynucleotide are substantially charge neutralized). Depending on the length of the polynucleotide, the length of the polycationic block is optionally adjusted to provide charge neutralization for the polynucleotide. In some instances, charge-neutralization is achieved by addition of cations and/or polycations into the formulation. In some embodiments, a micellic assembly comprising a polymer and a polynucleotide (e.g., a 200+mer) is then diluted as necessary in an appropriate buffer and added directly to cells in culture. Expression of the transfected gene or cDNA in the resulting cells can be readily measured by including in the mammalian expression vector an expression cassette driving an indicator gene such as lucif erase, chloramphenicol acetyl transferase or GFP. These genes are readily available and reporter assays are described.

In some embodiments, micellic assemblies provided herein are used for gene therapy. The treatment of diseases and disorders by gene therapy generally involves the transfer of new genetic information into cells. "Gene therapy vectors" comprise the new genetic material to be delivered, which is, optionally, in a mammalian expression vector. The uses of micellic assemblies include delivery of DNA sequences for gene replacement, inhibition of gene expression, gene correction or gene augmentation, or the introduction of genes to have some other desired effect, such as the modulation of immune responses. Inhibition of gene expression is accomplished in any suitable manner, including, by way of non-limiting example, by expression of gene cassettes in cells which express shRNAs or other RNAi agents.

In some embodiments, micellic assemblies having a polycationic shell block are mixed with gene therapy vectors, such that they become bound to the micellic assembly. The micellic assembly-gene therapy vector complex, in a suitable excipient (see below) is then administered to a living subject by routes including but not limited to intravenous, intra-arcticular, intrathecal, intracranial, inhalation, sub-cutaneous or intra-ocular.

In specific embodiments, a micellic assembly provided herein comprises at least one polynucleotide (e.g., oligonucleotide). In some embodiments, the micellic assemblies provided herein are useful for delivering polynucleotides (e.g., oligonucleotides) to an individual in need thereof. In specific embodiments, the provided herein is a micellic assembly that comprises at least 2, at least 4, at least 5, at least 10, at least 20, at least 30, at least 40, at least 50, at least 100 polynucleotides. In some embodiments, the micellic assembly provided herein comprises 2-50 polynucleotides, 5-40 polynucleotides, 5-30 polynucleotides, 5-25 polynucleotides, 20-40 polynucleotides, or the like. In certain embodiments, the polynucleotide is an oligonucleotide gene expression modulator. In further embodiments, the polynucleotide is an oligonucleotide knockdown agent. In specific embodiments, the polynucleotide is an RNAi agent, dicer substrate, or siRNA. In certain embodiments, the micellic assembly is a nanoparticle (e.g., a micelle) comprising a core, a shell and one or more polynucleotide, wherein the polynucleotide is not in the core of the micellic assembly. In specific embodiments, the polynucleotide is incorporated into (e.g., is present in and/or forms a portion of) the shell of the micellic assembly. In some embodiments, one or more polynucleotide (e.g., oligonucleotide or siRNA) is attached to shell block of the a polymer (e.g., a membrane destabilizing block copolymer, or a non-membrane destabilizing diluent/carrier polymer) of the micellic assembly. In various embodiments, attachment is achieved through one or more covalent bond, one or more non-covalent interaction, or a combination thereof. In some embodiments, the siRNA is covalently attached to a hydrophobic block of the membrane destabilizing block copolymer (e.g., a core block). In specific embodiments, the siRNA is covalently attached to a hydrophobic block (e.g., a core block) of the block copolymer and forms at least a portion of the shell of the micellic assembly. In more specific embodiments, the siRNA is a hydrophilic block (e.g., a shell block) of the block copolymer. In other embodiments, the siRNA is attached to the hydrophilic block of a block copolymer, or to an optional polymer block (e.g., a spacer block).

In some embodiments, one or more therapeutic agent (e.g., oligonucleotide or siRNA) is attached to a block copolymer provided herein in any manner suitable, e.g., by non-covalent association. Non-covalent association between (i) a polymer and/or an assembly of polymers provided herein (e.g., a micelle formed by a plurality of polymers) and (ii) one or more therapeutic agent (e.g., oligonucleotide) is achieved in any suitable manner, including, but not limited to, electrostatic interaction (including electrostatic interaction with a polymer having cationic groups and a therapeutic agent having anionic groups), hydrophobic interaction, affinity interaction, or a combination thereof. In certain embodiments, the one or more therapeutic agent and/or the polymers of the micellic assembly (e.g., micelle) is modified with chemical moieties that afford one or more therapeutic agent and/or polymers that have an affinity for one another, such as arylboronic acid-salicylhydroxamic acid, leucine zipper or other peptide motifs, ionic interactions between positive and negative charges on the micelle and therapeutic agent, or other types of non-covalent chemical affinity linkages. Additionally, in some embodiments, a double-stranded polynucleotide is associated with (e.g., complexed to) a polymer or micellic assembly (e.g., micelle) described herein. In some embodiments, a polymer or micellic assembly (e.g., micelle) is associated (e.g., complexed) with a nucleic acid minor groove binding agent or an intercalating agent that is attached (e.g., covalently) to a component (e.g., a polymer) of the micellic assembly (e.g., micelle).

In some embodiments, the therapeutic agent (e.g., oligonucleotide) comprises at least one negative charge (e.g., comprises a negatively charged backbone) and is associated with a cationic shell of the micellic assembly (e.g., micelle) and/or a cationic shell block of a block copolymer of the micellic assembly. In specific embodiments, the cationic shell or shell block at least partially neutralizes the negative charges present in the one or more therapeutic agents (e.g., oligonucleotides) attached to or present in the micellic assembly. In certain embodiments, one or more therapeutic agent (e.g., one or more oligonucleotide, one or more siRNA, or a combination thereof) forms an association (e.g., a complex) with the polycationic shell blocks of the micellic assembly (e.g., micelle). In some embodiments, the association (e.g., complex) between the micellic assembly (e.g., micelle) and therapeutic agent (e.g., oligonucleotide or siRNA) forms at any desired charge ratio of block copolymer forming the micellic assembly (e.g., micelle) to therapeutic agent (e.g., oligonucleotide or siRNA), e.g., between 1:1 and 16:1. In specific embodiments, the complex between the micelle and siRNA forms at the charge ratio of 2:1, 4:1 or 8:1. In other words, in some embodiments, the ratio of the number of cationic charges present in the shell of the micellic assembly to the number of anionic charges present in the therapeutic agent is any desired value, e.g., about 1:1 to about 16:1, about 2:1 to about 8:1, about 4:1 to about 12:1, about 2:1, about 4:1, or about 8:1. In some embodiments, siRNA is charge-neutralized by a polycationic block of a block copolymer forming the micellic assembly. For example, in some specific embodiments, a 20-base pair polynucleotide (e.g., oligonucleotide or siRNA) comprising 40 negative charges at physiologic pH is associated (e.g., complexed) with a micellic assembly (e.g., micelle) comprising a polyDMAEMA shell block (80 monomeric units in length, MW=11,680) with a pKa of about 7.4. At this pH, polyDMAEMA contains 40 negative charges, thereby resulting in a polynucleotide-shell block association (e.g., complex) that is substantially net neutral in charge. In certain instances, avoiding a large number of excess positive charges helps to reduce in vitro and in vivo toxicity. In some embodiments, a therapeutic agent (e.g., oligonucleotide or siRNA) spontaneously associates with a positively charged shell of a micellic assembly (e.g., micelle) provided herein.

In some embodiments, a therapeutic agent (e.g., oligonucleotide or peptide) is chemically conjugated to the micellic assembly (e.g., micelle) and/or to one or more polymer of the micellic assembly (e.g., micelle) by any suitable chemical conjugation technique. Therapeutic agents are optionally conjugated to an end of the polymer, or to a pendant side chain of the polymer. In some embodiments, micellic assemblies (e.g., micelles) containing an RNAi agent are formed by conjugation of the RNAi agent with an already formed micellic assembly (e.g., micelle) comprising a plurality of polymers (e.g., block copolymers). In other embodiments, micellic assemblies (e.g., micelles) containing an RNAi agent are formed by conjugation of the RNAi agent with a polymer (e.g., a membrane destabilizing block copolymer) and subsequently forming the micellic assembly (e.g., micelle) in any suitable manner, e.g., by self assembly of the resulting conjugates into a micellic assembly (e.g., micelle) comprising the RNAi agent. In various embodiments, such a micellic assembly optionally further comprises unconjugated polymers (e.g., block copolymers) that are similar, identical, or different than those conjugated to the RNAi agent. The covalent bond between a polymer and a therapeutic agent of a micellic assembly described herein is, optionally, non-cleavable, or cleavable. In certain embodiments, a precursor of one or more RNAi agent (e.g. a dicer substrate) is attached to the micellic assembly (e.g., micelle) or to the polymeric units of micellic assembly (e.g., the micelle by a non-cleavable bond). In some embodiments, one or more RNAi agent is attached through a cleavable bond. In certain embodiments, the cleavable bonds utilized in the micellic assemblies described herein include, by way of non-limiting example, disulfide bonds (e.g., disulfide bonds that dissociate in the reducing environment of the cytoplasm). In some embodiments, covalent association between a micellic assembly (including the components thereof) and a therapeutic agent (e.g., an oligonucleotide or siRNA or peptide) is achieved through any suitable chemical conjugation method, including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In some embodiments, conjugation is also performed with pH-sensitive bonds and linkers, including, but not limited to, hydrazone and acetal linkages. Any other suitable conjugation method is optionally utilized as well, for example a large variety of conjugation chemistries are available (see, for example, *Bioconjugation*, Aslam and Dent, Eds, Macmillan, 1998 and chapters therein).

In specific embodiments, the agent delivered by the means of the micellic assembly provided herein is a diagnostic agent. In some embodiments, the diagnostic agent is a diagnostic imaging agent, e.g., an agent useful in imaging the mammalian vascular system which includes but is not limited to position emission tomography (PET) agents, computerized tomography (CT) agents, magnetic resonance imaging (MRI) agents, nuclear magnetic imaging agents (NMI), fluoroscopy agents and ultrasound contrast agents. Such diagnostic agents include radioisotopes of such elements as iodine (I), including $^{123}$I, $^{125}$I, $^{131}$I, etc., barium (Ba), gadolinium (Gd), technetium (Tc), including $^{99}$Tc, phosphorus (P), including $^{31}$P, iron (Fe), manganese (Mn), thallium (Tl), chromium (Cr), including $^{51}$Cr, carbon (C), including $^{14}$C, or the like, fluorescently labeled compounds, or their complexes, chelates, adducts and conjugates. In other embodiments, the diagnostic agent is a marker gene that encode proteins that are readily detectable when expressed in a cell (including, but not limited to, β-galactosidase, green fluorescent protein, luciferase, and the like) and labeled nucleic acid probes (e.g., radiolabeled or fluorescently labeled probes). In some embodiments, covalent conjugation of diagnostics agents to the micellic assemblies provided herein is achieved according to a variety of conjugation processes. In other embodiments, the diagnostic agent is non-covalently associated with the micellic assembly provided herein by complexing with a chelating residue (e.g., a carboxylic acid residue) incorporated into the block copolymers forming the micellic assembly. In some embodiments, a radiolabeled monomer (e.g., a $^{14}$C-labeled monomer) is incorporated into the polymeric backbone of the micellic assembly (e.g., the shell block or the core block of the micelle). In some embodiments, a micellic assembly associated with a diagnostic agent comprises a targeting moiety.

In some embodiments, the therapeutic agent is a proteinaceous agent. Conjugation of proteinatious therapeutic agents (e.g., a polypeptide) to the micellic assemblies provided herein is achieved according to a variety of conjugation processes by a chemical reaction involving one or more of the functional groups of the proteinaceous therapeutic agent (e.g., a polypeptide) with one or more of the functional groups present in the micellic assembly (e.g., in the shell of the micellic assembly or on a monomeric unit of the shell block). Polypeptide functional groups that are usually involved include but are not limited to amino, hydroxy, thiol, or carboxyl groups. Such groups can be present as a terminal group or present on the amino acid side chains. In some embodiments, the proteinaceous therapeutic agents are engineered to contain non-natural amino acids comprising special functional groups for formation of site-specific conjugates, e.g., azido groups for conjugation via "click" chemistry.

In certain embodiments, a conjugate of one or more therapeutic agent (e.g., oligonucleotide) with a polymer (e.g., block copolymer), wherein the polymer is a unimer or present in an assembled micellic assembly, provided herein is prepared according to a process comprising the following two steps: (1) activating a modifiable end group (for example, 5'-or 3'-hydroxyl or) of an oligonucleotide using any suitable activation reagents, such as but not limited to 1-ethyl-3,3-dimethylaminopropyl carbodiimide (EDAC), imidazole, N-hydrosuccinimide (NHS) and dicyclohexyl-carbodiimide (DCC), HOBt (1-hydroxybenzotriazole), p-nitrophenylchloroformate, carbonyldiimidazole (CDI), and N,N'-disuccinimidyl carbonate (DSC); and (2) covalently linking a block copolymer to the end of the oligonucleotide. In some embodiments, the 5'-or 3'-end modifiable group of an oligonucleotide is substituted by other functional groups prior to conjugation with the block copolymer. For example, hydroxyl group (—OH) is optionally substituted with a linker carrying sulfhydryl group (—SH), carboxyl group (—COOH), or amine group (—NH$_2$).

In yet another embodiment, an oligonucleotide comprising a functional group introduced into one or more of the bases (for example, a 5-aminoalkylpyrimidine), is conjugated to a polymer (e.g., block copolymer), wherein the polymer is a unimer or present in a micellic assembly, provided herein using an activating agent or a reactive bifunctional linker according to any suitable procedure. A variety of such activating agents and bifunctional linkers is available commercially from such suppliers as Sigma, Pierce, Invitrogen and others.

In some embodiments, the micellic assembly (e.g., micelle) comprising an oligonucleotide or a plurality of oligonucleotides is formed by a spontaneous self assembly. Spontaneous self assembly of the micellic assembly is achieved, in some embodiments, in a single pot. For example, in some embodiments, a micellic assembly (e.g., a micelle) self-assembled by diluting a solution of a polymer (e.g., block copolymer) described herein in an organic solvent (e.g., ethanol) with an aqueous media (e.g., water or PBS) is combined with one or more therapeutic agent (e.g., oligonucleotide or siRNA), the micellic assembly comprising the polymers and one or more therapeutic agent spontaneously forming thereby. In other embodiments, spontaneous self assembly occurs by (1) contacting one or more therapeutic agent (e.g., oligonucleotide or siRNA) of interest with a polymer (e.g., membrane destabilizing block copolymer, a non-membrane destabilizing block copolymer, or a monoblock polymer) described herein so as to form a polymer-therapeutic agent conjugate; and (2) subjecting the polymer-therapeutic agent conjugates to conditions suitable to afford self assembly of the polymer-therapeutic agent conjugates into a micellic assembly described herein. In some embodiments, the step of affording self assembly of the polymer-therapeutic agent conjugates further comprises contacting the polymer-therapeutic agent conjugates with an additional polymer (e.g., a non-conjugated block copolymer or monoblock polymer, or a diluent polymer, or the like, or a combination thereof).

In some embodiments, any micellic assembly described herein further comprises an additional polymer that is not attached to a therapeutic agent. In some embodiments, the additional polymer is a diluent polymer or a targeting moiety carrier polymer. In certain embodiments, any micellic assembly provided herein further comprises an additional polymer that is attached to at least one second therapeutic agent (e.g., a second therapeutic agent). In certain embodiments, the at least one second therapeutic agent (e.g., second therapeutic agent) is different from the at least one therapeutic agent (e.g., a first therapeutic agent). In some embodiments, the core portion (e.g., core blocks) of all polymers present in the micellic assembly are similar or identical. In certain embodiments, one or more different polymer in the micellic assembly comprises similar or identical core portions (e.g., core blocks), but different non-core portions (e.g., shell blocks).

Therapy

In some embodiments, the micellic assemblies (e.g., micelles) provided herein are useful in treating a subject at risk for or afflicted with disorders associated with and/or caused by high plasma levels or cholesterol, apolipoprotein b, and/or LDL cholesterol, e.g. hypercholesterolemia. In certain embodiments, the treatment comprises providing a micellic assembly comprising a therapeutic agent (e.g., an oligonucleotide agent), wherein the therapeutic agent silences (e.g., by cleavage) a gene or a gene product which promotes such condition. In some embodiments the therapeutic agent (e.g., an oligonucleotide or RNAi agent) silences proprotein convertase subtilisin/kexin type 9 (PCSK9) gene responsible for regulation of low density lipoprotein (LDLR) levels and function, and thus micellic assemblies comprising such therapeutic agent are used to treat a subject having or at risk for a disorder characterized by unwanted PCSK9 expression, e.g., disorders associated with and/or caused by high plasma levels or cholesterol, apolipoprotein b, and/or LDL cholesterol, e.g. hypercholesterolemia. In some embodiments, the micellic assemblies deliver PCSK9-silencing polynucleotide agent (e.g, siRNA) to a cell expressing PCSK9. In some embodiments, the cell is a liver cell.

In some embodiments, the micellic assemblies (e.g., micelles) provided herein are useful in treating a subject at risk for or afflicted with unwanted cell proliferation (e.g., malignant or nonmalignant cell proliferation). The treatment comprises providing a micellic assembly comprising a therapeutic agent (e.g., an oligonucleotide agent), wherein the therapeutic agent can silence (e.g., by cleavage) a gene or a gene product which promotes unwanted cell proliferation; and administering a therapeutically effective dose of the micellic assembly to a subject (e.g., a human subject.) In some embodiments, the therapeutic agent is a polynucleotide (e.g., an oligonucleotide) which is homologous to and can silence (e.g., by cleavage) a gene.

In certain embodiments, the gene is but is not limited to a growth factor or growth factor receptor gene, a phosphatase, a kinase, e.g., a protein tyrosine, serine or threonine kinase gene, an adaptor protein gene, a gene encoding a G protein superfamily molecule, or a gene encoding a transcription factor. In some instances, the micellic assembly comprises a polynucleotide which silences a gene which is expressed in a specific tissue or organ, including, but not limited to lung, pancreas, liver, kidney, ovary, muscle, skin, breast, colon, stomach, and the like.

In some embodiments, the oligonucleotide agent silences one or more of the following genes: the PDGF beta gene, and thus can be used to treat a subject having or at risk for a disorder characterized by unwanted PDGF beta expression, e.g., testicular and lung cancers; an Erb-B gene (e.g., Erb-B-2 or Erb-B-3), and thus can be used to treat a subject having or at risk for a disorder characterized by unwanted Erb-B expression, e.g., breast or lung cancer; the Src gene, and thus can be used to treat a subject having or at risk for a disorder characterized by unwanted Src expression, e.g., colon cancers; the CRK gene, and thus can be used to treat a subject having or at risk for a disorder characterized by unwanted CRK expression, e.g., colon and lung cancers; the GRB2 gene, and thus can be used to treat a subject having or at risk for a disorder characterized by unwanted GRB2 expression, e.g., squamous cell carcinoma; the RAS gene, and thus can be used to treat a subject having or at risk for a disorder characterized by unwanted RAS expression, e.g., pancreatic, colon and lung cancers, and chronic leukemia; the MEKK gene, and thus can be used to treat a subject having or at risk for a disorder characterized by unwanted MEKK expression, e.g., squamous cell carcinoma, melanoma or leukemia; the JNK gene, and thus can be used to treat a subject having or at risk for a disorder characterized by unwanted JNK expression, e.g., pancreatic or breast cancers; the RAF gene, and thus can be used to treat a subject having or at risk for a disorder characterized by unwanted RAF expression, e.g., lung cancer or leukemia; the Erk1/2 gene, and thus can be used to treat a subject having or at risk for a disorder characterized by unwanted Erk1/2 expression, e.g., lung cancer; the PCNA(p21) gene, and thus can be used to treat a subject having or at risk for a disorder characterized by unwanted PCNA expression, e.g., lung cancer; the MYB gene, and thus can be used to treat a subject having or at risk for a disorder characterized by unwanted MYB expression, e.g., colon cancer or chronic myelogenous leukemia; the c-MYC gene, and thus can be used to treat a subject having or at risk for a disorder characterized by unwanted c-MYC expression, e.g., Burkitt's lymphoma or neuroblastoma; the JUN gene, and thus can be used to treat a subject having or at risk for a disorder characterized by unwanted JUN expression, e.g., ovarian, prostate or breast cancers; the FOS gene, and thus can be used to treat a subject having or at risk for a disorder characterized by unwanted FOS expression, e.g., skin or prostate cancers; the BCL-2 gene, and thus can be used to treat a subject having or at risk for a disorder characterized by unwanted BCL-2 expression, e.g., lung or prostate cancers or Non-Hodgkin lymphoma; the Cyclin D gene, and thus can be used to treat a subject having or at risk for a disorder characterized by unwanted Cyclin D expression, e.g., esophageal and colon cancers; the VEGF gene, and thus can be used to treat a subject having or at risk for a disorder characterized by unwanted VEGF expression, e.g., esophageal and colon cancers; the EGFR gene, and thus can be used to treat a subject having or at risk for a disorder characterized by unwanted EGFR expression, e.g., breast cancer; the Cyclin A gene, and thus can be used to treat a subject having or at risk for a disorder characterized by unwanted Cyclin A expression, e.g., lung and cervical cancers; the Cyclin E gene, and thus can be used to treat a subject having or at risk for a disorder characterized by unwanted Cyclin E expression, e.g., lung and breast cancers; the WNT-I gene, and thus can be used to treat a subject having or at risk for a disorder characterized by unwanted WNT-I expression, e.g., basal cell carcinoma; the beta-catenin gene, and thus can be used to treat a subject having or at risk for a disorder characterized by unwanted beta-catenin expression, e.g., adenocarcinoma or hepatocellular carcinoma; the c-MET gene, and thus can be used to treat a subject having or at risk for a disorder characterized by unwanted c-MET expression, e.g., hepatocellular carcinoma; the PKC gene, and thus can be used to treat a subject having or at risk for a disorder characterized by unwanted PKC expression, e.g., breast cancer; the NFKB gene, and thus can be used to treat a subject having or at risk for a disorder characterized by unwanted NFKB expression, e.g., breast cancer; the STAT3 gene, and thus can be used to treat a subject having or at risk for a disorder characterized by unwanted STAT3 expression, e.g., prostate cancer; the survivin gene, and thus can be used to treat a subject having or at risk for a disorder characterized by unwanted survivin expression, e.g., cervical or pancreatic cancers; the Her2/Neu gene, and thus can be used to treat a subject having or at risk for a disorder characterized by unwanted Her2/Neu expression, e.g., breast cancer; the topoisomerase I gene, and thus can be used to treat a subject having or at risk for a disorder characterized by unwanted topoisomerase I expression, e.g., ovarian and colon cancers; the topoisomerase II alpha gene, and thus can be used to treat a subject having or at risk for a disorder characterized by unwanted topoisomerase II expression, e.g., breast and colon cancers.

In other embodiments the oligonucleotide agent silences mutations in one of the following genes: the p73 gene, and thus can be used to treat a subject having or at risk for a disorder characterized by unwanted p73 expression, e.g., colorectal adenocarcinoma; the p21(WAF1/CIP1) gene, and thus can be used to treat a subject having or at risk for a disorder characterized by unwanted p21 (WAF1/CIP1) expression, e.g., liver cancer; the p27(KIP1) gene, and thus can be used to treat a subject having or at risk for a disorder characterized by unwanted p27(KIP1) expression, e.g., liver cancer; the PPM1D gene, and thus can be used to treat a subject having or at risk for a disorder characterized by unwanted PPM1D expression, e.g., breast cancer; the RAS gene, and thus can be used to treat a subject having or at risk for a disorder characterized by unwanted RAS expression, e.g., breast cancer; the caveolin I gene, and thus can be used to treat a subject having or at risk for a disorder characterized by unwanted caveolin I expression, e.g., esophageal squamous cell carcinoma; the MIB I gene, and thus can be used to treat a subject having or at risk for a disorder characterized by unwanted MIB I expression, e.g., male breast carcinoma (MBC); MTAI gene, and thus can be used to treat a subject having or at risk for a disorder characterized by unwanted MTAI expression, e.g., ovarian carcinoma; the M68 gene, and thus can be used to treat a subject having or at risk for a disorder characterized by unwanted M68 expression, e.g., human adenocarcinomas of the esophagus, stomach, colon, and rectum.

In some embodiments the oligonucleotide agent silences mutations in tumor suppressor genes, and thus can be used as a method to promote apoptotic activity in combination with chemotherapeutics. In some embodiments the in the tumor suppressor gene is selected from one or more of the following tumor suppressor genes: the p53 tumor suppressor gene, the p53 family member DN-p63, the pRb tumor suppressor gene, the APC1 tumor suppressor gene, the BRCA1 tumor suppressor gene, the PTEN tumor suppressor gene.

In some embodiments the oligonucleotide agent silences one of the following fusion genes: mLL fusion genes, e.g., mLL-AF9, and thus can be used to treat a subject having or at risk for a disorder characterized by unwanted mLL fusion gene expression, e.g., acute leukemias; the BCR/ABL fusion gene, and thus can be used to treat a subject having or at risk for a disorder characterized by unwanted BCR/ABL fusion gene expression, e.g., acute and chronic leukemias; the TEL/AML1 fusion gene, and thus can be used to treat a subject having or at risk for a disorder characterized by unwanted TEL/AML1 fusion gene expression, e.g., childhood acute leukemia; the EWS/FLI1 fusion gene, and thus can be used to treat a subject having or at risk for a disorder characterized by unwanted EWS/FLI1 fusion gene expression, e.g., Ewing Sarcoma; the TLS/FUS1 fusion gene, and thus can be used to treat a subject having or at risk for a disorder characterized by unwanted TLS/FUS1 fusion gene expression, e.g., Myxoid liposarcoma; the PAX3/FKHR fusion gene, and thus can be used to treat a subject having or at risk for a disorder characterized by unwanted PAX3/FKHR fusion gene expression, e.g., Myxoid liposarcoma; the AML1/ETO fusion gene, and thus can be used to treat a subject having or at risk for a disorder characterized by unwanted AML1/ETO fusion gene expression, e.g., acute leukemia.

In some aspects herein the micellic assemblies provide therapeutic agents for treating a subject, e.g., a human, at risk for or afflicted with a disease or disorder that may benefit by angiogenesis inhibition e.g., cancer or retinal degeneration. The treatment comprises providing a micellic assembly comprising an oligonucleotide agent, wherein said oligonucleotide agent is homologous to and/or can silence, e.g., by cleavage, a gene which mediates angiogenesis (e.g., VEGF-R1, VEGF-R2 or a gene encoding signaling proteins for these receptors' pathways); and administering a therapeutically effective dosage of said micellic assembly comprising the oligonucleotide agent to a subject, e.g., a human subject.

In some embodiments the oligonucleotide agent silences one of the following genes: the alpha v-integrin gene, and thus can be used to treat a subject having or at risk for a disorder characterized by unwanted alpha V integrin, e.g., brain tumors or tumors of epithelial origin; the Flt-1 receptor gene, and thus can be used to treat a subject having or at risk for a disorder characterized by unwanted Flt-1 receptors, e.g., cancer and rheumatoid arthritis; the tubulin gene, and thus can be used to treat a subject having or at risk for a disorder characterized by unwanted tubulin, e.g., cancer and retinal neovascularization.

In some aspects the micellic assemblies comprising oligonucleotide agents provided herein relate to a method of treating a subject infected with a virus or at risk for or afflicted with a disorder or disease associated with a viral infection. The method comprises providing a micellic assembly comprising an oligonucleotide agent, wherein said oligonucleotide agent is homologous to and/or can silence, e.g., by cleavage, a viral gene or a cellular gene which mediates viral function, e.g., entry or growth; and administering a therapeutically effective dose of said oligonucleotide agent to a subject, e.g., a human subject.

In some embodiments, the micellic assemblies comprising an oligonucleotide agent are useful in treatment of subjects infected with the Human Papilloma Virus (HPV) or at risk for or afflicted with a disorder mediated by HPV, e.g, cervical cancer.

In some embodiments, the micellic assembly comprises an oligonucleotide agent silencing expression of a HPV gene is reduced. In some embodiments, the HPV gene is selected from the group of E2, E6, or E7.

In another embodiment the expression of a human gene that is required for HPV replication is reduced.

In some embodiments, the micellic assembly comprises an oligonucleotide agent useful in treating patients infected by the Human Immunodeficiency Virus (HIV) or at risk for or afflicted with a disorder mediated by HIV, e.g., Acquired Immune Deficiency Syndrome (AIDS). In some embodiments, the expression of an HIV gene is reduced. In other embodiments, the HIV gene is CCR5, Gag, or Rev. In some embodiments the expression of a human gene that is required for HIV replication is reduced. In some embodiments, the gene is CD4 or Tsg101.

In some embodiments, the micellic assembly comprises an oligonucleotide agent useful for treating patients infected by the Hepatitis B Virus (HBV) or at risk for or afflicted with a disorder mediated by HBV, e.g., cirrhosis and heptocellular carcinoma. In one embodiment, the expression of a HBV gene is reduced. In other embodiment, the targeted HBV gene encodes one of the groups of the tail region of the HBV core protein, the pre-cregious (pre-c) region, or the cregious (c) region. In other embodiments a targeted HBV-RNA sequence is comprised of the poly(A) tail. In some embodiments the expression of a human gene that is required for HBV replication is reduced.

In some embodiments, the micellic assembly comprises an oligonucleotide agent useful for treating patients infected with, or at risk for or afflicted with a disorder mediated by a virus selected from the following viruses: the Hepatitis A Virus (HAV); Hepatitis C Virus (HCV); any of the group of Hepatitis Viral strains comprising hepatitis D, E, F, G, or H; the Respiratory Syncytial Virus (RSV); the herpes Cytomegalovirus (CMV); the herpes Epstein Barr Virus (EBV); Kaposi's Sarcoma-associated Herpes Virus (KSHV); the JC Virus (JCV); myxovirus (e.g., virus causing influenza), rhinovirus (e.g., virus causing the common cold), or coronavirus (e.g., virus causing the common cold); the St. Louis Encephalitis flavivirus; the Tick-borne encephalitis flavivirus; the Murray Valley encephalitis flavivirus; the dengue flavivirus; the Simian Virus 40 (SV40); the encephalomyocarditis virus (EMCV); the measles virus (MV); the Varicella zoster virus (VZV); an adenovirus (e.g. virus causing a respiratory tract infection); the poliovirus; or a poxvirus (a poxvirus causing smallpox). In some embodiments the expression of a human gene that is required for the replication of these viruses is reduced.

In some embodiments, the micellic assembly comprises an oligonucleotide agent useful for treating patients infected by the Herpes Simplex Virus (HSV) or at risk for or afflicted with a disorder mediated by HSV, e.g, genital herpes and cold sores as well as life-threatening or sight-impairing disease, e.g., mainly in immunocompromised patients. In some embodiments, the expression of a HSV gene is reduced. In other embodiment, the targeted HSV gene encodes DNA polymerase or the helicase-primase. In some embodiments the expression of a human gene that is required for HSV replication is reduced.

In some embodiments, the micellic assembly comprises an oligonucleotide agent useful for treating patients infected by the West Nile Virusor at risk for or afflicted with a disorder mediated by West Nile Virus. In some embodiments, the expression of a West Nile Virus gene is reduced. In other preferred embodiments, the West Nile Virus gene is selected from the group comprising E, NS3, or NS5. In some embodiments the expression of a human gene that is required for West Nile Virus replication is reduced.

In some embodiments, the micellic assembly comprises an oligonucleotide agent useful for treating patients infected by the Human T Cell Lymphotropic Virus (HTLV), or a disease or disorder associated with this virus, e.g., leukemia or myelopathy. In some embodiments, the expression of a HTLV gene is reduced. In some embodiments, the HTLV1 gene is the Tax transcriptional activator. In some embodiments, the expression of a human gene that is required for HTLV replication is reduced.

In some aspects, the micellic assembly comprises an oligonucleotide agent useful for treating a subject infected with a pathogen, e.g., a bacterial, amoebic, parasitic, or fungal pathogen. The method of treatment comprises providing a micellic assembly comprising an oligonucleotide agent, wherein said oligonucleotide is homologous to and/or can silence, e.g., by cleavage of a pathogen gene or a gene involved in the pathogen's growth; and administering a therapeutically effective dose of said oligonucleotide agent to a subject, e.g., a human subject. The target gene can be selected from a gene involved in the pathogen's growth, cell wall synthesis, protein synthesis, transcription, energy metabolism, e.g., the Krebs cycle, or toxin production.

Thus, in some embodiments, the micellic assembly comprises an oligonucleotide agent useful for of treating patients infected by a *Plasmodium* that causes malaria. In some embodiments, the expression of a *Plasmodium* gene is reduced. In other embodiments, the gene is apical membrane antigen 1 (AMA1). In some embodiments, the expression of a human gene that is required for *Plasmodium* replication is reduced.

In some embodiments, the micellic assembly comprises an oligonucleotide agent useful for treating patients infected by *Mycobacterium ulcerans, Mycobacterium tuberculosis, Mycobacterium leprae, Staphylococcus aureus, Streptococcus pneumoniae, Streptococcus pyogenes, Chlamydia pneumoniae, Mycoplasma pneumoniae*, or a disease or disorder associated with any of these pathogens. In some embodiments, the expression of a bacterial gene and/or a human gene that is required for the replication of these bacteria is reduced.

In some embodiments, the diseases treated by the micellic assemblies provided herein may be systemic or present in a specific tissue, e.g., the lung, skin, liver, breast, kidney, pancreas, CNS, or the like. In certain aspects, the oligonucleotide silences a gene which mediates or is involved in a metabolic disease or disorder, e.g., diabetes, obesity, and the like. In certain embodiments, the oligonucleotide silences a gene which mediates or is involved in a pulmonary disease or disorder, e.g., chronic obstructive pulmonary disease (COPD), cystic fibrosis, or lung cancer. In some aspects herein, the micellic assemblies comprise an oligonucleotide agent useful for and/or related to a method of treating a subject, e.g., a human, at risk for or afflicted with a disease or disorder characterized by an unwanted immune response, e.g., an inflammatory disease or disorder or an autoimmune disease or disorder. The method comprises providing a micellic assembly comprising an oligonucleotide agent, wherein said oligonucleotide agent is homologous to and/or can silence, e.g., by cleavage, a gene which mediates an unwanted immune response; and administering said oligonucleotide agent to a subject, e.g., a human subject. In some embodiments, the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplanted organ or tissue, e.g., transplanted cardiac or vascular tissue; or thrombolysis. In other embodiments, the disease or disorder is restenosis, e.g., restenosis associated with surgical intervention e.g., angioplasty, e.g., percutaneous transluminal coronary angioplasty. In other embodiments, the disease or disorder is Inflammatory Bowel Disease, e.g., Crohn Disease or Ulcerative Colitis. In some embodiments, the disease or disorder is inflammation associated with an infection or injury. In other embodiments, the disease or disorder is asthma, allergy, lupus, multiple sclerosis, diabetes, e.g., type 11 diabetes, arthritis, e.g., rheumatoid or psoriatic. In certain embodiments the oligonucleotide agent silences an integrin or co-ligand thereof, e.g., VLA4, VCAM, ICAM. In other embodiments the oligonucleotide agent silences a selectin or co-ligand thereof, e.g., P-selectin, E-selectin (ELAM), I-selectin, P-selectin glycoprotein-1 (PSGL-I). In certain embodiments the oligonucleotide agent silences a component of the complement system, e.g., C3, C5, C3aR, C5aR, C3 convertase, and C5 convertase. In some embodiments the oligonucleotide agent silences a chemokine or receptor thereof, e.g., TNFI, TNFJ, IL-IJ, IL-2, IL-2R, IL-4, IL-4R, IL-5, IL-6, IL-8, TNFRI, TNFRII, IgE, SCYA11, and CCR3. In other embodiments the oligonucleotide agent silences GCSF, Gro1, Gro2, Gro3, PF4, MIG, Pro-Platelet Basic Protein (PPBP), MIP-II, MIP-IJ, RANTES, MCP-1, MCP-2, MCP-3, CMBKR1, CMBKR2, CMBKR3, CMBKR5, AIF-1, or I-309.

In some aspects, the micellic assemblies comprise an oligonucleotide agent useful for treating a subject, e.g., a human, at risk for or afflicted with a neurological disease or disorder. The method comprises providing a micellic assembly comprising an oligonucleotide agent, wherein said oligonucleotide is homologous to and/or can silence, e.g., by cleavage, a gene which mediates a neurological disease or disorder; and administering a therapeutically effective dose of said oligonucleotide agent to a subject, e.g., a human. In some embodiments the disease or disorder is Alzheimer Disease or Parkinson Disease. In certain embodiments the oligonucleotide agent silences an amyloid-family gene, e.g., APP; a presenilin gene, e.g., PSEN1 and PSEN2, or I-synuclein. In other embodiments the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCA8. In some embodiments the oligonucleotide agent silences HD, DRPLA, SCA1, SCA2, MJD1, CACNL1A4, SCA7, or SCA8.

In certain aspects, the micellic assemblies provided herein comprise an oligonucleotide agent capable of cleaving or silencing more than one gene. In these embodiments the oligonucleotide agent is selected so that it has sufficient homology to a sequence found in more than one gene, e.g. a sequence conserved between these genes. Thus in some embodiments an oligonucleotide agent targeted to such sequences effectively silences the entire collection of genes.

In some aspects, the micellic assemblies provided herein comprise two or more types of oligonucleotide agents wherein the oligonucleotide agents silence different genes of the same disease or different diseases.

Any agent described herein is attached to the micellic assembly or polymers (e.g., membrane destabilizing block copolymers or additional polymers) in any suitable manner, e.g., any manner described herein.

Targeting Moieties

In certain embodiments, micellic assemblies described herein comprise at least one targeting moiety (e.g., a moiety that targets a specific cell or type of cell). In some embodiments, the targeting moiety is in the core of the micellic assembly, in the shell of the micellic assembly, on the surface of the micellic assembly, attached to a core block of a membrane destabilizing block copolymer, attached to a shell block of a membrane destabilizing block copolymer, is a shell block of a membrane destabilizing agent, is present on a non-membrane destabilizing polymer within the micellic assembly, is attached to a therapeutic agent within the micellic assembly, or the like.

In specific instances, the micellic assemblies provided herein are useful for delivery of therapeutic agents to specifically targeted cells of an individual. In certain instances, the efficiency of the cell uptake of the micellic assemblies is enhanced by incorporation of targeting moieties into or on the surface of the micellic assemblies. A "targeting moiety" (used interchangeably with "targeting agent") is any affinity reagent which recognizes the surface of a cell (e.g., a select cell). In some embodiments, targeting moieties recognize a cell surface antigen or bind to a receptor on the surface of the target cell. Suitable targeting moieties include, by way of non-limiting example, antibodies, antibody-like molecules, or peptides, such as an integrin-binding peptides such as RGD-containing peptides, or small molecules, such as vitamins, e.g., folate, sugars such as lactose and galactose, or other small molecules. Cell surface antigens include a cell surface molecule such as a protein, sugar, lipid or other antigen on the cell surface. In specific embodiments, the cell surface antigen undergoes internalization. Examples of cell surface antigens targeted by the targeting moieties of the micellic assemblies (e.g., micelles) provided herein include, but are not limited to, the transferrin receptor type 1 and 2, the EGF receptor, HER2/Ncu, VEGF receptors, integrins, NGF, CD2, CD3, CD4, CD8, CD19, CD20, CD22, CD33, CD43, CD38, CD56, CD69, and the asialoglycoprotein receptor.

Targeting moieties are attached, in various embodiments, to either end of a polymer (e.g., block copolymer) of the micellic assembly, or to a side chain of a monomeric unit, or incorporated into a polymer block. Attachment of the targeting moiety to the polymer is achieved in any suitable manner, e.g., by any one of a number of conjugation chemistry approaches including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In specific embodiments, "click" chemistry is used to attach the targeting ligand to the block copolymers forming the micellic assemblies provided herein (for example of "click" reactions, see Wu, P.; Fokin, V. V.

Catalytic Azide-Alkyne Cycloaddition: Reactivity and Applications. *Aldrichim. Acta* 2007, 40, 7-17). A large variety of conjugation chemistries are optionally utilized (see, for example, *Bioconjugation*, Aslam and Dent, Eds, Macmillan, 1998 and chapters therein). In some embodiments, targeting ligands are attached to a monomer and the resulting compound is then used in the polymerization synthesis of a polymer (e.g., block copolymer) utilized in a micellic assembly described herein. In some embodiments, targeting moieties are attached to a block of a first block copolymer, or to a block of a second block copolymer in a mixed micellic assembly. In some embodiments, the targeting ligand is attached to the sense or antisense strand of siRNA bound to a polymer of the micellic assembly. In certain embodiments, the targeting agent is attached to a 5' or a 3' end of the sense or the antisense strand.

In specific embodiments, the block copolymers forming the micellic assemblies provided herein are biocompatible. As used herein, "biocompatible" refers to a property of a polymer characterized by it, or its in vivo degradation products, being not, or at least minimally and/or reparably, injurious to living tissue; and/or not, or at least minimally and controllably, causing an immunological reaction in living tissue. With regard to salts, it is presently preferred that both the cationic and the anionic species be biocompatible. As used herein, "physiologically acceptable" is interchangeable with biocompatible. In some instances, the micellic assemblies and polymers used therein (e.g., block copolymers) exhibit low toxicity compared to cationic lipids.

In some instances, one or more of the polymers (e.g., block copolymers) utilized in the micellic assemblies described herein comprise polyethyleneglycol (PEG) chains or blocks with molecular weights of approximately from 1,000 to approximately 30,000. In some embodiments, PEG is conjugated to polymer ends groups, or to one or more pendant modifiable group present in a polymer of a micellic assemblies provided herein. In some embodiments, PEG residues are conjugated to modifiable groups within the hydrophilic segment or block (e.g., a shell block) of a polymer (e.g., block copolymer) of a micellic assembly provided herein. In certain embodiments, a monomer comprising a PEG residue of 2-20 ethylene oxide units is co-polymerized to form the hydrophilic portion of the polymer forming the micellic assembly provided herein.

Cell Uptake

In some embodiments, the micellic assemblies comprising therapeutic agents (e.g., oligonucleotides or siRNA) are delivered to cells by endocytosis. Intracellular vesicles and endosomes are used interchangeably throughout this specification. Successful therapeutic agent (e.g., oligonucleotide or siRNA) delivery into the cytoplasm generally has a mechanism for endosomal escape. In certain instances, the micellic assemblies comprising therapeutic agents (e.g., oligonucleotide or siRNA) provided herein are sensitive to the lower pH in the endosomal compartment upon endocytosis. In certain instances, endocytosis triggers protonation or charge neutralization of anionically chargeable species (e.g., propyl acrylic acid units) of the micellic assemblies, resulting in a conformational transition in the micellic assemblies. In certain instances, this conformational transition results in a more hydrophobic membrane destabilizing form which mediates release of the therapeutic agent (e.g., oligonucleotide or siRNA) from the endosomes to the cytoplasm. In those micellic assemblies comprising siRNA, delivery of siRNA into the cytoplasm allows its mRNA knockdown effect to occur. In those micellic assemblies comprising other types of oligonucleotides, delivery into the cytoplasm allows their desired action to occur.

Pharmaceutical Compositions

Micellic assemblies provided herein (e.g., those attached to one or more therapeutic agent, such as one or more oligonucleotide) are optionally provided in a composition (e.g., pharmaceutically acceptable composition). In some embodiments, the micellic assemblies provided herein can be administered to a patient in any suitable manner, e.g., with or without stabilizers, buffers, and the like, to form a pharmaceutical composition. In some embodiments, the micellic assemblies provided herein are formulated and used as tablets, capsules or elixirs for oral administration, suppositories for rectal administration, sterile solutions, suspensions for injectable administration, and any other suitable compositions.

Provided are pharmaceutically acceptable formulations of the micellic assemblies comprising at least one therapeutic agent described herein. These formulations include salts of the above compounds, e.g., acid addition salts, e.g., salts of hydrochloric, hydrobromic, acetic acid, and benzene sulfonic acid. A pharmacological composition or formulation refers to a composition or formulation in a form suitable for administration, e.g., systemic administration, into a cell or patient, including for example a human. Suitable forms, in part, depend upon the use or the route of entry, e.g., oral, transdermal, or by injection. Thus, in specific embodiments wherein the micellic assembly comprises and is delivering a polynucleotide, the formulation is in a form that does not prevent the micellic assembly and, more specifically, the polynucleotide (e.g., oligonucleotide or siRNA) from reaching a target cell with the polynucleotide intact and/or functional. For example, in certain embodiments, pharmacological compositions injected into the blood stream are soluble and/or dispersible. Moreover, pharmaceutical compositions described herein are, preferably, non-toxic. In some embodiments, wherein a micellic assembly described herein is administered for therapeutic benefit, a therapeutic effective amount of the micellic assembly comprising a therapeutic agent (e.g., a polynucleotide, such as an siRNA) is administered. In an exemplary embodiment, a therapeutically effective amount includes an amount sufficient micellic assembly to provide about 10 mg or less of siRNA per kg of individual.

In some embodiments, pharmaceutical compositions comprising a micellic assembly, which comprise a therapeutic agent (e.g., a polynucleotide, such as an siRNA), are administered systemically. As used herein, "systemic administration" means in vivo systemic absorption or accumulation of drugs in the blood stream followed by distribution throughout the entire body. Administration routes which lead to systemic absorption include, without limitation: intravenous, subcutaneous, intraperitoneal, inhalation, oral, intrapulmonary and intramuscular. In some embodiments, the micellic assembly compositions are administered topically.

In some embodiments, the compositions are prepared for storage or administration and include a pharmaceutically effective amount of the therapeutic agent comprising micellic assembly in a pharmaceutically acceptable carrier or diluent. Any acceptable carriers or diluents are optionally utilized herein. Specific carriers and diluents are and are described, e.g., in *Remington's Pharmaceutical Sciences*, Mack Publishing Co., A. R. Gennaro Ed., 1985. For example, preservatives, stabilizers, dyes and flavoring agents are optionally added. These include sodium benzoate, sorbic acid and esters of p-hydroxybenzoic acid. In addition, antioxidants and suspending agents are optionally used. As used herein, the term "pharmaceutically acceptable carrier" means a non-toxic, inert solid, semi-solid or liquid filler, diluent, encapsulating material or formulation auxiliary of any type. Some examples of materials optionally used as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. In some embodiments, the pharmaceutical compositions provided herein are administered to humans and/or to animals, orally, rectally, parenterally, intracisternally, intravaginally, intranasally, intraperitoneally, topically (as by powders, creams, ointments, or drops), subcutaneously, bucally, or as an oral or nasal spray.

In various embodiments, liquid dosage forms for oral administration include pharmaceutically acceptable emulsions, microemulsions, solutions, suspensions, syrups, and elixirs. In addition to the active ingredients (i.e., micelle-oligonucleotide complexes provided herein), the liquid dosage forms optionally further contain inert diluents or excipients, such as by way of non-limiting example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions optionally also include adjuvants such as wetting agents, emulsifying and suspending agents, sweetening, flavoring, and perfuming agents.

In some embodiments, injectable preparations, for example, sterile injectable aqueous or oleaginous suspensions are formulated according in any suitable manner, e.g., using dispersing agents, wetting agents and/or suspending agents. The sterile injectable preparation is, optionally, a sterile injectable solution, suspension, or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil is optionally employed including synthetic mono—or diglycerides. In additional embodiments, fatty acids such as oleic acid are used in the preparation of injectables. In a specific embodiment, the micellic assembly particles are suspended in a carrier fluid comprising 1% (w/v) sodium carboxymethyl cellulose and 0.1% (v/v) Tween 80.

In some embodiments, the injectable formulations are sterilized, for example, by filtration through a bacteria-retaining filter, or by incorporating sterilizing agents in the form of sterile solid compositions which are optionally dissolved or dispersed in sterile water or other sterile injectable medium prior to use.

In certain embodiments, compositions for rectal or vaginal administration are suppositories. Suppositories are optionally prepared by mixing the therapeutic agent comprising micellic assemblies provided herein with suitable non-irritating excipients or carriers such as cocoa butter, polyethylene glycol, or a suppository wax which are solid at ambient temperature but liquid at body temperature and therefore melt in the rectum or vaginal cavity and release the therapeutic agent comprising micellic assemblies provided herein. As used herein, a "therapeutic agent comprising micellic assemblies provided herein" is used interchangeable with one or more micellic assembly provided herein comprising a one or more therapeutic agent.

Suitable solid dosage forms for oral administration include, by way of non-limiting example, capsules, tablets, pills, powders, and granules. In such solid dosage forms, the micellic assemblies comprising a therapeutic agent (e.g., oligonucleotide) are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type are also optionally employed as fillers in soft and hard-filled gelatin capsules using such excipients as lactose or milk sugar as well as high molecular weight polyethylene glycols and the like.

In some embodiments, the solid dosage forms of tablets, dragees, capsules, pills, and granules are prepared with coatings and shells such as enteric coatings and other suitable coatings. They optionally contain opacifying agents. In certain embodiments, they are of a composition that they release the active ingredient(s) only, or preferentially, in a certain part of the intestinal tract, optionally, in a delayed manner. Examples of suitable embedding compositions include, by way of non-limiting example, polymeric substances and waxes.

Solid compositions of a similar type are optionally employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include, by way of non-limiting example, ointments, pastes, creams, lotions, gels, powders, solutions, sprays, inhalants, or patches. In some embodiments, therapeutic agent comprising micellic assemblies provided herein are admixed under sterile conditions with a pharmaceutically acceptable carrier and, optionally, one or more preservative, one or more buffer, or a combination thereof (e.g., as may be required). Ophthalmic formulation, ear drops, and eye drops are also contemplated as being within the scope of this invention.

Ointments, pastes, creams, and gels provided herein optionally contain, in addition to the therapeutic agent comprising micellic assemblies provided herein, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays optionally contain, in addition to therapeutic agent comprising micellic assemblies provided herein, excipients such as lactose, talc, silicic acid, aluminum hydroxide, calcium silicates, and polyamide powder, or mixtures of these substances. In some embodiments, sprays additionally contain customary propellants such as chlorofluorohydrocarbons.

Transdermal patches have the added advantage of providing controlled delivery of a compound to the body. Such dosage forms are made in any suitable manner, e.g., by dissolving or dispensing the microparticles or nanoparticles in a proper medium. Absorption enhancers are optionally used to increase the flux of the compound across the skin. The rate can be controlled by either providing a rate controlling membrane or by dispersing therapeutic agent comprising micellic assemblies provided herein in a polymer matrix or gel.

In some aspects of the invention, the micellic assembly(s) provide some properties (e.g. mechanical, thermal, etc.) that are usually performed by excipients, thus decreasing the amount of such excipients required for the formulation.

In some embodiments, micellic assemblies provided herein have superior commercial viability relative to other technologies for delivering therapeutic agents, including but not limited to: decreased immunogenicity of the carrier following repeat in vivo administration; fewer steps needed to assemble the multiple elements of the delivery vehicle, resulting in lower cost of goods; and reproducibility of manufacture, as judged by the ability to manufacture repeated batches of product with less than 5%, less than 10%, or less than 20% batch-to-batch variability in biophysical assay properties (including but not limited to such as HPLC. GPC, DLS, and TEM).

EXAMPLES

Throughout the description of the present invention, various known acronyms and abbreviations are used to describe monomers or monomeric residues derived from polymerization of such monomers. Without limitation, unless otherwise noted: "BMA" (or the letter "B" as equivalent shorthand notation) represents butyl methacrylate or monomeric residue derived therefrom; "DMAEMA" (or the letter "D" as equivalent shorthand notation) represents N,N-dimethylaminoethyl methacrylate or monomeric residue derived therefrom; "Gal" refers to galactose or a galactose residue, optionally including hydroxyl-protecting moieties (e.g., acetyl) or to a pegylated derivative thereof (as described below); HPMA represents 2-hydroxypropyl methacrylate or monomeric residue derived therefrom; "MAA" represents methylacrylic acid or monomeric residue derived therefrom; "MAA(NHS)" represents N-hydroxyl-succinimide ester of methacrylic acid or monomeric residue derived therefrom; "PAA" (or the letter "P" as equivalent shorthand notation) represents 2-propylacrylic acid or monomeric residue derived therefrom, "PEGMA" refers to the pegylated methacrylic monomer, $CH_3O(CH_2O)_{7-8}OC(O)C(CH_3)CH_2$ or monomeric residue derived therefrom. In each case, any such designation indicates the monomer (including all salts, or ionic analogs thereof), or a monomeric residue derived from polymerization of the monomer (including all salts or ionic analogs thereof), and the specific indicated form is evident by context to a person of skill in the art.

Example 1: Preparation of Copolymers

Di-block polymers and copolymers of the following general formula are prepared:

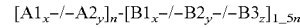

Where [A1-A2] is the first block copolymer, composed of residues of monomers A1 and A2

[B1-B2-B3] is the second block copolymer, composed of residues of monomers B1, B2, B3 x, y, z is the polymer composition in mole % monomer residue n is molecular weight Exemplary di-block copolymers:

[DMAEMA]-[B-/-P-/-D]

[PEGMA]-[B-/-P-/-D]

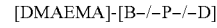

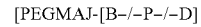

[DMAEMA-/-MAA(NHS)]-[B-/-P-/-D]

Where:
 B is butyl methacrylate
 P is propyl acrylic acid
 D is DMAEMA is dimethylaminoethyl methacrylate
 PEGMA is polyethyleneglycol methacrylate where, for example, w=4-5 or 7-8 ethylene oxide units)
 MAA(NHS) is methylacrylic acid-N-hydroxy succinamide
 HPMA is N-(2-hydroxypropyl) methacrylamide
 PDSM is pyridyl disulfide methacrylate These polymers represent structures where the composition of the first block of the polymer or copolymer is varied or chemically treated in order to create polymers where the first block is neutral (e.g., PEGMA), cationic (DMAEMA), anionic (PEGMA-NHS, where the NHS is hydrolyzed to the acid), ampholytic (DMAEMA-NHS, where the NHS is hydrolyzed to the acid), or zwitterrionic (for example, poly [2-methacryloyloxy-2'trimethylammoniumethyl phosphate]). In addition, the [PEGMA-PDSM]-[B-P-D] polymer contains a pyridyl disulfide functionality in the first block that can be reacted with a thiolated siRNA to form a polymer-siRNA conjugate.

Example 1.1: Synthesis of Block Copolymer Using RAFT Polymerization

A. RAFT chain transfer agent.
The synthesis of the chain transfer agent (CTA), 4-Cyano-4-(ethylsulfanylthiocarbonyl) sulfanylpentanoic acid (ECT), utilized for the following RAFT polymerizations, was adapted from a procedure by Moad et al., *Polymer*, 2005, 46(19): 8458-68. Briefly, ethane thiol (4.72 g, 76 mmol) was added over 10 minutes to a stirred suspension of sodium hydride (60% in oil) (3.15 g, 79 mmol) in diethyl ether (150 ml) at 0° C. The solution was then allowed to stir for 10 minutes prior to the addition of carbon disulfide (6.0 g, 79 mmol). Crude sodium S-ethyl trithiocarbonate (7.85 g, 0.049 mol) was collected by filtration, suspended in diethyl ether (100 mL), and reacted with Iodine (6.3 g, 0.025 mol). After 1 hour the solution was filtered, washed with aqueous sodium thiosulfate, and dried over sodium sulfate. The crude bis (ethylsulfanylthiocarbonyl) disulfide was then isolated by rotary evaporation. A solution of bis-(ethylsulfanylthiocarbonyl) disulfide (1.37 g, 0.005 mol) and 4,4'-azobis(4-cyanopentanoic acid) (2.10 g, 0.0075 mol) in ethyl acetate (50 mL) was heated at reflux for 18 h. Following rotary evaporation of the solvent, the crude 4-Cyano-4 (ethylsulfanylthiocarbonyl) sulfanylvpentanoic acid (ECT) was isolated by column chromatography using silica gel as the stationary phase and 50:50 ethyl acetate hexane as the eluent.

B. Poly(N,N-dimethylaminoethyl methacrylate) macro chain transfer agent (polyDMAEMA macroCTA).

The RAFT polymerization of DMAEMA was conducted in DMF at 30° C. under a nitrogen atmosphere for 18 hours using ECT and 2,2'-Azobis(4-methoxy-2.4-dimethyl valeronitrile) (V-70) (Wako chemicals) as the radical initiator. The initial monomer to CTA ratio ($[CTA]_0/[M]_0$ was such that the theoretical $M_n$ at 100% conversion was 10,000 (g/mol). The initial CTA to initiator ratio ($[CTA]_0/[I]_0$) was 10 to 1. The resultant polyDMAEMA macro chain transfer agent was isolated by precipitation into 50:50 v:v diethyl ether/pentane. The resultant polymer was redissolved in acetone and subsequently precipitated into pentane (x3) and dried overnight in vacuo.

C. Block copolymerization of DMAEMA, PAA, and BMA from a poly(DMAMEA) macroCTA.

The desired stoichiometric quantities of DMAEMA, PAA, and BMA were added to poly(DMAEMA) macroCTA dissolved in N,N-dimethylformamide (25 wt % monomer and macroCTA to solvent). For all polymerizations $[M]_0/[CTA]_0$ and $[CTA]_0/[I]_0$ were 250:1 and 10:1 respectively. Following the addition of V70 the solutions were purged with nitrogen for 30 min and allowed to react at 30° C. for 18 h. The resultant diblock copolymers were isolated by precipitation into 50:50 v:v diethyl ether/pentane. The precipitated polymers were then redissolved in acetone and subsequently precipitated into pentane (x3) and dried overnight in vacuo. Gel permeation chromatography (GPC) was used to determine molecular weights and polydispersities (PDI, $M_w/M_n$) of both the poly(DMAEMA) macroCTA and diblock copolymer samples in DMF with respect to polymethyl methacrylate standards (SEC Tosoh TSK-GEL R-3000 and R-4000 columns (Tosoh Bioscience, Montgomeryville, Pa.) connected in series to a Viscotek GPCmax VE2001 and refractometer VE3580 (Viscotek, Houston, Tex.). HPLC-grade DMF containing 1.0 wt % LiBr was used as the mobile phase. Figure IA summarizes the molecular weights, compositions and block ratios of some of the P7 RAFT synthesized polymers.

Example 1.2. Preparation of Second Block (B 1-B2-B3) Copolymerization of DMAEMA, PAA, and BMA from a Poly(PEGMA) macroCTA The desired stoichiometric quantities of DMAEMA, PAA, and BMA were added to poly(PEGMA) macroCTA dissolved in N,N-dimethylformamide (25 wt % monomer and macroCTA to solvent). For all polymerizations $[M]_0/[CTA]_0$ and $[CTA]_0/[I]_0$ were 250:1 and 10:1 respectively. Following the addition of AIBN the solutions were purged with nitrogen for 30 min and allowed to react at 68° C. for 6-12 h. The resulting diblock copolymers were isolated by precipitation into 50:50 v:v diethyl ether/pentane. The precipitated polymers were then redissolved in acetone and subsequently precipitated into pentane (x3) and dried overnight in vacuo. Gel permeation chromatography (GPC) was used to determine molecular weights and polydispersities (PDI, $M_m/M_n$) of both the poly(PEGMA) macroCTA and diblock copolymer samples in DMF using a Viscotek GPC-max VE2001 and refractometer VE3580 (Viscotek, Houston, Tex.). HPLC-grade DMF containing 1.0 wt % LiBr was used as the mobile phase. NMR spectroscopy in $CDCl_3$ was used to confirm the polymer structure and calculate the composition of the $2^{nd}$ block.

Example 1.3. Preparation and Characterization of PEGMA-DMAEMA Co-Polymers

Polymer synthesis was carried out using a procedure similar to that described in Examples 1.1 and 1.2. The ratio of the PEGM and DMAEMA in the first block was varied by using different feed ratios of the individual monomers to create the co-polymers described in Figure IB.

Example 1.4. Preparation and Characterization of PEGMA-MAA(NHS) Co-Polymers

Polymer synthesis was performed as described in Examples 1.1 and 1.2, using monomer feed ratios to obtain the desired composition of the $1^{st}$ block copolymer. In some instances, [PEGMA$_w$-MAA(NHS)]-[B-P-D] polymer is prepared where the co-polymer ratio of monomers in the $1^{st}$ block is 70:30. FIG. 14 summarizes the synthesis of of [PEGMA-MAA(NHS)]-[B-P-D] polymers where the co-polymer ratio of monomers in the $1^{st}$ block is 70:30. FIGS. 15A, 15B and 15C summarize characterization of polymers synthesized by RAFT Co-polymerization of PEGMA and MAA-NHS where the co-polymer ratio of monomers in the $1^{st}$ block is 70:30. NHS containing polymers can be incubated in aqueous buffer (phosphate or bicarbonate) at pH between 7.4 and 8.5 for 1-4 hrs at room temperature or 37° C. to generate the hydrolyzed (acidic) form.

Example 1.5. Preparation and Characterization of DMAEMA-MAA(NHS) Co-Polymers

Polymer synthesis was performed as described in Examples 1.1 and 1.2, using monomer feed ratios to obtain the desired composition of the $1^{st}$ block copolymer. In certain instances, [DMAEMA-MAA(NHS)]-[B-P-D] polymer is prepared where the co-polymer ratio of monomers in the $1^{st}$ block is 70:30. NHS containing polymers can be incubated in aqueous buffer (phosphate or bicarbonate) at pH between 7.4 and 8.5 for 1-4 hrs at room temperature or 37° C. to generate the hydrolyzed (acidic) form.

Example 2. Preparation and Characterization of HPMA-PDS(RNA) Co-Polymer Conjugates for siRNA Drug Delivery A. Synthesis of pyridyl disulfide methacrylate monomer (PDSMA).

Aldrithiol-2TM (5 g, 22.59 mmol) was dissolved in 40 ml of methanol and 1.8 ml of AcOH. The solution was added as a solution of 2-aminoethanethiol.HCl (1.28 g, 11.30 mmol) in 20 ml methanol over 30 min. The reaction was stirred under $N_2$ for 48h at R.T. After evaporation of solvents, the residual oil was washed twice with 40 ml of diethyl ether.

The crude compound was dissolved in 10 ml of methanol and the product was precipitated twice with 50 ml of diethyl ether to get the desired compound 1 as slight yellow solid. Yield: 95%.

Pyridine dithioethylamine (6.7 g, 30.07 mmol) and triethylamine (4.23 ml, 30.37 mmol) were dissolved in DMF (25 ml) and pyridine (25 ml) and methacryloyl chloride (3.33 ml, 33.08 mmol) was added slowly via syringe at 0 C. The reaction mixture was stirred for 2 h at R.T. After reaction, the reaction was quenched by sat. $NaHCO_3$ (350 ml) and extracted by ethyl acetate (350 ml). The combined organic layer was further washed by 10% HCl (100 ml, 1 time) and pure water (100 ml, 2 times) and dried by $MaSO_4$. The pure product was purified by column chromatography (EA/Hex: 1/10 to 2/1) as yellow syrup. Rf=0.28 (EA/Hex=1/1). Yield: 55%.

B. HPMA-PDSMA co-polymer synthesis

The RAFT polymerization of N-(2-hydroxypropyl) methacrylamide (HPMA) and pyridyl disulfide methacrylate (typically at a 70:30 monomer ratio) is conducted in DMF (50 weight percent monomer: solvent) at 68° C. under a nitrogen atmosphere for 8 hours using 2,2'-azo-bis-isobutyrylnitrile (AIBN) as the free radical initiator. The molar ratio of CTA to AIBN is 10 to 1 and the monomer to CTA ratio is set so that a molecular weight of 25,000 g/mol would be achieved if at 100% conversion. The poly(HPMA-PDS) macro-CTA was isolated by repeated precipitation into diethyl ether from methanol.

The macro-CTA is dried under vacuum for 24 hours and then used for block copolymerization of dimethylaminoethyl methacrylate (DMAEMA), propylacrylic acid (PAA), and butyl methacrylate (BMA). Equimolar quantities of DMAEMA, PAA, and BMA ($[M]_0/[CTA]_0$=250) are added to the HPMA-PDS macroCTA dissolved in N,N-dimethylformamide (25 wt % monomer and macroCTA to solvent). The radical initiator AIBN is added with a CTA to initiator ratio of 10 to 1. The polymerization is allowed to proceed under a nitrogen atmosphere for 8 hours at 68° C. Afterwards, the resultant diblock polymer is isolated by precipitation 4 times into 50:50 diethyl ether/pentane, redissolving in ethanol between precipitations. The product is then washed 1 time with diethyl ether and dried overnight in vacuo.

C. siRNA conjugation to HPMA-PDSMA co-polymer

Thiolated siRNA was obtained commercially (Agilent, Boulder, Colo.) as a duplex RNA with a disulfide modified 5'-sense strand. The free thiol form for conjugation is prepared by dissolving the lyophilized compound in water and treated for 1 hour with the disulfide reducing agent TCEP immobilized within an agarose gel. The reduced RNA (400 µM) was then reacted for 24 hours with the pyridyl disulfide-functionalized polymer in phosphate buffer (pH 7) containing 5 mM ethylenediaminetetraacetic acid (EDTA).

The reaction of the pyridyl disulfide polymer with the RNA thiol creates 2-pyridinethione, which can be spectrophotometrically measured to characterize conjugation efficiency. To further validate disulfide exchange, the conjugates are run on an SDS-PAGE 16.5% tricine gel. In parallel, aliquots of the conjugation reactions are treated with immobilized TCEP prior to SDS-PAGE to verify release of the RNA from the polymer in a reducing environment. Conjugation reactions are conducted at polymer/RNA stoichiometries of 1, 2, and 5. UV spectrophotometric absorbance measurements at 343 nm for 2-pyridinethione release are used to measure conjugation efficiencies.

Example 3: Synthesis of Polymers with Cell Targeting Agents: Click Reaction of Azido-Terminated Polymer with Propargyl Folate A combination of controlled radical polymerization and azide-alkyne click chemistry is used to prepare block copolymer micelles conjugated with biological ligands (for example, folate) with potential for active targeting of specific tissues/cells containing the specific receptor of interest (for example, folate). Block copolymers are synthesized by reversible addition-fragmentation chain transfer (RAFT) polymerization as described in Example 1, except that an azido chain transfer agent (CTA) is used. The azido terminus of the polymer is then reacted with the alkyne derivative of the targeting agent (for example, folate) to produce the polymer containing the targeting agent.

Synthesis of the RAFT Agent

The RAFT chain transfer agent (CTA) 2-dodecylsulfanyl-thiocarbonylsulfanyl-2-methyl-propionic acid 3-azidopropyl ester (C12-CTAN3) is prepared as follows:

Synthesis of 3-Azidopropanol. 3-Chloro-1-propanol (5.0 g, 53 mmol, 1.0 equiv) and sodium azide (8.59 g, 132 mmol, 2.5 equiv) are reacted in DMF (26.5 mL) at 100° C. for 48 h. The reaction mixture is cooled to room temperature, poured into ethyl ether (200 mL), and extracted with a saturated aqueous NaCl solution (500 mL). The organic layer is separated, dried over MgSO4, and filtered. The supernatant is concentrated to obtain the product (5.1 g, 95% yield).

Synthesis of 2-dodecylsulfanylthiocarbonylsulfanyl-2-methylpropionic acid chloride (DMP-Cl). 2-dodecylsulfanylthiocarbonylsulfanyl-2-methyl-propionic acid (DMP, Noveon >95%) (1.0 g, 2.7 mmol, 1.0 equiv) is dissolved in methylene chloride (15 mL) in a 50 mL round-bottom flask, and the solution is cooled to approximately 0° C. Oxalyl chloride (0.417 g, 3.3 mmol, 1.2 equiv) is added slowly under a nitrogen atmosphere, and the solution is allowed to reach room temperature and stirred for a total of 3 h. The resulting solution is concentrated under reduced pressure to yield the acid chloride product (1.0 g, 99% yield). Melting point) 63° C.

Synthesis of 2-dodecylsulfanylthiocarbonylsulfanyl-2-methylpropionic acid 3-azidopropyl ester. 3-Azidopropanol (265 mg, 2.62 mmol, 1.0 equiv) is dissolved in methylene chloride (5 mL) in a 50 mL round-bottom flask, and the solution is cooled to approximately 0° C. A solution of triethylamine (0.73 mL) in methylene chloride (5 mL) is added dropwise over 10 min. A solution of DMP-Cl (1.0 g, 2.6 mmol) in methylene chloride (5 mL) is added dropwise, and the solution is allowed to reach room temperature while stirring for 3 h. The solution is concentrated under reduced pressure, diluted with ethyl ether (100 mL), and washed with saturated aqueous sodium bicarbonate solution (50 mL), water (50 mL), and saturated NaCl solution (50 mL), successively. The organic layer is separated, dried over MgSO4 (1.0 g), and filtered. The supernatant is concentrated under reduced pressure to yield the product (1.05 g, 90% yield) as a residual oil. Synthesis of propargyl folate.

Folic acid (1.0 g, 0.0022 mol) is dissolved in DMF (10 mL) and cooled in a water/ice bath. N-Hydroxysuccinimide (260 mg, 0.0025 mol) and EDC (440 mg, 0.0025 mol) are added, and the resulting mixture is stirred in an ice bath for 30 min to give a white precipitate. A solution of propargylamine (124 mg, 2.25 mmol) in DMF (5.0 mL) is added, and the resulting mixture is allowed to warm to room temperature and stirred for 24 h. The reaction mixture is poured into water (100 mL) and stirred for 30 min to form a precipitate. The orange-yellow precipitate is filtered, washed with acetone, and dried under vacuum for 6 h to yield 1.01 g of product (93% yield).

Click reaction of azido-terminated polymers with propargyl folate.

The azido-terminated polymer is reacted with propargyl folate by the following example procedure. A solution of N3-α-$[D_s-X_t]_b$-$[B_x-P_y-D_z]_a$-ω (0.0800 mmol) in DMF (7 mL), and pentamethyldiethylenetriamine (PMDETA, Aldrich, 99%), (8.7 mg, 0.050 mmol) is purged with nitrogen for 60 min and transferred via syringe to a vial equipped with a magnetic stir bar containing CuBr (7.2 mg, 0.050 mmol) and propargyl folate (42 mg, 0.088 mmol) under a nitrogen atmosphere. The reaction mixture is stirred at 26° C. for 22 h in the absence of oxygen. The reaction mixture is exposed to air, and the solution is passed through a column of neutral alumina. DMF is removed under vacuum, and the product is precipitated into hexanes. The resulting folate-terminated block copolymer folate-α-$[D_s-X_t]_b$-$[B_x-P_y-D_z]_a$-ω is dissolved in THF and filtered to remove excess propargyl folate. THF is removed, and then the polymer is dissolved in deionized (DI) water and dialyzed for 6 h using a membrane with a molecular weight cutoff of 1000 Da. The polymer is isolated by lyophilization.

Example 4: NMR Spectroscopy of Block Copolymer PRx0729v6. (FIG. 2)

This example provides evidence, using NMR spectroscopy, that polymer PRx0729v6 forms a micelle-like structure in aqueous solution.

$^1$H NMR spectra were recorded on Bruker AV301 in deuterated chloroform ($CDCl_3$) and deuterated water ($D_2O$) at 25° C. A deuterium lock ($CDCl_3$, $D_2O$) was used, and chemical shifts were determined in ppm from tetramethylsilane (for $CDCl_3$) and 3-(trimethylsilyl)propionic-2,2,3,3-d4 acid, sodium salt (for $D_2O$). Polymer concentration was 6 mg/ml.

NMR spectroscopy of the synthesized polymer, using polymer PRx0729v6 as an example, in aqueous buffer provided evidence that the diblock polymers of the present invention form micelles in aqueous solution. Formation of micelles results in the formation of a shielded viscous internal core that restricts the motion of the protons forming the core segments and prevents deuterium exchange between the solvent and the protons of the core. This is reflected by a significance suppression or disappearance of the $^1$H NMR signals of the corresponding protons. We used this inherent property of solution NMR spectroscopy to show that the hydrophobic block of the core of the micelle is effectively shielded. If micelles are formed in aqueous media, a disappearance of the signals due to the protons of the hydrophobic copolymer block should occur.

Figure 2B:
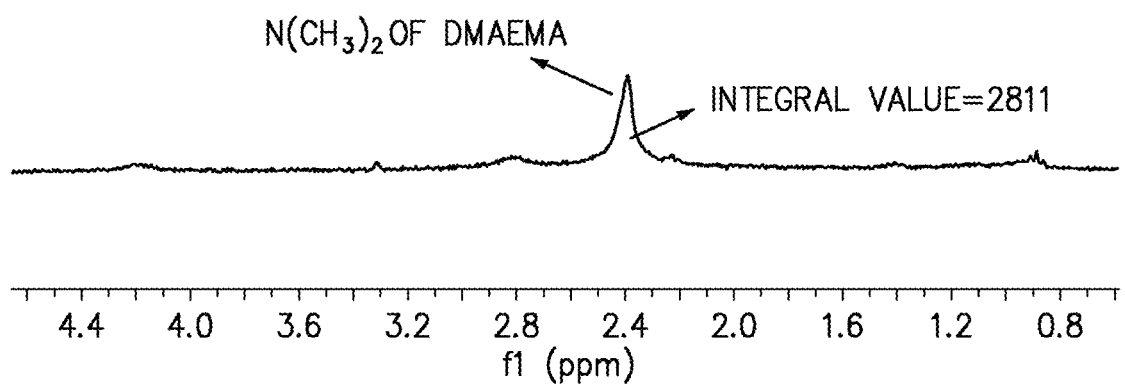

FIG. 2 shows the $^1$H NMR experiments of polymer PRx0729v6 in $CDCl_3$ (organic solvent) and $D_2O$ (aqueous solvent). The $^1$H NMR spectrum of polymer in $CDCl_3$ at room temperature (FIG. 1A) shows the signals attributed to all polymer protons indicating that the polymer chains remain dispersed (non-aggregated) in $CDCl_3$ and preserve their motion so their protons can exchange with the solvent. This indicates that stable micelles with shielded cores are not formed from PRx0729v6 in organic solvent. FIG. 2B shows the $^1$H NMR spectra of PRx0729v6 in $D_2O$. The signals representing the protons of the hydrophobic block (BMA, PAA, DMAEMA) disappear from the spectrum. This indicates that stable micelles with shielded cores are formed from PRx0729v6 in aqueous solution. Moreover, in the same spectrum, the signal attributed to the resonance of the protons of the two methyl groups of the DMAEMA (2.28 ppm) undergoes a significant suppression, implying that only the first poly DMAEMA block constituting the shell is exposed to water, i.e., mainly the charged group of DMAEMA. A simple calculation indicates that the integrated percentage of PAA, DMAEMA of the hydrophobic block (2900) subtracted from the signal in $CDCl_3$ (5600) gives the approximate value for the same signal in $D_2O$ (2811), consistent with this conclusion.

Taken together, the results of $^1$H NMR experiments indicate that polymer PRx0729v6 forms micelles with an ordered core-shell structure where the first block polyDMAEMA forms a hydrated outer shell surrounding a core composed of hydrophobic units (BMA) and electrostatically stabilizing units of opposite charge (PAA, DMAEMA).

Figure 3:
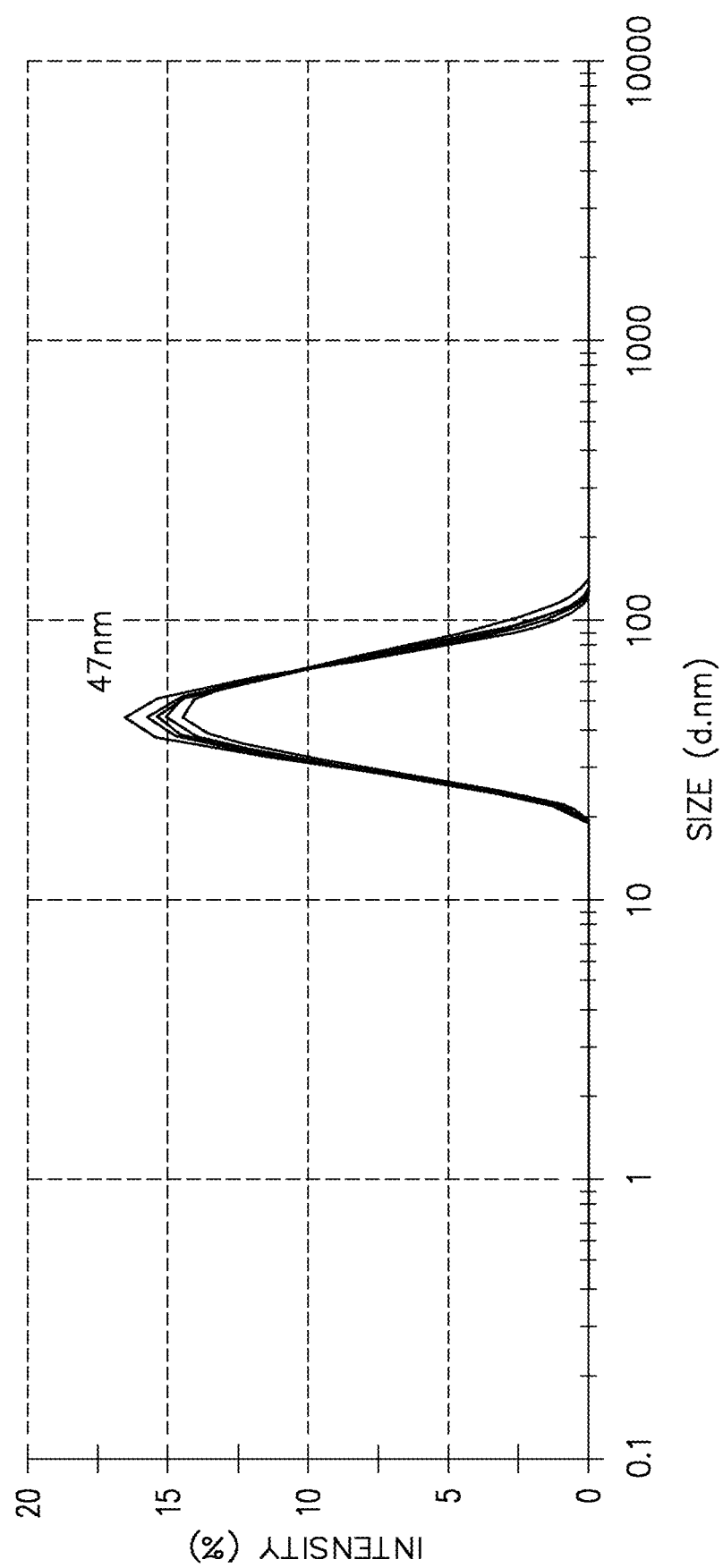
FIG. 3: An illustrative example of the dynamic light scattering (DLS) determination of particle size of polymer PRx0729v6 complexed to siRNA.

Example 5: Dynamic Light Scattering (DLS) Determination of Particle Size of Polymer PRx0729v6 Complexed to siRNA. (FIG. 3)

The following example demonstrates that polymer PRx0729v6 forms uniform particles 45 nm in size either alone or 47 nm in size following binding to siRNA.

Particle sizes of polymer alone or polymer/siRNA complexes were measured by dynamic light scattering using a Malvern Zetasizer Nano ZS. Polymers were measured in phosphate buffered saline, pH 7.4 (PBS) at 1 mg/ml for PRx0729v6 alone or at 0.7 mg/ml PRx0729v6 complexed to 1 uM GAPDH-specific 21 mer-siRNA (Ambion), with a theoretical charge ratio of 4:1, positive charges on polymer: negative charges on siRNA. PRx0729v6 alone (45 nm) and PRx0729v6 complexed to siRNA (47 nm) (FIG. 3) show similar particle sizes with a near uniform distribution, PDI <0.1.

Figure 4:
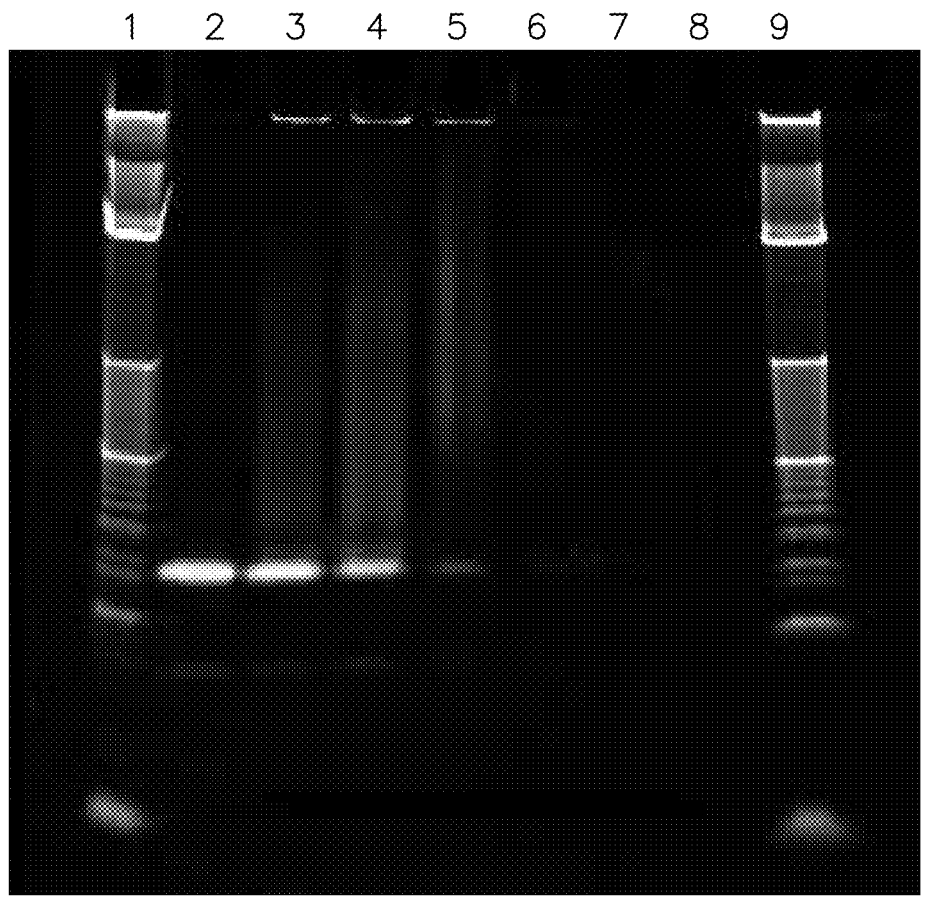
FIG. 4: An illustrative example of the gel shift analysis of polymer PRx0729v6/siRNA complexes at different charge ratios.

Example 6: Gel Shift Analysis of Polymer PRx0729v6/siRNA Complexes at Different Charge Ratios (FIG. 4)

The following example demonstrates that polymer PRx0729v6 binds to siRNA at various charge ratios resulting in a complex with reduced electrophoretic mobility.

Polymer siRNA binding was analyzed by gel electrophoresis (FIG. 4) and demonstrates that complete siRNA binding to polymer occurs at a polymer/siRNA charge ratio of 4:1 and higher.

Figure 5:
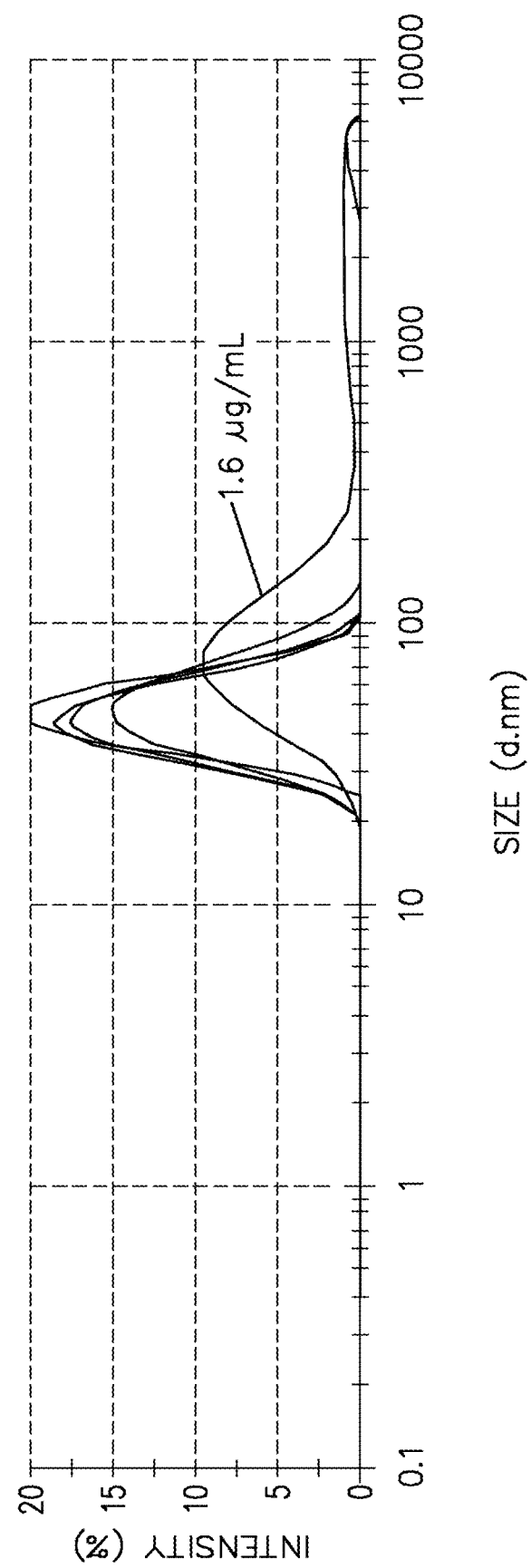
FIG. 5: An illustrative example of the critical stability concentration (CSC) of polymer PRx0729v6.

Example 7. Critical Stability Concentration (CSC) of Polymer PRx0729v6. (FIG. 5)

The following example demonstrates that the micelle particle property of polymer PRx0729v6 is stable to 100-fold dilution.

Polymer PRx0729v6 was dissolved in PBS buffer pH 7.4 at a concentration of 1 mg/ml ±0.5 M NaCl. Particle size was measured by dynamic light scattering over a 5-fold range of serial dilutions from 1 mg/ml to 1.6 ug/ml with PBS ±0.5 M NaCl. FIG. 5 shows that a particle size of about 45 nm is stable down to a concentration of about 10ug/ml. Polymer PRx0729v6 appears to be unstable below about 5 ug/ml (the critical stability concentration or CMC) where individual polymer chains dissociate and form non-specific aggregates.

Figure 6:
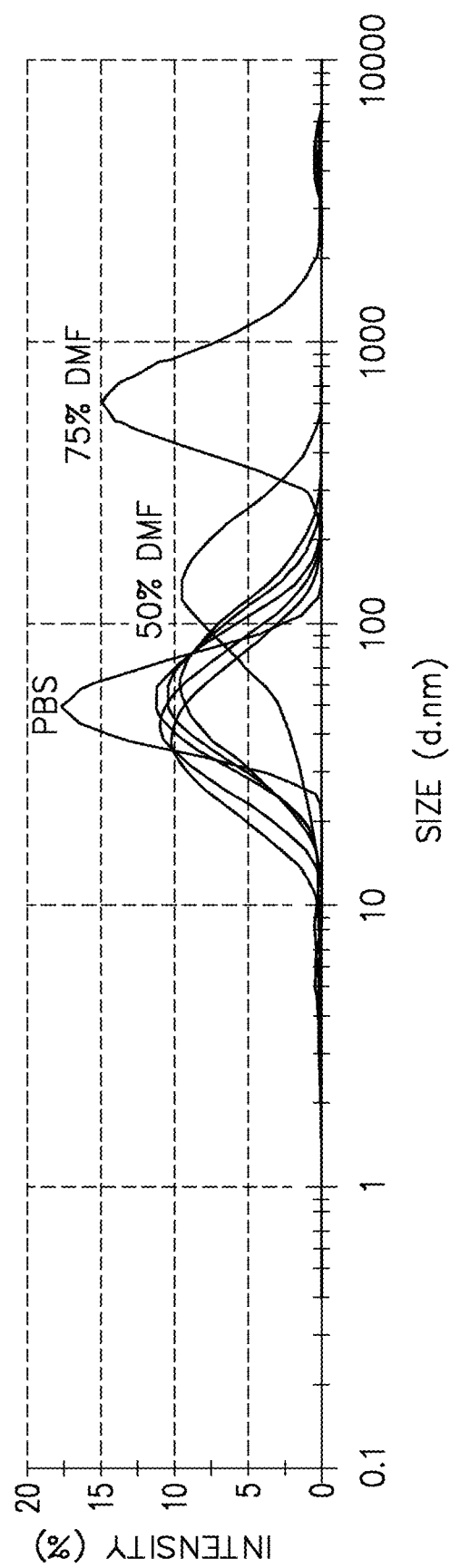
FIG. 6: An illustrative example of the polymer PRx0729v6 particle stability in organic solvents.

Example 8. Polymer PRx0729v6 Particle Stability in Organic Solvents. (FIG. 6)

This example demonstrates that the micelle structure of polymer PRx0729v6 is dissociated in organic solvents, consistent with the hydrophobic nature of the micelle core.

Polymer PRx0729v6 was dissolved in various organic solvents at a concentration of 1 mg/ml and particle size was measured by dynamic light scattering. FIG. 6 shows that increasing concentration of dimethylformamide (DMF) results in micelle dissociation to aggregated chains.

Example 9: Conjugation of siRNA with Micellic Assembly

A. Conjugation of double-stranded siRNA with thiol-containing block copolymer.

[siRNA-pyridyl disulfide was prepared by dissolving amino-siRNA at 10 mg/nil in 50 mM sodium phosphate, 0.15 M NaCl, pH 7.2 or another non-amine buffers, e.g., borate, Hepes, bicarbonate with the pH in the range appropriate for the NHS ester modification (pH 7-9). SPDP was dissolved at a concentration of 6.2 mg/ml in DMSO (20 mM stock solution), and 25 ul of the SPDP stock solution was added to each ml of amino-siRNA to be modified. The solution was mixed and reacted for at least 30 min at room temperature. Longer reaction times (including overnight) did not adversely affect the modification. The modified RNA (pyridyl disulfide) was purified from reaction by-products by dialysis (or gel filtration) using 50 mM sodium phosphate, 0.15 M NaCl, 10 mM EDTA, pH 7.2. The prepared siRNA-pyridyl disulfide was reacted at a 1:5 molar ratio with polymer PRx0729v6 (containing a free thiol at the ω-end) in the presence of 10-50 mM EDTA in PBS, pH 7.2. Extent of reaction was monitored spectrophotometrically by release of pyridine-2-thione and by gel electrophoresis.

B. Conjugation of single stranded RNA with polymer followed by annealing of the second strand.

Single-stranded RNA pyridyl disulfide conjugate was prepared using the procedure of the above example starting with a single stranded amino modified RNA. After the coupling of the RNA pyridyl disulfide with the block copolymer micelle, the complementary RNA strain is added to the reaction mixture, and the two strands are allowed to anneal for 1 hr at a temperature approximately 20° C. below the Tm of the duplex RNA.

Example 10: Knock-Down Activity of siRNA-Micellic Assembly Complexes in Cultured Mammalian Cells. (FIG. 7 and FIG. 12)

Knock-down (KD) activity of siRNA/polymer PRx0729v6 complexes was assayed in 96-well format by measuring specific gene expression after 24 hours of treatment with PRx0729v6:siRNA complexes. Polymer and GAPDH targeting siRNA or negative control siRNA (Ambion) were mixed in 25 uL to obtain various charge ratios and concentrations at 5-fold over final transfection concentration and allowed to complex for 30 minutes before addition to HeLa cells in 100 uL normal media containing 10% FBS. Final siRNA concentrations were evaluated at 100, 50, 25, and 12.5 nM. Polymer was added either at 4:1, 2:1 or 1:1 charge ratios, or at fixed polymer concentrations of 18, 9, 4.5, and 2.2 ug/ml to determine what conditions result in highest KD activity. For charge ratios (FIG. 7A), the complexes were prepared at higher concentrations, incubated for 30 minutes, and then serial diluted at 5-fold over concentration shown on graphs just prior to addition to cells. For fixed polymer concentration (FIG. 7B), the siRNA and polymer were complexed at 5-fold over concentrations shown on graph, incubated for 30 minutes then added to cells for final concentrations shown. FIG. 7C is the negative control. Total RNA was isolated 24 hours post treatment and GAPDH expression was measured relative to 2 internal normalizer genes, RPL 13A and HPRT, by quantitative PCR. Results in FIG. 7 and FIG. 12A and FIG. 12B indicate >60% KD activity (shading) obtained with PRx0729v6 at 9 ug/ml and higher concentrations at all siRNA concentrations tested. This concentration was coincident with stable micelle formation from particle size analyses. High KD activity was observed with 4.5 ug/ml PRx0729v6/12.5 nM siRNA only when complexes were prepared at high concentration and serial diluted (4:1 charge ratio) as compared to complex formation at lower concentration (4.5 ug/ml fixed polymer concentration). Additionally, only 100 nM siRNA with 4.5 ug/ml PRx0729v6 showed high KD activity whereas lower siRNA concentrations did not. In summary, PRx0729v6 micelles were stable to dilution down to ~10 ug/ml and KD activity is lost below ~5 ug/ml, indicating that stable micelles are required for good KD activity.

Example 11: Knock-Down Activity of Dicer Substrate GAPDH siRNA—Polymer Complexes in Cultured Mammalian Cells Knock-down (KD) activity of GAPDH specific dicer substrate siRNA/polymer complexes is assayed in a 96-well format by measuring GAPDH gene expression after 24 hours of treatment with polymer: GAPDH dicer siRNA complexes. The GAPDH dicer siRNA sequence is: sense strand: TGrGrUrCrArUrCrCrArUrGrArCrArArCrUrUrUrGrGrUrAdTdC (SEQ ID NO:1), antisense strand: TGrArUrArCrCrArArArGrUrUrGrUrCrArUrGrGrArUrGrArCrCrUrU (SEQ ID NO:2). Polymer and GAPDH targeting siRNA or negative control siRNA (IDT) are mixed in 25 uL to obtain various charge ratios and concentrations at 5-fold over final transfection concentration and allowed to complex for 30 minutes before addition to HeLa cells in 100 uL normal media containing 10% FBS. Final siRNA concentrations are examined at 100, 50, 25, and 12.5 nM. Polymer is added either at 4:1, 2:1 or 1:1 charge ratios, or at fixed polymer concentrations of 40, 20, 10, and 5 ug/ml to determine what condition results in highest KD activity. Total RNA is isolated 24 hours post treatment and GAPDH expression is measured relative to 2 internal normalizer genes, RPL13A and HPRT, by quantitative PCR. Results show >60% KD activity obtained with polymer at 10 ug/ml and higher concentrations at all siRNA concentrations tested. This polymer concentration is coincident with stable micelle formation from particle size analyses.

Example 12: Knock-Down Activity of ApoB100 siRNA-Polymer Complexes in Cultured Mammalian Cells Knock-down (KD) activity of ApoB100 specific siRNA or dicer substrate siRNA complexed to polymer is assayed in a 96-well format by evaluating ApoB100 gene expression after 24 hours of treatment with polymer: ApoB siRNA complexes. The ApoB100 siRNA sequence is: sense strand: 5'-rGrAr ArUrGrUrGrGrGrUrGrGrCrAr ArCrUrUrUrArG-3' (SEQ ID NO:3), antisense strand: 5'-TArArArGrUrUrGrCrCrArCrCrCrArCrArUrUrCrArG-S' (SEQ ID NO:4). The ApoB100 dicer substrate siRNA sequence is: sense strand:

5'-TGrArArUrGrUrGrGrGrUrGrGrCrArArCrUrUrUrArArArGdGdA (SEQ ID NO:5), antisense strand: 5'-TUrCrCrUrUrUrArArArGrUrUrGrCrCrArCrCrCrArCrArUrCrArG-S' (SEQ ID NO:6). Polymer and ApoB targeting siRNA or negative control siRNA (IDT) are mixed in 25 uL to obtain various charge ratios and concentrations at 5-fold over final transfection concentration and allowed to complex for 30 minutes before addition to HepG2 cells in 100 uL normal media containing 10% FBS. Final siRNA concentrations are examined at 100, 50, 25, and 12.5 nM. Polymer is added either at 4:1, 2:1 or 1:1 charge ratios, or at fixed polymer concentrations of 40, 20, 10, and 5 ug/ml to determine what condition results in highest KD activity. Total RNA is isolated 24 hours post treatment and ApoB100 expression is measured relative to 2 internal normalizer genes, RPL13A and HPRT, by quantitative PCR. Results show >60% KD activity obtained with polymer at 10 ug/ml and higher concentrations at all siRNA concentrations tested. This polymer concentration is coincident with stable micelle formation from particle size analyses.

Example 13: Knock-Down Activity of ApoB100 siRNA-Polymer Complexes in a Mouse Model The knockdown activity of ApoB100 specific siRNA/polymer complexes is determined in a mouse model by measuring ApoB100 expression in liver tissue and serum cholesterol levels. Balb/C mice are dosed intravenously via the tail vein with 1, 2 or 5 mg/kg ApoB specific siRNA complexed to polymer at 1:1, 2:1 or 4:1 charge ratio (polymer: siRNA) or saline control. 48 hours post final dose mice are sacrificed and blood and liver samples are isolated. Cholesterol levels are measured in serum. Total RNA is isolated from liver and ApoB100 expression is measured relative to 2 normalizer genes, HPRT and GAPDH by quantitative PCR.

Example 14. Knock-Down Activity of ApoB100 Antisense DNA Oligonucleotide-Polymer Complexes in Cultured Mammalian Cells Knock-down (KD) capability by ApoB100 specific antisense DNA oligonucleotide complexed to polymer is assayed in a 96-well format by measuring ApoB 100 gene expression after 24 hours of treatment with polymer: ApoB antisense DNA oligonucleotide complexes. Two ApoB100 antisense oligonucleotides specific to mouse ApoB are:

```
                                      (SEQ ID NO: 7)
5'-GTCCCTGAAGATGTCAATGC-S', position 541 of the
coding region
and (SEQ ID NO: 8)
5'-ATGTCAATGCCACATGTCCA-S', position 531 of the
coding region
```

Polymer and an ApoB targeting antisense DNA oligonucleotide or negative control DNA oligonucleotide (scrambled sequence) are mixed in 25 uL to obtain various charge ratios and concentrations at 5-fold over final transfection concentration and allowed to complex for 30 minutes before addition to HepG2 cells in 100 uL normal media containing 10% FBS. Final oligonucleotide concentrations are examined at 100, 50, 25, and 12.5 nM. Polymer is added either at 4:1, 2:1 or 1:1 charge ratios, or at fixed polymer concentrations of 40, 20, 10, and 5 ug/ml to determine what condition results in the highest KD activity. Total RNA is isolated 24 hours post treatment and ApoB100 expression is measured relative to 2 internal normalizer genes, RPL1 3 A and HPRT, by quantitative PCR.

Figure 8B:
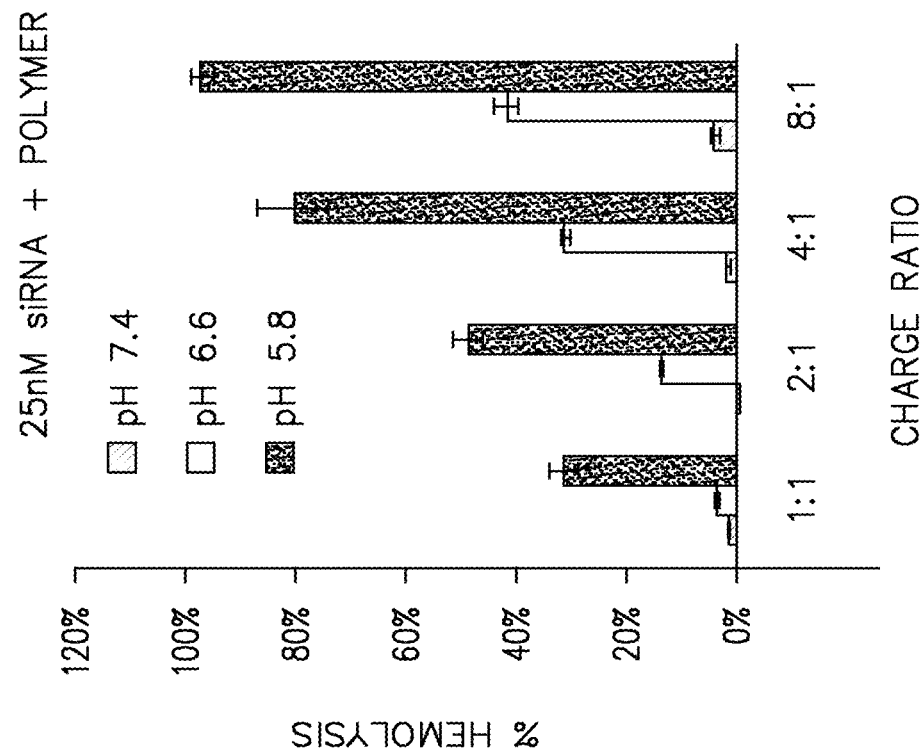
FIGS. 8A and 8B: illustrative demonstrations of membrane destabilizing activity of polymeric micelles and their siRNA complexes.
Figure 8A:
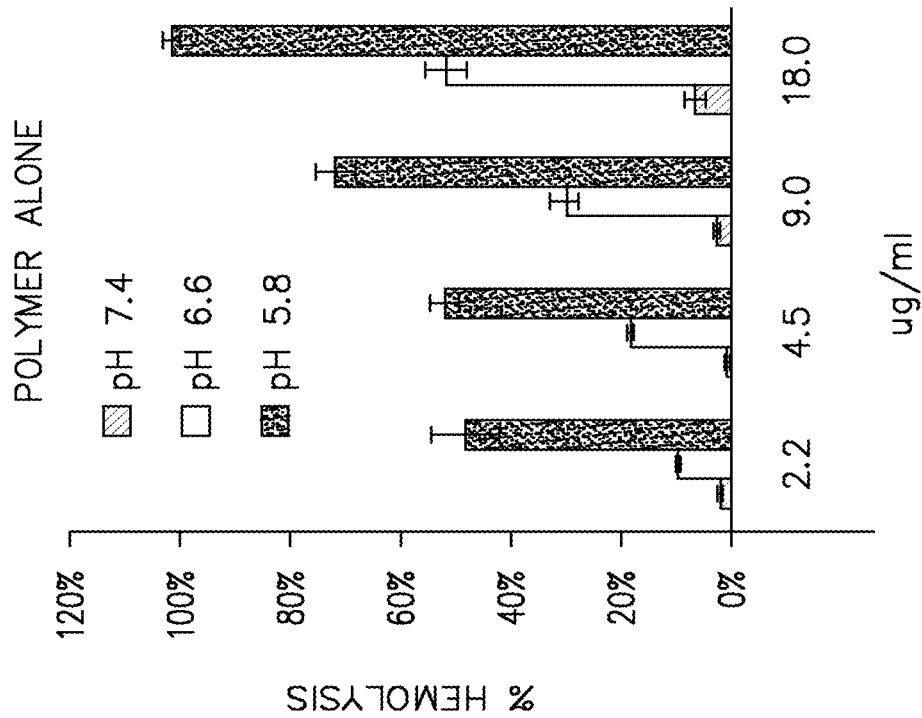

Example 15: Demonstration of Membrane Destabilizing Activity of Micellic Assemblies and their siRNA Complexes (FIG. 8)

pH responsive membrane destabilizing activity was assayed by titrating polymer alone or PRx0729v6:siRNA complexes into preparations of human red blood cells (RBC) and determining membrane-lytic activity by hemoglobin release (absorbance reading at 540 nm). Three different pH conditions were used to mimic endosomal pH environments (extracellular pH=7.4, early endosome=6.6, late endosome=5.8). Human red blood cells (RBC) were isolated by centrifugation from whole blood collected in vaccutainers containing EDTA. RBC were washed 3 times in normal saline, and brought to a final concentration of 2% RBC in PBS at specific pH (5.8, 6.6 or 7.4). PRx0729v6 alone or PRx0729v6/siRNA complex was tested at concentrations just above and below the critical stability concentration (CSC) as shown (FIG. 5). For polymer/siRNA complex, 25 nM siRNA was added to PRx0729v6 at 1:1, 2:1, 4:1 and 8:1 charge ratios (same polymer concentrations for polymer alone). Solutions of polymer alone or polymer-siRNA complexes were formed at 20X final assayed concentration for 30 minutes and diluted into each RBC preparation. Two different preparations of PRx0729v6 polymer stock were compared for stability of activity at 9 and 15 days post preparation, stored at 4° C. from day of preparation. RBC with polymer alone or polymer/siRNA complex were incubated at 37° C. for 60 minutes and centrifuged to remove intact RBC. Supernatants were transferred to cuvettes and absorbance determined at 540 nm. Percent hemolysis is expressed as $A_{540}$ sample/$A_{540}$ of 1% Triton X-100 treated RBC (control for 100% Lysis). The results show that PRx0729v6 alone (FIG. 8A) or PRx0729v6/siRNA complex (FIG. 8B) is non-hemolytic at pH 7.4 and becomes increasingly more hemolytic at the lower pH values associated with endosomes and at higher concentrations of polymer.

Figure 9:
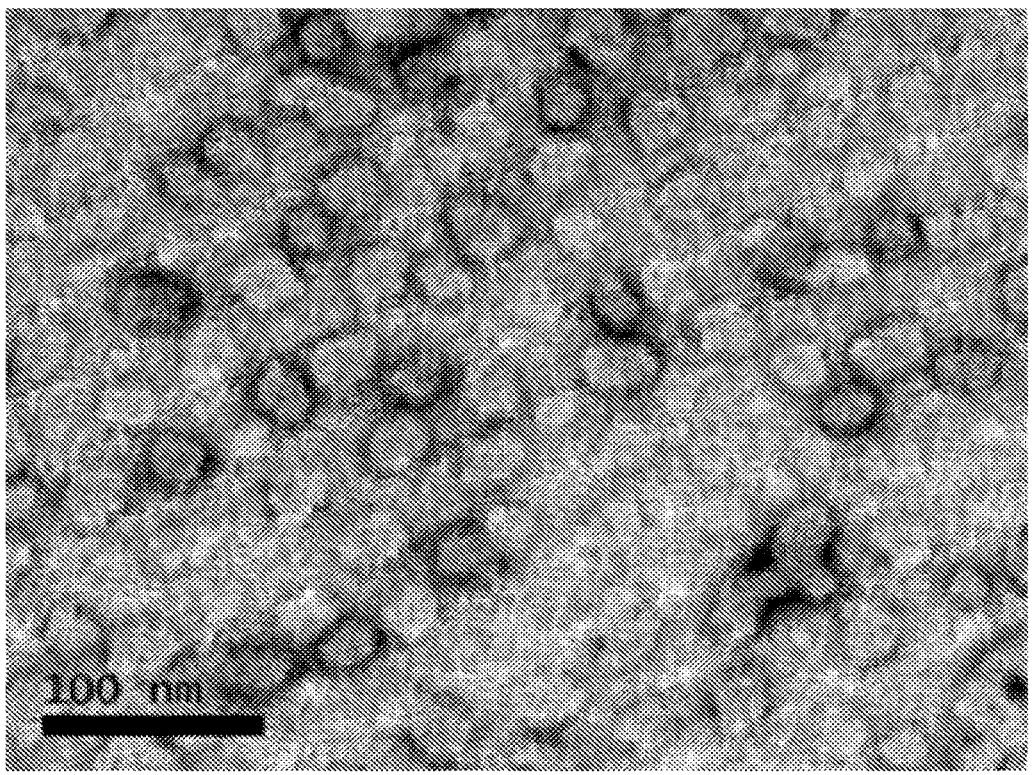
FIG. 9: An illustrative transmission electron microscopy (TEM) analysis of polymer PRx0729v6.

Example 16: Transmission Electron Microscopy (TEM) Analysis of Polymer PRx0729v6. (FIG. 9)

This example provides evidence, using electron spectroscopy, that the polymer PRx0729v6 forms spherical micelle-like particles.

A 0.5 mg/ml solution of polymer PRx0729v6 in PBS was applied to a carbon coated copper grid for 30 minutes. The grid was fixed in Karnovsky's solution and washed in cacodylate buffer once and then in water 8 times. The grid was stained with a 6% solution of uranyl acetate for 15 minutes and then dried until analysis. Transmission electron microscopy (TEM) was carried out on a JEOL microscope. FIG. 9 shows a typical electron micrograph of polymer PRx0729v6 demonstrating spherical particles with approximate dimensions similar to those determined in solution by dynamic light scattering.

Example 17. Fluorescence Microscopy of Cell Uptake and Intracellular Distribution of Polymer-siRNA Complexes. (FIG. 10)

This example demonstrates that polymer PRx0729v6 can mediate a more efficient cellular uptake of fluorescent-labeled siRNA and endosomal release than a lipid-based transfection reagent.

Figure 10A:
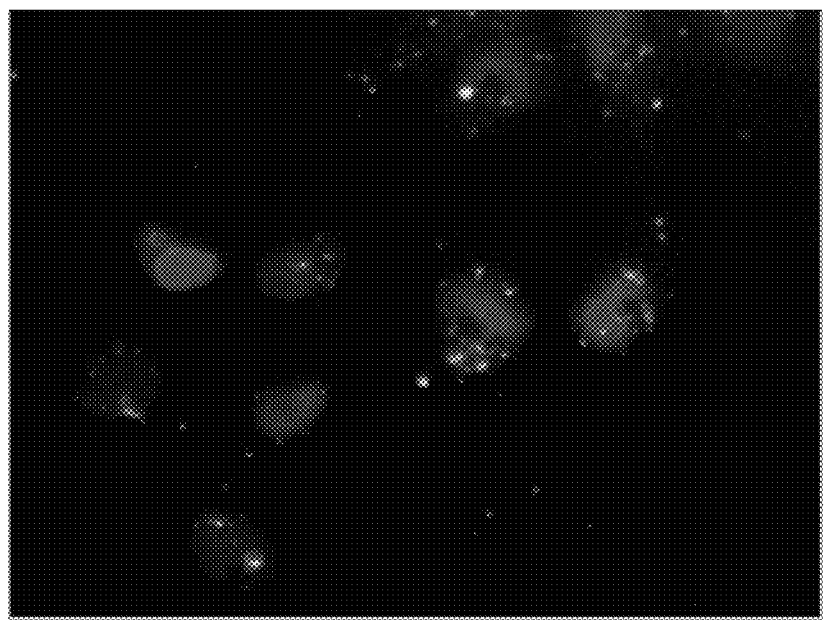
FIGS. 10A and 10B: illustrative fluorescence micrographs of cell uptake and intracellular distribution of polymer-siRNA complexes.
Figure 10B:
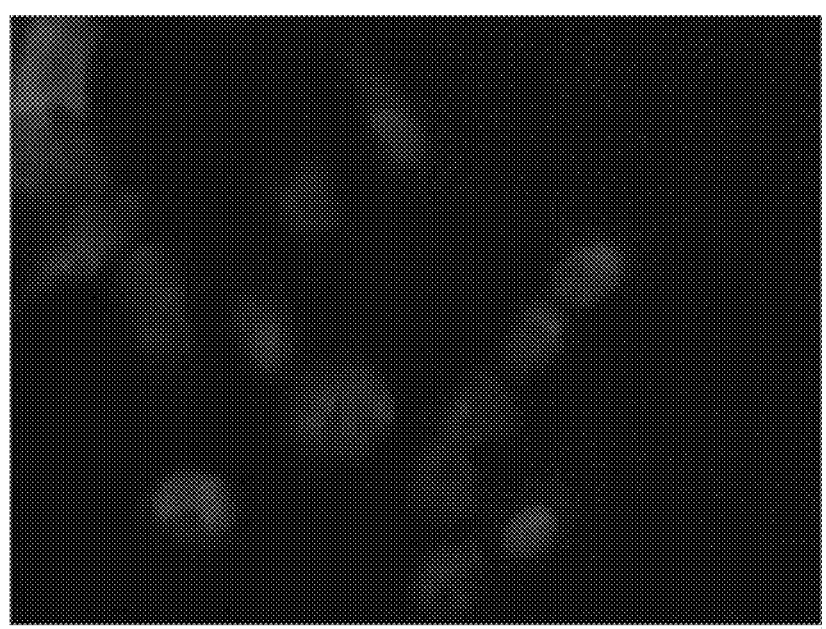

HeLa cells were plated on a Lab-Tek II chambered coverglass. Following overnight incubation, cells were transfected with either 100 nM FAM-siRNA/lipofectamine 2000 or with 100 nM FAM-siRNA at a Polymer-siRNA 4:1 charge ratio. Complexes were formed in PBS pH 7.4 for 30 minutes at a 5X concentration, added to cells for final 1X concentration, and incubated overnight. Cells were stained with DAPI (for visualization of the nucleus) for 10 minutes and then fixed in 3.7% formaldehyde-1X PBS for 5 minutes and washed with PBS. Samples were imaged with a Zeiss Axiovert fluorescent microscope. FIG. 10B shows the fluorescence microscopy of cell uptake and intracellular distribution of polymer-siRNA compared to lipofectamine (FIG. 10A). Particulate staining of lipofectamine-siRNA complexes suggest an endosomal location, while diffuse cytoplasmic staining of polymer-siRNA complexes indicate they have been released from endosomes into the cytoplasm.

Example 18. Uptake of Small Hydrophobic Molecules into Polymer PRx0729v6 Micellic Assemblies This example demonstrates that small hydrophobic molecules are taken up by the predominantly hydrophobic micelle core of polymer PRx0729v6.

The formation of polymer micelles with or without siRNA is confirmed by a fluorescence probe technique using pyrene ($C_{16}H_{10}$, MW=202), in which the partitioning of pyrene into the micellar core could be determined using the ratio of 2 emission maxima of the pyrene spectrum. The fluorescence emission spectrum of pyrene in the polymer micelle solution is measured from 300 to 360 nm using a fixed excitation wavelength of 395 nm with a constant pyrene concentration of $6 \times 10^{-7}$ M. The polymer varies from 0.001% to 20% (w/w) with or without 100 nM siRNA. The spectral data are acquired using a Varian fluorescence spectrophotometer. All fluorescence experiments are carried out at 25° C. The critical micelle concentration (CMC) is determined by plotting the intensity ratio $I_{336}/I_{333}$ as a function of polymer concentration.

Similarly, a model small molecule drug, dipyridamole (2-{[9-(bis(2-hydroxyethyl) amino)-2,7 -bis (1-piperidyl)-3,5,8,10-tetrazabicyclo[4.4.0]deca-2,4,7,9,11-pentaen-4-yl]-(2-hydroxyethyl)amino}ethanol; $C_{24}H_{40}N_8O_4$, MW=505) is incorporated into the micelle core of PRx0729v6 as follows. Polymer (1.0 mg) and dipyridamole (DIP) (0.2 mg) are dissolved in THF (0.5 mL). Deionized water (10 inL) is added dropwise and the solution is stirred at 50° C. for 6 h to incorporate the drug into the hydrophobic core of the micelle. The solution (2.5 mL) is divided, and the absorbance of dipyridamole is measured at 415 nm by UV-vis spectroscopy at 25 and 37° C. Control measurements are also conducted by measuring the time-dependent reduction in dipyridamole absorbance in deionized water in the absence of copolymer. The absorbance at both 25 and 37° C. is measured for each time point, and the value is subtracted from that observed in the solution.

Example 19. Effect of pH on Polymer Structure. (FIG. 11)

This example demonstrates that the micelle structure of polymer PRx0729v6.2 is dissociated upon lowering the pH from 7.4 to 4.7.

Particle Size of polymer PRx0729v6.2 was measured by dynamic light scattering at pH 7.4 and a series of acidic pH values down to pH4.7 in PBS at 5-fold serial dilutions from 0.5 mg/ml-0.004 mg/ml. FIG. 11A shows that at pH 7.4, the polymer is stable to dilution down to 4 ug/ml where it begins to dissociate to a form that produces aggregates. FIG. 11B shows that at increasing acidic pH values down to pH 4.7 the polymer dissociation from a micelle structure is enhanced, that is, occurs at higher polymer concentrations, and produces increasing levels of polymer monomers from 1-8 nm in size.

Example 20: Methods for Conjugating Targeting Ligands and Polynucleotides to a Copolymer The following examples demonstrate methods for conjugating a targeting ligand (for example, galactose) or a polynucleotide therapeutic (for example siRNA) to a diblock copolymer. (1) The polymer is prepared using reversible addition fragmentation chain transfer (RAFT) (Chiefari et al. *Macromolecules*. 1998; 31(16):5559-5562) to form a galactose end-functionalized, diblock copolymer, using a chain transfer agent with galactose as the R-group substituent. (2) The first block of a diblock copolymer is prepared as a copolymer containing methylacrylic acid-N-hydroxy succinamide (MAA(NHS)) where a galactose-PEG-amine is conjugated to the NHS groups or where an amino-disulfide siRNA is conjugated to the NHS, or where pyridyl disulfide amine is reacted with the NHS groups to form a pyridyl disulfide that is subsequently reacted with thiolated RNA to form a polymer-RNA conjugate.

Example 20.1: Preparation of Galactose-PEG-Amine and Galactose-CTA

Scheme 1 illustrates the synthesis scheme for galactose-PEG-amine (compound 3) and the galactose-CTA (chain transfer agent) (compound 4).

Compound 1: Pentaacetate galactose (10 g, 25.6 mmol) and 2-(2-(2-Chloroethoxy)ethoxy]ethanol (5.6 mL, 38.4 mmol) were dissolved in dry $CH_2Cl_2$ (64 inL) and the reaction mixture was stirred at RT for 1 h. The $BF_3$, $OEt_2$ (9.5 ml, 76.8 mmol) was added to the previous mixture dropwise over 1 h in an ice bath. The reaction mixture was stirred at room temperature (RT) for 48 h. After the reaction, 30 mL of $CH_2Cl_2$ was added to dilute the reaction. The organic layer was neutralized with saturated $NaHCO_{3(aq)}$, washed by brine and then dried by $MgSO_4$. The $CH_2Cl_2$ was removed under reduced pressure to get the crude product. The crude product was purified by flash column chromatography to get final product 1 as slight yellow oil. Yield: 55% TLC ($I_2$ and p-Anisaldhyde): EA/Hex: 1/1 (Rf: β=0.33; α=0.32; unreacted S.M 0.30).

Compound 2: Compound 1 (1.46 g, 2.9 mmol) was dissolved in dry DMF (35 mL) and the $NaN_3$ (1.5 g, 23.2 mmol) was added to the mixture at RT. The reaction mixture was heated to 85-90 C overnight. After the reaction, EA (15 mL) was added to the solution and water (50 mL) was used to wash the organic layer 5 times. The organic layer was dried by $MgSO_4$ and purified by flash column chromatography to get compound 2 as a colorless oil. Yield: 80%, TLC (12 and p-Anisaldhyde): EA/Hex: 1/1 (Rf: 0.33).

Compound 3: Compound 2 (1.034 g, 2.05 mmol) was dissolved in MeOH (24 mL) and bubbled with $N_2$ for 10 min and then Pd/C (10%) (90 mg) and TFA (80 uL) were added to the previous solution. The reaction mixture was bubbled again with $H_2$ for 30 nin and then the reaction was stirred at RT under $H_2$ for another 3 h. The Pd/C was removed by celite and MeOH was evaporated to get the compound 3 as a sticky gel. Compound 3 can be used without further purification. Yield: 95%. TLC (p-Anisaldhyde): MeOH/$CH_2Cl_2$: 1/4 (Rf: 0.05).

Compound 4: ECT (0.5 g, 1.9 mmol), NHS (0.33 g, 2.85 mmol) and DCC (0.45 g, 2.19 mmol) were dissolved in $CHCl_3$ (15 mL) at 0 C. The reaction mixture was continuously stirred at RT overnight. Compound 3 (1.13 g, 1.9 mmol) and TEA (0.28 mL, 2.00 mmol) in $CHCl_3$ (10 mL) were added slowly to the previous reaction at 0 C. The reaction mixture was continuously stirred at RT overnight. The $CH_3Cl$ was removed under reduced pressure and the crude product was purified by flash column chromatography to get the compound 4 as a yellow gel. Yield (35%). TLC: MeOH/$CH_2Cl_2$: 1/9 (Rf: 0.75)

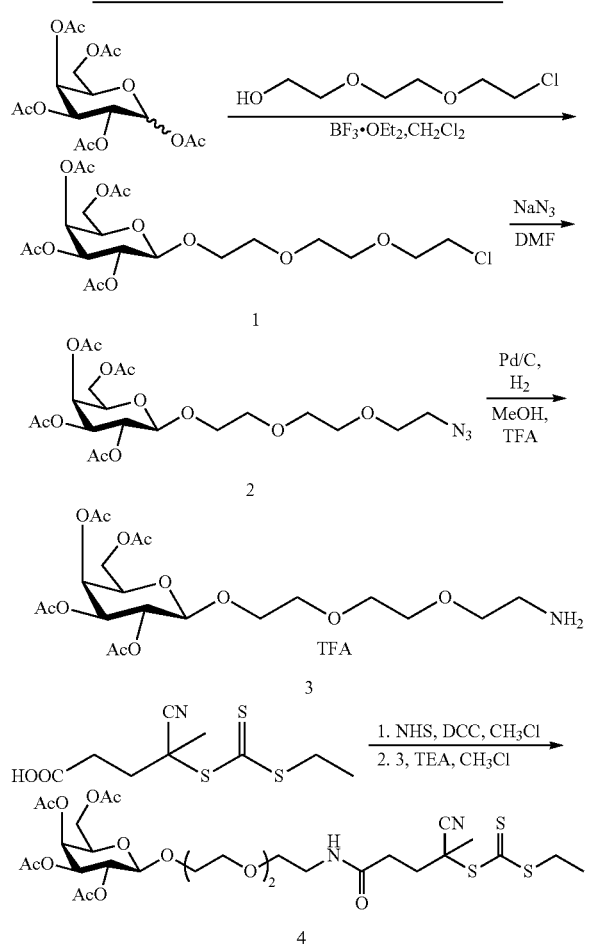

Scheme 1. Synthesis of galactose-PEG-amine (cpd 3) and galactose-CTA (cpd 4)

Example 20.2: Synthesis of [DMAEMA]-[BMA-PAA-DMAEMA]

A. Synthesis of DMAEMA macroCTA.

Polymerization: In a 20 mL glass vial (with a septa cap) was added 33.5 mg ECT (RAFT CTA), 2.1 mg AIBN (recrystallized twice from methanol), 3.0 g DMAEMA (Aldrich, 98%, was passed through a small alumina column just before use to remove the inhibitor) and 3.0 g DMF (high purity without inhibitor). The glass vial was closed with the Septa Cap and purged with dry nitrogen (carried out in an ice bath under stirring) for 30 min. The reaction vial was placed in a preheated reaction block at 70° C. The reaction mixture was stirred for 2 h 40 min. The septa cap was opened and the mixture was stirred in the vial in an ice bath for 2-3 minutes to stop the polymerization reaction.

Purification: 3 mL of acetone was added to the reaction mixture. In a 300 mL beaker was added 240 mL hexane and 60 mL ether (80/20 (v/v)) and under stirring the reaction mixture was added drop by drop to the beaker. Initially this produces an oil which is collected by spinning down the cloudy solution; yield=1.35 g (45%). Several precipitations were performed (e.g., 6 times) in hexane/ether (80/20 (v/v)) mixed solvents from acetone solution. Finally, the polymer was dried under vacuum for 8 h at RT; yield 1 g. Summary: ($M_{n,theory}$=11,000 g/mol at 45% cony.)

| Name | FW (g/mol) | Equiv. | mol | Weight | Actual weight |
|---|---|---|---|---|---|
| DMAEMA | 157.21 | 150 | 0.0191 | 3.0 G | 3.01 G |
| ECT | 263.4 | 1 | $1.2722 \times 10^{-4}$ | 33.5 mg | 33.8 mg |
| AIBN | 164.21 | 0.1 | $1.2722 \times 10^{-5}$ | 2.1 mg | 2.3 mg |

DMF = 3.0 g; $N_2$ Purging: 30 min; Conduct polymerization at 70° C. for 2 h 45 min.

B. Synthesis of TBMA-PA A-DMAEMA1 from DMAEMA macroCTA

All chemicals and reagents were purchased from Sigma-Aldrich Company unless specified. Butyl methacrylate (BMA) (99%), 2-(Dimethylamino) ethyl methacrylate (DMAEMA) (98%) were passed through a column of basic alumina (150 mesh) to remove the polymerization inhibitor. 2-propyl acrylic acid (PAA) (>99%) was purchased without inhibitor and used as received. Azobisisobutyronitrile (AIBN) (99%) was recrystallized from methanol and dried under vacuum. The DMAEMA macroCTA was synthesized and purified as described above (Mn-10000; PDI~1.3; >98%). N, N-Dimethylformamide (DMF) (99.99%) (Purchased from EMD) was reagent grade and used as received. Hexane, pentane and ether were purchased from EMD and they were used as received for polymer purification.

Polymerization: BMA (2.1 g, 14.7 mmoles), PAA (0.8389 g, 7.5 mmoles), DMAEMA (1.156 g, 7.35 mmoles), MacroCTA (0.8 g, 0.0816 mmoles), AIBN (1.34 mg, 0.00816 mmoles; CTA:AIBN 10:1) and DMF (5.34 ml) were added under nitrogen in a sealed vial. The CTA:Monomers ratio used was 1:360 (assuming 50% of conversion). The monomers concentration was 3 M. The mixture was then degassed by bubbling nitrogen into the mixture for 30 minutes and then placed in a heater block (Thermometer: 67° C.; display: 70-71; stirring speed 300-400 rpm). The reaction was left for 6 hours, then stopped by placing the vial in ice and exposing the mixture to air.

Purification: Polymer purification was done from acetone/DMF 1:1 into hexane/ether 75/25 (three times). The resulting polymer was dried under vacuum for at least 18 hours. The NMR spectrum showed a high purity of the polymer. No vinyl groups were observed. The polymer was dialysed from ethanol against double de-ionized water for 4 days and then lyophilized. The polymer was analyzed by gel permeation chromatography (GPC) using the following conditions: Solvent: DMF/LiBr 1%. Flow rate: 0.75 ml/min. Injection volume: 100 μl.

Column temperature: 60° C. Poly (styrene) was used to calibrate the detectors. GPC analysis of the resulting Polymer: Mn=40889 g/mol. PDI=1.43. dn/dc=0.049967.

Example 20.3. Synthesis of Gal-[DMAEMA]-[BMA-PAA-DMAEMA]

Figure 13:
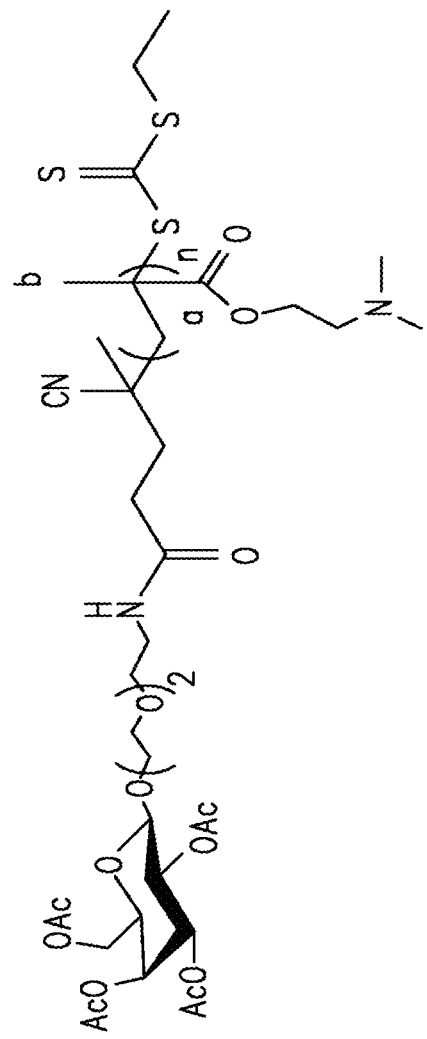
FIG. 13: An illustrative example of the galactose end functionalized poly [DMAEMA]-macro CTA.

Synthesis was carried out as described in example 20.2. First, a galactose-DMAEMA macro-CTA was prepared (example 20.2.A.) except that galactose-CTA (example 20.1, cpd 4) was used in place of ECT as the chain transfer agent. This resulted in the synthesis of a polyDMAEMA with an end functionalized galactose (FIG. 13). The galactose-[DMAEMA]-macro-CTA was then used to synthesize the second block [BMA-PAA-DMAEMA] as described in example 20.2.B. Following synthesis, the acetyl protecting groups on the galactose were removed by incubation in 100 mM sodium bicarbonate buffer, pH 8.5 for 2 hrs, followed by dialysis and lyophilization. NMR spectroscopy was used to confirm the presence of the deprotected galactose on the polymer.

Example 20.4. Preparation and Characterization of [PEGMA-MAA(NHS)]-[B-P-D] and DMAEMA-MMA(NHS)-[B-P-D] Diblock Co-Polymers Polymer synthesis was performed as described in example 20.2 (and summarized in FIG. 14) using monomer feed ratios to obtain the desired composition of the $1^{st}$ block copolymer. FIG. 15 summarizes the synthesis and characterization of [PEGMA-MAA(NHS)]-[B-P-D] polymer where the co-polymer ratio of monomers in the $1^{st}$ block is 70:30.

Figure 16:
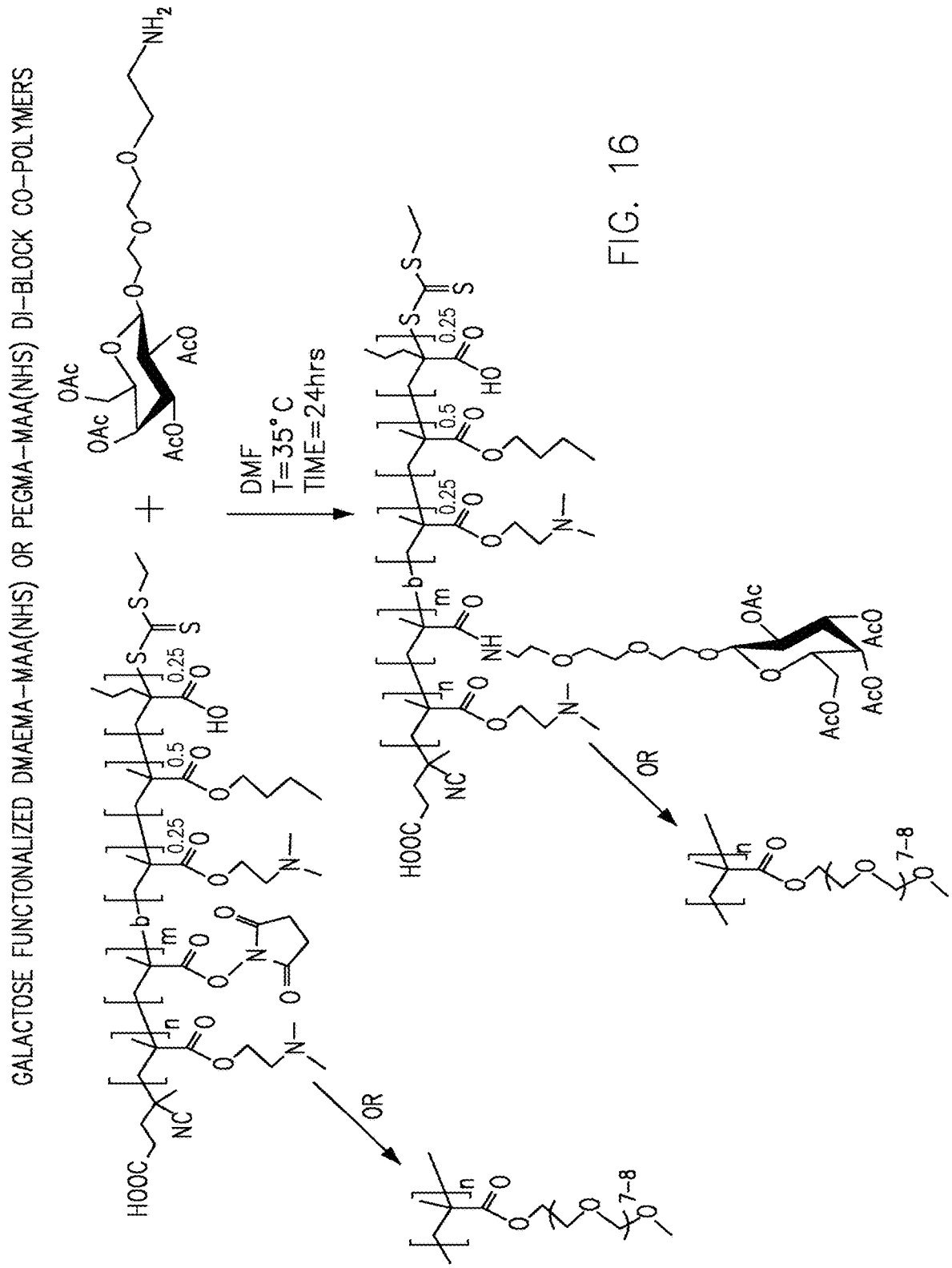
FIG. 16: An illustrative example of the galactose functionalized DMAEMA-MAA(NHS) or PEGMA-MAA (NHS) di-block co-polymers.

Example 20.5. Conjugation of Galactose-PEG-Amine to PEGMA-MAA(NHS) to Produce [PEGMA-MAA(Gal)J-[B-P-D] Polymer FIG. 16 illustrates the preparation of galactose functionalized DMAEMA-MAA(NHS) or PEGMA-MAA(NHS) diblock co-polymers. Polymer [DMAEMA-MAA(NHS)]-[B-P-D] or [PEGMA-MAA(NHS)]-[B-P-D] was dissolved in DMF at a concentration between 1 and 20 mg/ml. Galactose-PEG-amine prepared as described in example 20.1 (cpd 3) was neutralized with 1-2 equivalents of triethylamine and added to the reaction mixture at a ratio of 5 to 1 amine to polymer. The reaction was carried at 35° C. for 6-12 hrs, followed by addition of an equal volume of acetone, dialysis against deionized water for 1 day and lyophilization.

Figure 17A:
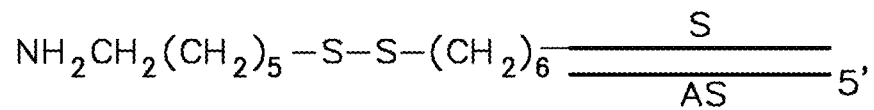
FIGS. 17A, 17B, 17C, and 17D: illustrative examples of the structures of conjugatable siRNAs, peptides, and pyridyl disulfide amine.
Figure 17B:
Figure 17C:
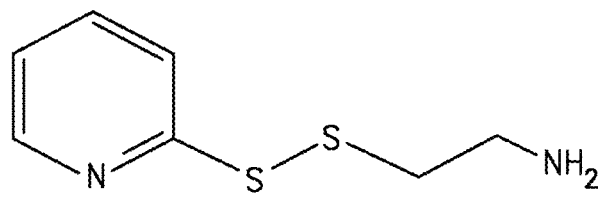

Example 20.6. Conjugation of siRNA to PEGMA-MAA(NHS)]-[B-P-D] to Produce [PEGMA-MAA(RNA)]-[B-P-D] Polymer FIGS. 17A and B shows the structures of 2 modified siRNAs that can be conjugated to NHS containing polymers prepared as described in example 20.4. siRNAs were obtained from Agilent (Boulder, Colo.). FIG. 17C shows the structure of pyridyl disulfide amine used to derivatize NHS containing polymers to provide a disulfide reactive group for the conjugation of thiolated RNA (FIG. 17B).

Reaction of NHS containing polymer with amino-disulfide-siRNA. The reaction is carried out under standard conditions consisting of an organic solvent (for example, DMF or DMSO, or a mixed solvent DMSO/buffer pH 7.8.) at 35° C. for 4-8 hrs, followed by addition of an equal volume of acetone, dialysis against deionized water for 1 day and lyophilization.

Reaction of NHS containing polymer with pyridyl-disulfide-amine and reaction with thiolated siRNA. Reaction of pyridyl disulfide amine with NHS containing polymers is carried out as described in example 20.5. Subsequently the lyophilized polymer is dissolved in ethanol at 50 mg/ml and diluted 10-fold in sodium bicarbonate buffer at pH 8. Thiolated siRNA (FIG. 17B) is reacted at a 2-5 molar excess over polymer NHS groups at 35° C. for 4-8 hrs, followed by dialysis against phosphate buffer, pH 7.4.

Figure 17D:
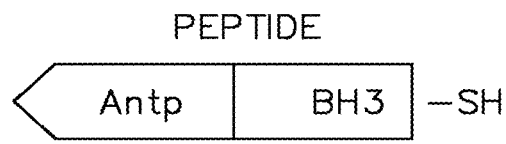

Example 20.7. Conjugation of a Therapeutic Peptide to a Pyridyl-Disulfide Modified Polymer The pyridyl-disulfide modified polymer described in Example 20.6, PEGMA-MAA(NHS)]-[B-P-D], can also be used for conjugation to a therapeutic peptide (FIG. 17D). The peptide is synthesized, prepared for conjugation, and the conjugation reaction carried out as described below, to produce [PEGMA-MAA(Peptide)]-[B-P-D] polymer.

Fusion with the peptide transduction domain peptide transportin (also know as the Antennapedia peptide (Antp) sequence is utilized to synthesize a cell internalizing form of the Bak-BH3 peptide (Antp-BH3) containing a carboxy-terminal cysteine residue (NH2-RQIKIWFQNRRMKWKKMGQVGRQLAIIGDDINR-RYDSC-COOH (SEQ ID NO:9)). TO ensure free thiols for conjugation, the peptide is reconstituted in water and treated for 1 hour with the disulfide reducing agent TCEP immobilized within an agarose gel. The reduced peptide (400 µM) is then reacted for 24 hours with the pyridyl disulfide end-functionalized polymer in phosphate buffer (pH 7) containing 5 mM ethylenediaminetetraacetic acid (EDTA).

Reaction of the pyridyl disulfide polymer end group with the peptide cysteine creates 2-pyridinethione, which can be spectrophotometrically measured to characterize conjugation efficiency. To further validate disulfide exchange, the conjugates are run on an SDS-PAGE 16.5% tricine gel. In parallel, aliquots of the conjugation reactions are treated with immobilized TCEP prior to SDS-PAGE to verify release of the peptide from the polymer in a reducing environment.

Conjugation reactions are conducted at polymer/peptide stoichiometries of 1, 2, and 5. UV spectrophotometric absorbance measurements at 343 nm for 2-pyridinethione release indicates conjugation efficiency. An SDS PAGE gel is utilized to further characterize peptide-polymer conjugates. At a polymer/peptide molar ratio of 1, a detectable quantity of the peptide forms dimers via disulfide bridging through the terminal cysteine. However, the thiol reaction to the pyridyl disulfide is favored, and the free peptide band is no longer visible at polymer/peptide ratios equal to or greater than 2. By treating the conjugates with the reducing agent TCEP, it is possible to cleave the polymer-peptide disulfide linkages as indicated by the appearance of the peptide band in these samples.

The embodiments of the invention in which an exclusive property or privilege is claimed are defined as follows:

1. A micelle-like assembly, wherein the micelle-like assembly comprises a plurality of block copolymers of Formula I:

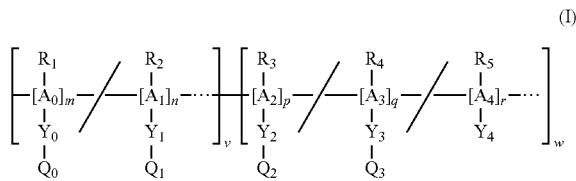

wherein $A_0$, $A_1$, $A_2$, $A_3$ and $A_4$ are independently selected from the group consisting of —C—, —C—C—, —C(O)(C)$_a$C(O)O—, —O(C)$_a$C(O)—, and —O(C)$_b$O—; wherein, a is 1-4;

b is 2-4;

$Y_4$ is selected from the group consisting of hydrogen, -(1C-10C)alkyl,-(3C-6C)cycloalkyl, —O—(1C-10C) alkyl, —C(O)O(1C-10C)alkyl, -(4C-10C)heteroaryl, and -(6C-10C)aryl, any of which is optionally substituted with one or more fluorine groups;

$Y_0$, $Y_1$, and $Y_2$ are independently selected from the group consisting of a covalent bond, -(1C-10C)alkyl-, —C(O)O(2C-10C) alkyl-, —OC(O)(1C-10C) alkyl-, —O(2C-10C)alkyl-, —S(2C-10C)alkyl-, —C(O)NR$_6$(2C-10C) alkyl-, -(4C-10C)heteroaryl-, and -(6C-10C)aryl-;

$Y_3$ is selected from the group consisting of a covalent bond, -(1C-10C)alkyl-, -(4C-10C)heteroaryl-, and -(6C-10C)aryl-;

wherein tetravalent carbon atoms of $A_0$-$A_4$ that are not fully substituted with $R_1$-$R_5$ and $Y_0$-$Y_4$ are completed with an appropriate number of hydrogen atoms;

$R_1$, $R_2$, $R_3$, $R_4$, $R_5$, and $R_6$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_0$ is a residue selected from the group consisting of residues which are hydrophilic at physiologic pH; conjugatable or functionalizable residues; and hydrogen;

$Q_1$ is a residue which is hydrophilic at physiological pH;

$Q_2$ is a residue which is positively charged at physiological pH;

$Q_3$ is a residue which is negatively charged at physiological pH, but undergoes protonation at lower pH;

m is a mole fraction of about 0 to less than 1.0;

n is a mole fraction of greater than 0 to about 1.0; wherein m+n=1;

p is a mole fraction of 0.1 to 0.9;

q is a mole fraction of 0.1 to 0.9;

r is present up to a mole fraction of 0.8; wherein p+q+r=1;

v is from about 1 to about 25 kDa; and w is from about 1 to about 50 kDa.

2. The micelle-like assembly of claim 1, wherein $Q_1$ is a polyethylene glycol group.

3. The micelle-like assembly of claim 1, wherein the micelle-like assembly comprises at least one therapeutic agent.

4. The micelle-like assembly of claim 3, wherein the therapeutic agent is associated with the copolymer.

5. The micelle-like assembly of claim 4, wherein the therapeutic agent is ionically associated with the copolymer.

6. The micelle-like assembly of claim 3, wherein the therapeutic agent is a polynucleotide, an oligonucleotide, a gene expression modulator, a knockdown agent, an siRNA, an RNAi agent, a dicer substrate, an miRNA, an shRNA, an antisense oligonucleotide, or an aptamer.

7. The micelle-like assembly of claim 3, wherein the therapeutic agent is an siRNA.

8. The micelle-like assembly of claim 1, wherein v is from about 5 to about 25 kDa.

9. The micelle-like assembly of claim 1, wherein w is from about 5 to about 50 kDa.

10. The micelle-like assembly of claim 1, wherein the ratio of w to v is from 5:1 to 1:1.

11. The micelle-like assembly of claim 1, wherein $Q_0$ is a residue selected from the group consisting of amino, alkylamino, ammonium, alkylammonium, guanidine, imidazolyl, pyridyl, carboxyl, sulfonamide, boronate, phosphonate, phosphate, hydroxy, polyoxylated alkyl, polyethylene glycol, polypropylene glycol, thiol, azide, alkyne, succinimide ester, tetrafluorophenyl ester, pentafluorophenyl ester, p-nitrophenyl ester, pyridyl disulfide, and hydrogen;

$Q_1$ is a residue selected from the group consisting of amino, alkylamino, ammonium, alkylammonium, guanidine, imidazolyl, pyridyl, carboxyl, sulfonamide, boronate, phosphonate, phosphate, hydroxy, polyoxylated alkyl, polyethylene glycol, polypropylene glycol, and thiol;

$Q_2$ is a residue selected from the group consisting of amino, alkylamino, ammonium, alkylammonium, guanidine, imidazolyl, and pyridyl; and $Q_3$ is a residue selected from the group consisting of carboxyl, sulfonamide, boronate, phosphonate, and phosphate.

12. The micelle-like assembly of claim 1, wherein $R_3$-$A_2$-$Y_2$-$Q_2$ is a residue of dimethylaminoethylmethacrylate (DMAEMA), $R_4$-$A_3$-$Y_3$-$Q_3$ is a residue of propyl acrylic acid (PAA), and $R_5$-$A_4$-$Y_4$ is a residue of butyl methacrylate (BMA).

13. The micelle-like assembly of claim 1, wherein the diblock copolymer, having the chemical Formula I is a diblock copolymer of the Formula IV2:

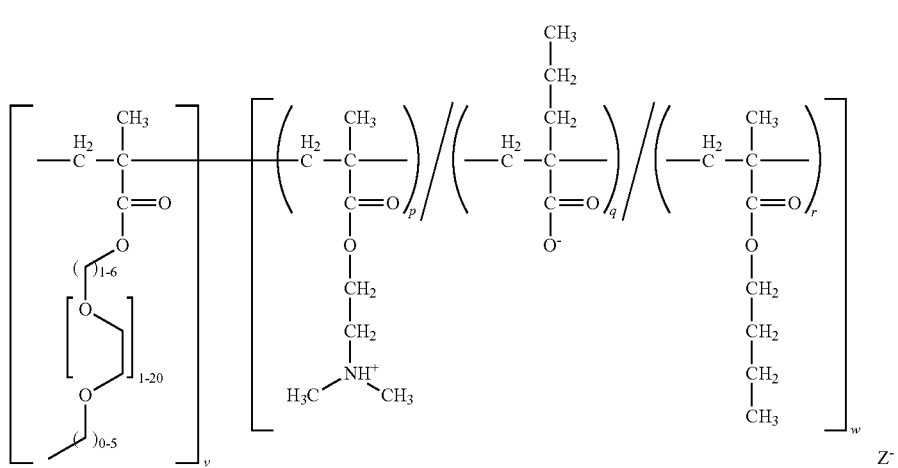

IV2 wherein
p is a mole fraction of 0.1 to 0.9;
q is a mole fraction of 0.1 to 0.9;
r is present up to a mole fraction of 0.8, wherein p+q+r=1;
v is from 1 to 25 kDa;
w is from 1 to 50 kDa; and
$Z^-$ is a physiological acceptable counterion.

14. The micelle-like assembly of claim 13, wherein $Z^-$ is selected from the group consisting of hydroxide, chloride, phosphate, sulfate, sulfonate, acetate, propionate, butyrate, valerate, caproate, caprylate, caprate, laurate, myristate, palmate, stearate, palmitolate, oleate, linolate, arachidate, gadoleate, vaccinate, lactate, glycolate, salicylate, desaminophenylalanine, desaminoserine, desaminothreonine, E-hydroxycaproate, 3-hydroxybutylrate, 4-hydroxybutyrate and 3-hydroxyvalerate.

15. The micelle-like assembly of claim 13, wherein $Z^-$ is hydroxide.

16. A composition comprising the micelle-like assembly of claim 1.

* * * * *

SEQUENCE LISTING

```
<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(25)
<223> OTHER INFORMATION: Sequence is DNA/RNA hybrid
<220> FEATURE:
<221> NAME/KEY: misc_feature
<222> LOCATION: (1)..(23)
<223> OTHER INFORMATION: Wherein each of the nucleotides from position 1
      to 23 are ribonucleotides
<220> FEATURE:
<221> NAME/KEY: misc_feature
<222> LOCATION: (24)..(25)
<223> OTHER INFORMATION: Wherein each of the nucleotides from position
      24 to 25 are deoxynucleotides

<400> SEQUENCE: 1
ggucauccau gacaacuuug guatc                                              25

<210> SEQ ID NO 2
<211> LENGTH: 27
<212> TYPE: RNA
<213> ORGANISM: Artificial Sequence
<220> FEATURE:
<223> OTHER INFORMATION: Synthetic

<400> SEQUENCE: 2
gauaccaaag uugucaugga ugaccuu                                            27

<210> SEQ ID NO 3
<211> LENGTH: 21
<212> TYPE: RNA
<213> ORGANISM: Artificial Sequence
<220> FEATURE:
<223> OTHER INFORMATION: Synthetic

<400> SEQUENCE: 3
gaaugugggu ggcaacuuua g                                                  21

<210> SEQ ID NO 4
<211> LENGTH: 21
<212> TYPE: RNA
<213> ORGANISM: Artificial Sequence
<220> FEATURE:
<223> OTHER INFORMATION: Synthetic

<400> SEQUENCE: 4
aaaguugcca cccacauuca g                                                  21

<210> SEQ ID NO 5
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(25)
<223> OTHER INFORMATION: Sequence is DNA/RNA hybrid
<220> FEATURE:
<221> NAME/KEY: misc_feature
<222> LOCATION: (1)..(23)
<223> OTHER INFORMATION: Wherein each of the nucleotides from position 1
```

```
            to 23 are ribonucleotides
<220> FEATURE:
<221> NAME/KEY: misc_feature
<222> LOCATION: (24)..(25)
<223> OTHER INFORMATION: Wherein each of the nucleotides from position
      24 to 25 are deoxynucleotides

<400> SEQUENCE: 5 gaauguggu ggcaacuuua aagga                                          25

<210> SEQ ID NO 6
<211> LENGTH: 27
<212> TYPE: RNA
<213> ORGANISM: Artificial Sequence
<220> FEATURE:
<223> OTHER INFORMATION: Synthetic

<400> SEQUENCE: 6
uccuuuaaag uugccaccca cauucag                                       27

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
gtccctgaag atgtcaatgc                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
atgtcaatgc cacatgtcca                                               20

<210> SEQ ID NO 9
<211> LENGTH: 38
<212> TYPE: PRT
<213> ORGANISM: Artificial Sequence
<220> FEATURE:
<223> OTHER INFORMATION: Synthetic

<400> SEQUENCE: 9

Arg Gln Ile Lys Ile Trp Phe Gln Asn Arg Arg Met Lys Trp Lys Lys
1               5                   10                  15

Met Gly Gln Val Gly Arg Gln Leu Ala Ile Ile Gly Asp Asp Ile Asn
            20                  25                  30

Arg Arg Tyr Asp Ser Cys
        35
```